US009801543B2

(12) United States Patent
Gross et al.

(10) Patent No.: US 9,801,543 B2
(45) Date of Patent: *Oct. 31, 2017

(54) HAND-HELD MEDICAL-DATA CAPTURE-DEVICE HAVING DETECTION OF BODY CORE TEMPERATURE BY A MICROPROCESSOR FROM A SIGNAL FROM A DIGITAL INFRARED SENSOR ON A SEPARATE CIRCUIT BOARD WITH NO A/D CONVERTER AND HAVING INTEROPERATION WITH ELECTRONIC MEDICAL RECORD STATIC IP ADDRESS SYSTEM

(71) Applicants: Irwin Gross, Boca Raton, FL (US); Michael G. Smith, Austin, TX (US); Mark Khachaturian, Boca Raton, FL (US); Martin Crawley, Belfast (GB); Steven Gerst, Boca Raton, FL (US); John Barrett, Cork (IE); Michael Cronin, Cork (IE); Derek Turnbull, Cork (IE); Jason Bodnick, Boca Raton, FL (US)

(72) Inventors: Irwin Gross, Boca Raton, FL (US); Michael G. Smith, Austin, TX (US); Mark Khachaturian, Boca Raton, FL (US); Martin Crawley, Belfast (GB); Steven Gerst, Boca Raton, FL (US); John Barrett, Cork (IE); Michael Cronin, Cork (IE); Derek Turnbull, Cork (IE); Jason Bodnick, Boca Raton, FL (US)

(73) Assignee: Arc Devices, LTD, Galway (IE)

( * ) Notice: Subject to any disclaimer, the term of this patent is extended or adjusted under 35 U.S.C. 154(b) by 11 days.

This patent is subject to a terminal disclaimer.

(21) Appl. No.: 14/583,810

(22) Filed: Dec. 29, 2014

(65) Prior Publication Data

US 2016/0113499 A1 Apr. 28, 2016

Related U.S. Application Data

(63) Continuation of application No. 14/523,890, filed on Oct. 25, 2014.

(51) Int. Cl.
*G08B 23/00* (2006.01)
*A61B 5/00* (2006.01)
(Continued)

(52) U.S. Cl.
CPC .......... *A61B 5/0008* (2013.01); *A61B 5/0013* (2013.01); *A61B 5/0022* (2013.01);
(Continued)

(58) Field of Classification Search
CPC .......... A61B 5/01; G01K 15/005; G01K 7/24; G01K 2217/00; G01K 7/20; G01K 7/00; G01K 7/18; G01K 3/00; G01K 7/21
(Continued)

(56) References Cited

U.S. PATENT DOCUMENTS 4,315,150 A  2/1982 Darringer et al.
4,322,012 A  3/1982 Conti
(Continued)

FOREIGN PATENT DOCUMENTS

DE  19827343 A1  12/1999
EP  2045590 A1  4/2009
(Continued)

OTHER PUBLICATIONS

Bai, J., et al., "Selectively de-animating video," ACM Transactions on Graphics, (2012).
(Continued)

*Primary Examiner* — Fabricio R Murillo Garcia
(74) *Attorney, Agent, or Firm* — Michael G. Smith, Esq.

(57) ABSTRACT

In one implementation, an apparatus estimates body core temperature from an infrared measurement of an external source point using a cubic relationship between the body core temperature and the measurement of an external source point is described, estimates temperature from a digital infrared sensor and determines vital signs from a solid-state image transducer, or determines vital signs from a solid-state image transducer and estimates body core temperature from an infrared measurement of an external source point using a cubic relationship between the body core temperature and the measurement of an external source point; after which the estimated and/or determined information is transmitted to an external database.

11 Claims, 41 Drawing Sheets

(51) Int. Cl.
| | | |
|---|---|---|
| A61B 5/01 | (2006.01) | |
| G06F 19/00 | (2011.01) | |
| A61B 5/021 | (2006.01) | |
| A61B 5/026 | (2006.01) | |
| A61B 5/08 | (2006.01) | |
| A61B 5/024 | (2006.01) | |
| A61B 5/0205 | (2006.01) | |
| G06T 3/40 | (2006.01) | |
| G06T 7/00 | (2017.01) | |
| H04W 48/16 | (2009.01) | |
| H04W 76/02 | (2009.01) | |
| A61B 5/0402 | (2006.01) | |
| A61B 5/03 | (2006.01) | |
| G01J 5/00 | (2006.01) | |
| H04W 80/04 | (2009.01) | |
| G01J 5/02 | (2006.01) | |
| G01J 5/10 | (2006.01) | |
| G08C 17/02 | (2006.01) | |
| H04L 29/08 | (2006.01) | |
| H04W 12/06 | (2009.01) | |
| H04B 7/26 | (2006.01) | |
| H04L 12/46 | (2006.01) | |
| H04N 5/33 | (2006.01) | |
| H04W 48/08 | (2009.01) | |
| G08B 5/36 | (2006.01) | |
| G08B 21/18 | (2006.01) | |
| G01K 13/00 | (2006.01) | |
| G06K 9/62 | (2006.01) | |
| G06T 7/174 | (2017.01) | |
| G06T 7/269 | (2017.01) | |
| G06T 7/90 | (2017.01) | |
| A61B 5/0245 | (2006.01) | |
| H04W 12/08 | (2009.01) | |

(52) U.S. Cl.
CPC .......... *A61B 5/0059* (2013.01); *A61B 5/0075* (2013.01); *A61B 5/0077* (2013.01); *A61B 5/01* (2013.01); *A61B 5/015* (2013.01); *A61B 5/021* (2013.01); *A61B 5/02055* (2013.01); *A61B 5/0261* (2013.01); *A61B 5/02433* (2013.01); *A61B 5/03* (2013.01); *A61B 5/0402* (2013.01); *A61B 5/08* (2013.01); *A61B 5/441* (2013.01); *A61B 5/6887* (2013.01); *A61B 5/6898* (2013.01); *A61B 5/725* (2013.01); *A61B 5/7225* (2013.01); *A61B 5/7264* (2013.01); *A61B 5/7271* (2013.01); *A61B 5/7275* (2013.01); *A61B 5/7278* (2013.01); *A61B 5/746* (2013.01); *A61B 5/7425* (2013.01); *A61B 5/7475* (2013.01); *G01J 5/0025* (2013.01); *G01J 5/025* (2013.01); *G01J 5/10* (2013.01); *G01K 13/004* (2013.01); *G06F 19/322* (2013.01); *G06F 19/3406* (2013.01); *G06F 19/3418* (2013.01); *G06K 9/6218* (2013.01); *G06T 3/40* (2013.01); *G06T 7/0012* (2013.01); *G06T 7/174* (2017.01); *G06T 7/269* (2017.01); *G06T 7/90* (2017.01); *G08B 5/36* (2013.01); *G08B 21/182* (2013.01); *G08C 17/02* (2013.01); *H04B 7/26* (2013.01); *H04L 12/4633* (2013.01); *H04L 67/04* (2013.01); *H04L 67/10* (2013.01); *H04L 67/12* (2013.01); *H04L 67/16* (2013.01); *H04L 67/20* (2013.01); *H04L 67/22* (2013.01); *H04N 5/33* (2013.01); *H04W 12/06* (2013.01); *H04W 48/08* (2013.01); *H04W 48/16* (2013.01); *H04W 76/02* (2013.01); *H04W 76/022* (2013.01); *H04W 80/04* (2013.01); *A61B 5/024* (2013.01); *A61B 5/0245* (2013.01); *A61B 5/742* (2013.01); *A61B 2560/0214* (2013.01); *A61B 2560/0475* (2013.01); *A61B 2562/166* (2013.01); *A61B 2576/00* (2013.01); *G06T 2207/10048* (2013.01); *G06T 2207/20024* (2013.01); *G06T 2207/20132* (2013.01); *G06T 2207/30004* (2013.01); *G06T 2207/30088* (2013.01); *G06T 2207/30104* (2013.01); *G06T 2210/22* (2013.01); *G06T 2210/41* (2013.01); *H04W 12/08* (2013.01)

(58) Field of Classification Search
USPC ...................................................... 340/573.1
See application file for complete search history.

(56) References Cited

U.S. PATENT DOCUMENTS

| | | |
|---|---|---|
| 4,602,642 A | 4/1986 | O'Hara et al. |
| 4,797,840 A | 1/1989 | Fraden |
| 5,133,605 A | 7/1992 | Nakamura |
| 5,150,969 A | 9/1992 | Goldberg et al. |
| 5,272,340 A | 12/1993 | Anbar |
| 5,368,038 A | 11/1994 | Fraden |
| 5,743,644 A | 4/1998 | Kobayashi |
| 6,095,682 A | 8/2000 | Hollander et al. |
| 6,286,994 B1 | 9/2001 | Boesel et al. |
| 6,292,685 B1 | 9/2001 | Pompei |
| 6,343,141 B1 | 1/2002 | Okada et al. |
| 6,358,216 B1 | 3/2002 | Kraus et al. |
| 6,587,701 B1 | 7/2003 | Stranc et al. |
| 6,742,927 B2 | 6/2004 | Bellifemine |
| 6,751,342 B2 | 6/2004 | Shepard |
| 6,757,412 B1 | 6/2004 | Parsons |
| 6,832,000 B2 | 12/2004 | Herman et al. |
| 7,092,376 B2 | 8/2006 | Schuman |
| 7,140,768 B2 | 11/2006 | Prabhakar |
| 7,339,685 B2 | 3/2008 | Carlson et al. |
| 7,346,386 B2 | 3/2008 | Pompei |
| 7,520,668 B2 | 4/2009 | Chen |
| 7,572,056 B2 | 8/2009 | Lane |
| 7,787,938 B2 | 8/2010 | Pompei |
| 8,213,689 B2 | 7/2012 | Yagnik et al. |
| 8,401,285 B1 | 3/2013 | Rezaee et al. |
| 8,452,382 B1 | 5/2013 | Roth |
| 8,493,482 B2 | 7/2013 | Cote et al. |
| 8,517,603 B2 | 8/2013 | Fraden |
| 8,527,038 B2 | 9/2013 | Moon et al. |
| 8,617,081 B2 | 12/2013 | Mestha et al. |
| 8,693,739 B2 | 4/2014 | Weng et al. |
| 8,849,379 B2 | 9/2014 | Abreu |
| 2001/0005424 A1 | 6/2001 | Marksteiner |
| 2002/0077850 A1 | 6/2002 | McMenimen et al. |
| 2002/0172410 A1 | 11/2002 | Shepard |
| 2004/0013162 A1 | 1/2004 | Beerwerth |

(56) References Cited

U.S. PATENT DOCUMENTS

| | | |
|---|---|---|
| 2004/0116822 A1 | 6/2004 | Lindsey |
| 2004/0120383 A1 | 6/2004 | Kennedy et al. |
| 2004/0153341 A1 | 8/2004 | Brandt et al. |
| 2004/0193068 A1 | 9/2004 | Burton et al. |
| 2005/0023991 A1 | 2/2005 | Kemper |
| 2006/0209631 A1 | 9/2006 | Melese et al. |
| 2006/0225737 A1 | 10/2006 | Lobbi |
| 2006/0293921 A1 | 12/2006 | McCarthy et al. |
| 2007/0080233 A1 | 4/2007 | Forster et al. |
| 2007/0183475 A1 | 8/2007 | Hutcherson |
| 2008/0175301 A1 | 7/2008 | Chen |
| 2008/0281168 A1 | 11/2008 | Gibson et al. |
| 2009/0100333 A1 | 4/2009 | Xiao |
| 2009/0141124 A1 | 6/2009 | Liu et al. |
| 2009/0172591 A1 | 7/2009 | Pomper |
| 2009/0175317 A1 | 7/2009 | Chan et al. |
| 2009/0196475 A1 | 8/2009 | Demirli et al. |
| 2009/0221880 A1 | 9/2009 | Soderberg et al. |
| 2010/0030577 A1* | 2/2010 | Lawson .......... G06Q 50/24 705/3 |
| 2010/0049077 A1 | 2/2010 | Sadleir et al. |
| 2010/0056928 A1 | 3/2010 | Zuzak |
| 2011/0112791 A1 | 5/2011 | Pak et al. |
| 2011/0121978 A1* | 5/2011 | Schworer .......... G01J 5/02 340/588 |
| 2011/0199203 A1 | 8/2011 | Hsu |
| 2011/0228810 A1* | 9/2011 | O'Hara .......... G01J 5/0003 374/121 |
| 2011/0228811 A1 | 9/2011 | Fraden |
| 2011/0251493 A1 | 10/2011 | Poh et al. |
| 2011/0276698 A1 | 11/2011 | Bigioi et al. |
| 2011/0286644 A1 | 11/2011 | Kislal |
| 2012/0005248 A1 | 1/2012 | Garudadri et al. |
| 2012/0022348 A1 | 1/2012 | Droitcour et al. |
| 2012/0130251 A1 | 5/2012 | Huff |
| 2012/0130252 A1 | 5/2012 | Pohjanen et al. |
| 2012/0150482 A1 | 6/2012 | Yildizyan et al. |
| 2012/0242844 A1 | 9/2012 | Walker et al. |
| 2013/0006093 A1 | 1/2013 | Raleigh et al. |
| 2013/0035599 A1 | 2/2013 | De Bruijn et al. |
| 2013/0172770 A1 | 7/2013 | Muehlsteff |
| 2013/0204570 A1* | 8/2013 | Mendelson .......... G01J 5/0025 702/135 |
| 2013/0211265 A1 | 8/2013 | Bedingham et al. |
| 2013/0215928 A1 | 8/2013 | Bellifemine |
| 2013/0245462 A1 | 9/2013 | Capdevila et al. |
| 2013/0271591 A1 | 9/2013 | Van Leest et al. |
| 2013/0307536 A1 | 10/2013 | Feng et al. |
| 2013/0296716 A1 | 11/2013 | Kurzenberger |
| 2013/0322729 A1 | 12/2013 | Mestha et al. |
| 2013/0342691 A1 | 12/2013 | Lewis et al. |
| 2014/0003461 A1 | 1/2014 | Roth |
| 2014/0003462 A1 | 1/2014 | Roth |
| 2014/0064327 A1 | 3/2014 | Roth |
| 2014/0064328 A1 | 3/2014 | Roth |
| 2014/0064333 A1* | 3/2014 | Roth .......... G01K 1/028 374/170 |
| 2014/0072190 A1 | 3/2014 | Wu et al. |
| 2014/0072228 A1 | 3/2014 | Rubinstein |
| 2014/0072229 A1 | 3/2014 | Wadhwa |
| 2014/0088434 A1 | 3/2014 | Roth |
| 2014/0088435 A1 | 3/2014 | Roth |
| 2014/0088436 A1 | 3/2014 | Roth |
| 2014/0112367 A1 | 4/2014 | Roth |
| 2014/0114600 A1 | 4/2014 | Roth |
| 2014/0155759 A1 | 6/2014 | Walter et al. |
| 2014/0189576 A1 | 7/2014 | Carmi |
| 2014/0232516 A1 | 8/2014 | Stivoric et al. |
| 2014/0253709 A1 | 9/2014 | Bresch et al. |
| 2014/0321505 A1 | 10/2014 | Rill et al. |
| 2015/0088538 A1 | 3/2015 | Dykes et al. |
| 2015/0110153 A1 | 4/2015 | Hoblit et al. |
| 2015/0257653 A1* | 9/2015 | Hyde .......... A61B 5/021 600/473 |
| 2015/0339805 A1 | 11/2015 | Ohba |
| 2016/0035084 A1 | 2/2016 | Khachaturian et al. |

FOREIGN PATENT DOCUMENTS

| | | |
|---|---|---|
| EP | 2380493 A1 | 10/2011 |
| EP | 2674735 A1 | 12/2013 |
| GB | 2291498 A | 1/1996 |
| GB | 2521620 A | 1/2015 |
| WO | 1992002792 A1 | 2/1992 |
| WO | 1998001730 A1 | 1/1998 |
| WO | 1999039166 A1 | 8/1999 |
| WO | 1999067611 A1 | 12/1999 |
| WO | 2011063266 A2 | 5/2011 |
| WO | 2012093311 A1 | 7/2012 |

OTHER PUBLICATIONS

Balakrishnan, Guha, Fredo Durand, and John Guttag. "Detecting pulse from head motions in video." Computer Vision and Pattern Recognition (CVPR), 2013 IEEE Conference on. IEEE, 2013.

Bojanic, S., et al., "Ocular microtremor: a tool for measuring depth of anaesthesia?" British J. Anaesthesia, 86(4): 519-522 (2001).

Burt, P. and Adelson, E., "The laplacian pyramid as a compact image code," IEEE Trans. Comm., 31(4): 532-540 (1983).

Covidien, Filac 3000 EZ-EZA Electronic Thermometer Operating Manual, 2012, http://www.covidien.com/imageServer/aspx?contentID=31819&contenttype=application/pdf, retrieved from the Internet on Jul. 24, 2015.

Fleet, D.J. and Jepson, A.D., "Computation of component image velocity from local phase information," Int. J. Comput., Vision 5(1): 77-104 (Sep. 1990).

Freeman, W.T., et al., "Motion without movement," SIGGRAPH Comput. Graph., 25: 27-30 (Jul. 1991).

Fuchs, M., et al., "Real-time temporal shaping of high-speed video streams," Computers & Graphics, 34(5): 575-584 (2010).

Gautama, T. and Van Hulle, M., "A phase-based approach to the estimation of the optical flow field using spatial filtering", Neural Netlvorks, IEEE Transactions, 13(5): 1127-1136 (Sep. 2002).

Liu, C., et al., "Motion magnification", ACAM Trans. Graph., 24: 519-526 (Jul. 2005).

Lucas, Bruce D., and Takeo Kanade. "An iterative image registration technique with an application to stereo vision." IJCAI. vol. 81.1981.

Ming-Zher Poh et al. Non-contact, automated cardiac pulse measurements using video imaging and blind source separation, Optics Express, 18(10): 10762-10?74, 2010.

Portilla, J. and Simoncelli, E.D., "A parametric texture model based on joint statistics of complex wavelet coefficients," Int. J. Comput. Vision, 49(1 ): 49-70 (Oct. 2000).

Rolfs, M., "Microsaccades: Small steps on a long way," Vision Res., 49(20): 2415-2441 (2009).

Rubinstein, M, "Eulerian Video Magnification" You Tube, http://www.youtube.com/watch?v=ONZcjs1Pjmk, May 23, 2012, 3 pages.

Rubinstein, M., et al., "Motion denoising with application to time-lapse photography," IEEE Computer Vision and Pattern Recognition, CVPR, pp. 313-320 (Jun. 2011).

Simoncelli, E.P. and Freeman, W.T., The steerable pyramid: a flexible architecture for multiscale derivative computation, in Proc. of the 1995 Int'l Conf. on Image Proc., IEEE Computer Society,ICIP, Washington, DC, USA, 3: 3444 (1995).

Timoner Samson J. Subpixel motion estimation from sequences of video images. Diss. Massachusetts Institute of Technology, 1999.

Timoner Samson J., and Dennis M. Freeman. "Multi-image gradient-based algorithms for motion estimation." Optical engineering 40.9 (2001 ): 2003-2016.

Unuma Munetoshi, Ken Anjyo, and Ryozo Takeuchi. "Fourier principles for emotion-based human figure animation." Proceedings of the 22nd annual conference on Computer graphics and interactive techniques. ACM, 1995.

(56) References Cited

OTHER PUBLICATIONS

Verkruysse, Wim, Lars 0. Svaasand, and J. Stuart Nelson. "Remote plethysmographic imaging using ambient light." Optics express 16.26 (2008): 21434-21445.
Viola Paul, and Michael J. Jones. "Robust real-time face detection." International journal of computer vision 57.2 (2004): 137-154.
Wadhwa, Neal, et al. "Phase-based video motion processing." ACM Transactions on Graphics (TOG) 32.4 (2013): 80.
Wadhwa, Neal, et al. "Riesz pyramids for fast phase-based video magnification." Computational Photography (ICCP), 2014 IEEE International Conference on. IEEE, 2014.
Wang J., et al., "The cartoon animation filter," ACM Trans. Graph., 25: 1169-1173 (2006).
Wu, H.-Y., et al., "Eulerian video magnification for revealing subtle changes in the world," ACM Trans. Graph. (Proc. SIGGRAPH), 31 (Aug. 2012).
Rose, "Choosing a Thermometer", Today's Woman Review & Giveaway Blog, Oct. 18, 2015, http://www.todays-woman.net/2015/health-personal-fitness/choosing-a-thermometer/.
Edmund Optics, Imaging Electronics 101: Understanding Camera Sensors for Machine Vision Applications, retrieved from Internet on Jan. 11, 2016 at http://www.edmundoptics.com/technical-resources-center/imaging/understanding-camera-sensors-for-machine-vision-applications/.
wikipedia.com, Category: Data Clustering Algorithms, retrieved from the Internet on Jun. 17, 2014 at http://en.wikipedia.org/wiki/Category:Data_clustering_algorithms.
wikipedia.com, Filter (signal processing), retrieved from the Internet on Jun. 17, 2014 at http://en.wikipedia.org/wiki/Filter_(signal_processing).
R Fisher. S. Perkins. A. Waiker and E. Wolfart, Frequency Filter, Image Processing Learning Resources, 2003, retrieved from the Internet on Jun. 24, 2014 at http://homepages.inf.ed.ac.uk/rbf/HIPR2/freqfilt.htm.
wikipedia.com, Band-pass filter, retrieved from the Internet on Jul. 7, 2014 at http://en.wikipedia.org/wiki/Band-pass_filter.
wikipedia.com, Low-pass filter, retrieved from the Internet on Jul. 7, 2014 at http://en.wikipedia.org/wiki/Low-pass_filter.
wikipedia.com, High-pass filter, retrieved from the Internet on Jul. 7, 2014 at http://en.wikipedia.org/wiki/High-pass_filter.
R Fisher. S. Perkins. A. Walker and E. Wolfart, Fourier Transform, Image Processing Learning Resources, 2003, retrieved from the Internet on Jul. 7, 2014 at http://homepages.inf.ed.ac.uk/rbf/HIPR2/fourier.htm.
wikipedia.com. Expectation-maximization algorithm, retrieved from the Internet on Jul. 7, 2014 at http://en.wikipedia.org/wiki/Expectation-maximization_algorithm.
wikipedia.com, Fuzzy clustering, retrieved from the Internet on Jul. 7, 2014 at http://en.wikipedia.org/wiki/Fuzzy_clustering.
wikipedia.com, k-means clustering, retrieved from the Internet on Jul. 7, 2014 at http://en.wikipedia.org/wiki/K-means_clustering.
Hao-Yu Wu, Eulerian Video Magnification for Revealing Subtle Changes in the World, ACM Transactions on Graphics (TOG)—SIGGRAPH 2012 Conference Proceedings, vol. 31 Issue 4, Jul. 2012, Article No. 65, ACM New York, NY, USA, ISSN: 0730-0301 EISSN: 1557-7368 doi 10.1145/2185520.2185561, published on Jul. 1, 2012, retrieved from the Internet on Jul. 9, 2014 from http://people.csail.mit.edu/billf/publications/Eulearian_Video_Magnification.pdf.
Eduardo S.L. Gastal, Adaptive Manifolds for Real-Time High-Dimensional Filtering, ACM Transactions on Graphics (TOG)—SIGGRAPH 2012 Conference Proceedings, vol. 31 Issue 4, Jul. 2012, Article No. 33, ACM New York, NY, USA, ISSN: 0730-0301 EISSN: 1557-7368, doi10.1145/2185520.2185529, retrieved from the Internet on on Jul. 9, 2013 from http://inf.ufrgs.br/~eslgastal/AdaptiveManifolds/Gastal_Oliveira_SIGGRAPH2012_Adaptive_Manifolds.pdf.
Sunghyun Cho, Video deblurring for hand-held cameras using patch-based synthesis, ACM Transactions on Graphics (TOG)—SIGGRAPH 2012 Conference Proceedings, vol. 31 Issue 4, Jul. 2012, Article No. 64, ACM New York, NY, USA, ISSN: 0730-0301 EISSN: 1557-7368 doi 10.1145/2185520.2185561, published on Jul. 1, 2012, retrieved from the Internet on Jul. 9, 2014 from http://juew.org/publication/video_deblur.pdf.
C. Liu, Motion magnification, ACM SIGGRAPH 2005, pp. 519-526, 2005, retrieved from the Internet on Jul. 9, 2014 fromhttp://people.csail.mit.edu/celiu/pdfs/motionmag.pdf.
O. Arikan, Interactive Motion Generation from Examples, ACM Transactions on Graphics (TOG), Proceedings of ACM SIGGRAPH 2002, vol. 21 Issue 3, Jul. 2002, pp. 483-490, ACM New York, NY, USA, ISBN:1-58113-521-1, doi 10.1145/566654.566606, retrieved from the Internet on Jul. 9, 2014from http://www.okanarikan.com/Papers/SynthesisFromExamples/paper.pdf.

\* cited by examiner

HAND-HELD MEDICAL-DATA CAPTURE-DEVICE HAVING DETECTION OF BODY CORE TEMPERATURE BY A MICROPROCESSOR FROM A SIGNAL FROM A DIGITAL INFRARED SENSOR ON A SEPARATE CIRCUIT BOARD WITH NO A/D CONVERTER AND HAVING INTEROPERATION WITH ELECTRONIC MEDICAL RECORD STATIC IP ADDRESS SYSTEM

RELATED APPLICATION

This application is a continuation of, and claims the benefit and priority under 35 U.S.C. 120 of U.S. Original patent application Ser. No. 14/523,890 filed 25 Oct. 2014, which is hereby incorporated by reference in its entirety.

FIELD

This disclosure relates generally to transmitting a representation of animal body core temperature or other vital signs to an electronic medical record system.

BACKGROUND

Hand-held medical-data capture-devices are stand-alone devices in which data is retrieved from the device by an operator who reads a temperature or other vital sign from a display screen in the hand-held medical-data capture-devices and then manually records the vital sign in an electronic medical record system, which is a very slow and expensive process.

BRIEF DESCRIPTION

In one aspect, an apparatus estimates body core temperature from an infrared measurement of an external source point using a cubic relationship between the body core temperature and the measurement of an external source point and transmits the apparatus estimate of body core temperature to an external device.

In a further aspect, a non-touch biologic detector estimates body core temperature from an infrared measurement of an external source point and determines vital signs from a solid-state image transducer and transmits the apparatus estimate of body core temperature and the vital sign to an external device.

In another aspect, a non-touch biologic detector determines vital signs from a solid-state image transducer and estimates body core temperature from an infrared measurement of an external source point using a cubic relationship between the body core temperature and the measurement of an external source point and transmits the apparatus estimate of body core temperature and the vital sign to an external device.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into ten sections. In the first section, an overview of two implementations is shown. In the second section, implementations of apparatus of digital non-touch thermometers and vital sign variation amplification detectors are described. In the third section, implementations of apparatus of non-touch cubic-estimation thermometers are described. In the fourth section, implementations of apparatus of non-touch cubic estimation thermometers and vital sign detectors are described. In the fifth section, methods of digital infrared thermometers are described. In the sixth section, implementations of apparatus of vital sign variation amplification detectors are described. In the seventh section, implementations of methods of vital sign amplification are described. In the eighth section, implementations of methods of non-touch cubic-estimation are described. In the ninth section, hardware and operating environments in which implementations may be practiced are described. Finally, in the tenth section, a conclusion of the detailed description is provided.

Figure 1:
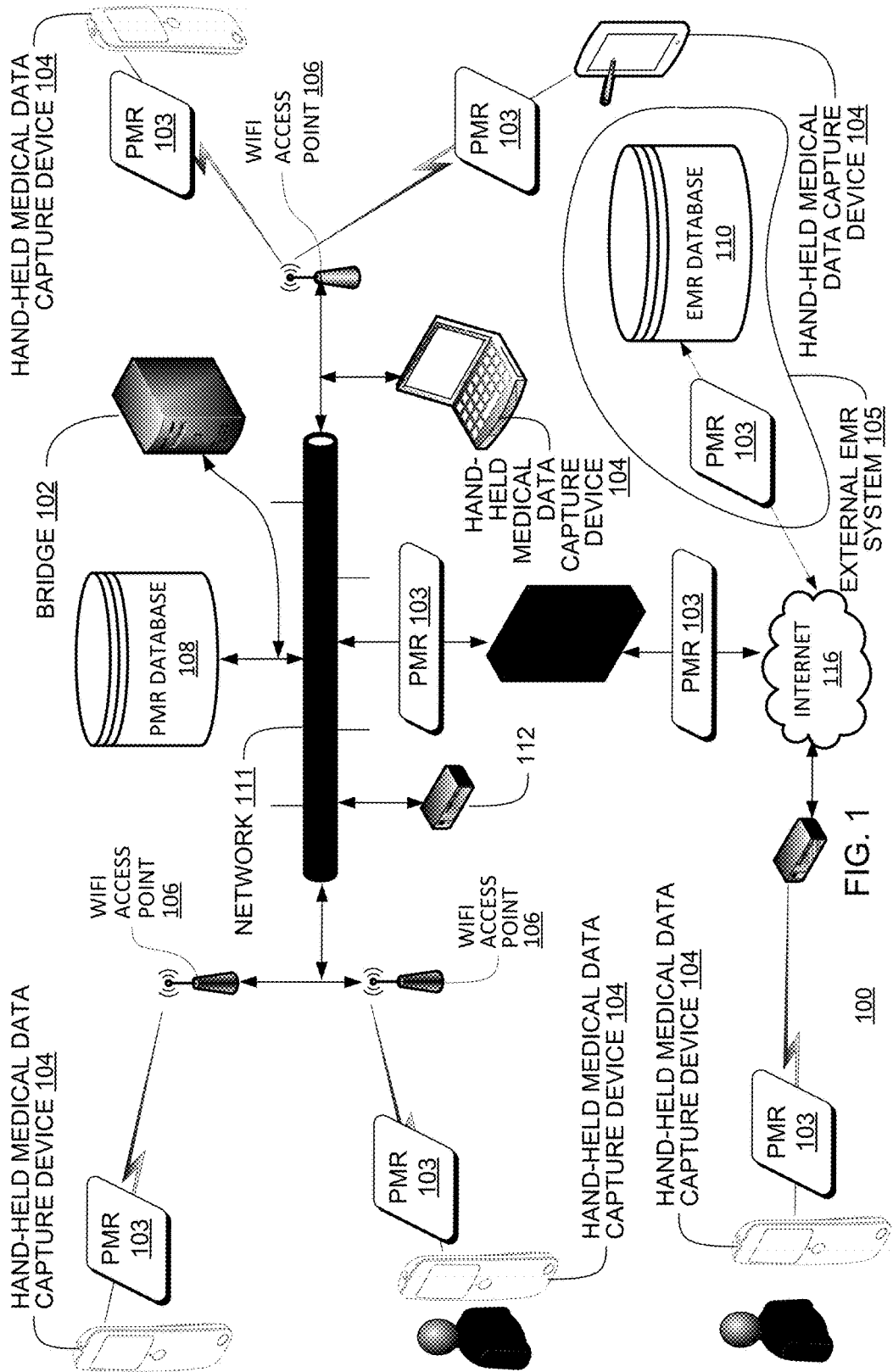
FIG. 1 is a block diagram of an overview of an electronic medical records (EMR) capture system, according to an implementation.

FIG. 1 is a block diagram of an overview of an electronic medical records (EMR) capture system 100, according to an implementation.

FIG. 1 shows high level components of the EMR capture system 100 that includes a network server 102. The network server 102 is also referred to as the "bridge 102". The bridge 102 transfers patient measurement records (PMRs) 103 from hand-held medical-data capture-devices 104 to EMR systems in hospital and clinical environments. Each PMR 103 includes patient measurement data, such as vital sign 136 in FIGS. 1-7 and 7-10, estimated body temperature 412 in FIG. 4-10, vital sign 1416 in FIGS. 14-21, and heartrate 1910, respiratory rate 1916 and EKG 1928 in FIG. 19. Examples of hand-held medical-data capture-devices 104 include non-touch biologic detector in FIGS. 1-3, apparatus that estimates a body core temperature 4-10, apparatus of variation amplification FIGS. 14-18 and 20-22, mobile device 3000 and non-touch thermometer 3300.

The EMR capture system 100 includes two important aspects:

1. A server bridge 102 to control the flow of patient measurement data from hand-held medical-data capture-devices 104 to one or more external EMR systems 105 and to manage local hand-held medical-data capture-devices 104.

2. The transfer of patient measurement data in a PMR 103, anonymous, and other patient status information to a cloud based external EMR system 105.

The bridge 102 controls and manages the flow of patient measurement data to a PMR database 108 and an EMR database 110 and provides management services to hand-held medical-data capture-devices 104.

The bridge 102 provides an interface to:

A wide range of proprietary EMR systems 105.

Location specific services, per hospital, for verification of active operator, and if necessary, patient identifications.

A cloud based data repository (EMR database 105) of one or more hand-held medical-data capture-devices 104, for the purpose of storing all measurement records in an anonymous manner for analysis. A setup, management and reporting mechanism also provided.

The bridge 102 accepts communications from hand-held medical-data capture-devices 104 to:

Data format conversion and transferring patient measurement records to EMR systems 105.

Manage the firmware and configuration settings of the hand-held medical-data capture-devices 104.

Determine current health and status of the hand-held medical-data capture-devices 104.

Support device level protocol for communications, TCP/IP, of that supports the following core features:
Authentication of connected device and bridge 102
Transfer of patient measurement records to Bridge 102 with acknowledgement and acceptance by the bridge 102 or EMR acceptance.
Support for dynamic update of configuration information and recovery of health and status of the hand-held medical-data capture-devices 104.
Support for firmware update mechanism of firmware of hand-held medical-data capture-devices 104.

The EMR capture system 100 provides high availability, 24/7/365, with 99.99% availability.

The EMR capture system 100 provides a scalable server system to meet operational demands in hospital operational environments for one or both of the following deployable cases:

1. A local network 111 at an operational site in which the bridge 102 provides all features and functions in a defined operational network 111 to manage a system of up to 10,000+ hand-held medical-data capture-devices 104.

2. Remote or Cloud based site 105 in which the bridge 102 provides all services to many individual hospital or clinical sites spread over a wide geographical area, for 1,000,000+ hand-held medical-data capture-devices 104.

The bridge 102 provides a central management system for the hand-held medical-data capture-devices 104 that provides at least the following functions:
configuration management and update of the hand-held medical-data capture-devices 104
device level firmware for all of the hand-held medical-data capture-devices 104
management and reporting methods for the hand-held medical-data capture-devices 104, covering but not limited to:
health and status of the hand-held medical-data capture-devices 104
battery level, replacement warning of the hand-held medical-data capture-devices 104
check/calibration nearing warning of the hand-held medical-data capture-devices 104
rechecking due to rough handling or out of calibration period of the hand-held medical-data capture-devices 104
History of use, number of measurements, frequency of use etc. of the hand-held medical-data capture-devices 104
Display of current device configuration of the hand-held medical-data capture-devices 104
Date/time of last device communications with each of the hand-held medical-data capture-devices 104

The bridge 102 provides extendable features, via software updates, to allow for the addition of enhanced features without the need for additional hardware component installation at the installation site. The bridge 102 provides a device level commission mechanism and interface for the initial setup, configuration and test of hand-held medical-data capture-devices 104 on the network 111. The bridge 102 supports medical capture devices that are not hand-held.

Coverage of the EMR capture system 100 in a hospital can include various locations, wards, ER rooms, offices, Dr's Offices etc. or anywhere where automatic management of patient vital sign information is required to be saved to a remote EMR system.

The hand-held medical-data capture-devices 104 can communicate with a third party network bridge 112 to provide access to data storage services, EMR systems, hand-held medical-data capture-devices cloud storage system etc.

Networking setup, configuration, performance characteristics etc. are also determined and carried out by the third party bridge 112 or another third party, for the operational environments. The hand-held medical-data capture-devices can support the network protocols for communication with the third party bridge 112 devices.

In some implementations, a push data model is supported by the EMR capture system 100 between the hand-held medical-data capture-devices 104 and the bridge 102 in which connection and data are initially pushed from the hand-held medical-data capture-device 104 to the bridge 102. Once a connection has been established and the hand-held medical-data capture-devices 104 and the bridge 102, such as an authenticated communication channel, then the roles may be reversed where the bridge 102 will control the flow of information between the hand-held medical-data capture-devices 104 and the EMR system 105.

In some implementations, the hand-held medical-data capture-device 104 are connected to the EMR capture system 100 via a WIFI connection to a Wi-Fi access point 106. In other implementations, the hand-held medical-data capture-device 104 is connected to a docking station via a wireless or physical wired connection, i.e. local isolated WIFI, Bluetooth, serial, USB, etc., in which case the docking station then acts as a local pass-through connection and connects to the bridge 102 via a LAN interface.

In some implementations, the portable hand-held medical-data capture-device 104 includes a battery with limited battery power and lifetime that in some implementations needs to be conserved in order to reduce the intervals at which the battery needs to be recharged. These portable hand-held medical-data capture-devices 104 support various power saving modes and as such each device is responsible for the initiation of a connection to the wireless network and the subsequent connection to the bridge 102 that meets their own specific operational requirements. It is expected that this will provide the hand-held medical-data capture-devices 104 additional control over their own power management usage and lifetime.

In implementations in which the hand-held medical-data capture-devices 104 attempts connection to the bridge 102, the bridge 102 is allocated a static IP address to reduce the IP discovery burden on the hand-held medical-data capture-devices 104 and thus connect the hand-held medical-data capture-device to the bridge 102 more quickly. More specifically, the hand-held medical-data capture-devices 104 are not required to support specific discovery protocols or domain name service (DNS) in order to determine the IP address of the bridge 102. It is therefore very important that the bridge 102 IP address is static and does not change over the operational lifetime of EMR capture system 100 on the network 111.

In some implementations, installation of a new hand-held medical-data capture-device 104 on the network 111 will require configuration of the hand-held medical-data capture-device 104 for the bridge 102 of IP address and other essential network configuration and security information. Commissioning of a hand-held medical-data capture-device 104 on the network 111 in some implementations is carried out from an management interface on the bridge 102. In this way a single management tool can be used over all lifecycle phases of a hand-held medical-data capture-devices 104 on the network 111, such as deployment, operational and decommissioning In some implementations, the initial network configuration of the hand-held medical-data capture-device 104 does not require the hand-held medical-data capture-device 104 to support any automated network level configuration protocols, WPS, Zeroconfi etc. Rather the bridge 102 supports a dual network configuration, one for operational use on the operational network of the hospital or clinic, or other location, and an isolated local network, with local DHCP server, for out of the box commissioning of a new hand-held medical-data capture-device 104 and for diagnostic test of the hand-held medical-data capture-devices 104. Hand-held medical-data capture-devices 104 can be factory configured for known network settings and contain a default server IP address on the commissioning network 111. In addition, the hand-held medical-data capture-devices 104 are required to support a protocol based command to reset the hand-held medical-data capture-device 104 to network factory defaults for test purposes It is commonplace that the firmware revision of the hand-held medical-data capture-devices 104 will not be consistent in the operational environment. Therefore, the bridge 102 is backwards compatible with all released firmware revisions from firmware and protocol revision, data content and device settings view point of the hand-held medical-data capture-device 104. As a result, different revision levels of hand-held medical-data capture-devices 104 can be supported at the same time on the network 111 by the bridge 102 for all operations.

Implementation Alternatives

Limited Operational Features and Implementation Capability

Some implementations of the EMR capture system 100 have limited operational features and implementation capability. A significant function of the EMR capture system 100 with the limited operational features and implementation capability in the bridge 102 is to accept data from a hand-held medical-data capture-device 104 and update the EMR capture system 100.

The following limited feature set in some implementations be supported by the EMR capture system 100 for the demonstrations:

Implementation to a local IT network on a server of the local IT network, OR located on a Cloud-based PMR storage system 105, whichever is achievable in the time frame and meets the operational requirements for third party EMR capture systems.

Acceptance of patient medical records from a hand-held medical-data capture-device 104:
Date and Time
Operator ID
Patient Id
Patient measurement
Device manufacturer, model number and firmware revision Acceptance of limited status information from a hand-held medical-data capture-device 104:
Battery Level
Hospital reference
location reference
Manufacturer identification, serial number and firmware revision
Unique id number Transfer of patient records from a hand-held medical-data capture-device 104, multiple hand-held medical-data capture-devices 104 up to 10, to a third party EMR capture system and to the EMR capture system 100, respectively in that order.

Limited user interface for status review of known hand-held medical-data capture-device 104.

Configuration update control for detected devices providing configuration of:
Hospital reference
Unit location reference Extended Operational Features and Implementation Capability The following extended features are supported in extended operational features and implementation capability:

1. A Patient Record Information and measurement display interface for use without an EMR capture system 100.
2. Update of device firmware over the wireless network.

Operational Use

Local Network Based—Single Client

In some implementations, the hand-held medical-data capture-device 104 is deployed to a local hospital, or other location, wireless IT network that supports WI-FI enabled devices. The hand-held medical-data capture-device 104 supports all local network policy's including any local security policy/protocols, such as WEP, WPA, WPA2, WPA-EPA as part of the connection process for joining the network. In some implementations, the hand-held medical-data capture-device 104 operates on both physical and virtual wireless LAN's, WAN's, and the hand-held medical-data capture-device 104 is configured for operation on a specific segment of the network. Depending on the IT network structure, when the hand-held medical-data capture-device 104 is configured for operation on a specific segment of the network, the hand-held medical-data capture-devices 104 network connection ability is limited to the areas of the operational environment for which it as be configured. Therefore, the hand-held medical-data capture-device 104 in network environments that have different network configurations is configured to ensure that when the hand-held medical-data capture-device 104 is used in various locations throughout the environment that the hand-held medical-data capture-device 104 has access in all required areas.

In some implementations, the bridge 102 system is located on the same IT network and deployed in accordance with all local IT requirements and policy's and that the hand-held medical-data capture-devices 104 on this network are able to determine a routable path to the bridge 102. The hand-held medical-data capture-devices 104 and the server are not required to implement any network level discovery protocols and therefore the bridge 102 is required to be allocated static IP address on the network. In the case where a secondary bridge 102 device is deployed to the network as a backup for the primary, or the bridge 102 supports a dual networking interface capability, then the secondary bridge 102 IP address is also required to be allocated a static IP address. It is important that the static IP primary and secondary address, if supported, remain constant to ensure proper and continuous system operation. When the IP address of the bridge 102 is changed then all devices configured with the old IP address are then unable to find the bridge 102 device on the network and the hand-held medical-data capture-devices 104 is manually reconfigured for operation.

A benefit of this bridge 102 implementation to the local IT network infrastructure is the reduction in latency times for data sent between the hand-held medical-data capture-devices 104 and the bridge 102.

It is important to note that this is a single organization implementation and as such the bridge 102 is configured to meet the security and access requirements of a single organization.

Figure 2:
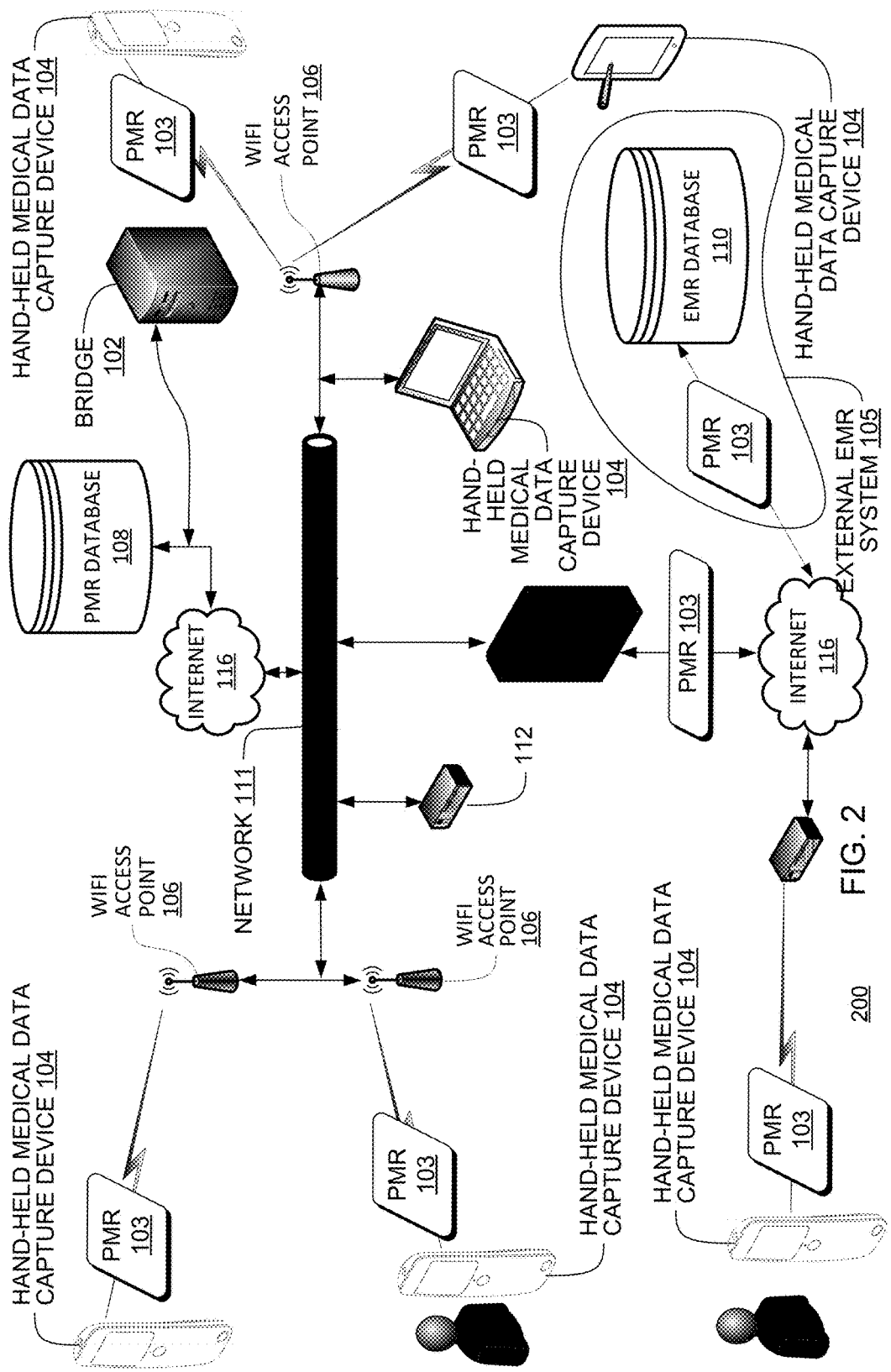
FIG. 2 is a block diagram of an overview of an EMR capture system having a remote cloud based bridge, according to an implementation.

FIG. 2 is a block diagram of an overview of an electronic medical records (EMR) capture system 200 having a remote cloud based bridge 102, according to an implementation.

An implementation of a remote cloud-based bridge 102 for a single client is similar to the local network case described at the end of the description of FIG. 1, with the exception that the bridge 102 is not physically located at the physical site of the hand-held medical-data capture-devices 104. The site, such as a hospital, has deployed the bridge 102 to a remote site, their specific IT center or on a Cloud-based PMR storage system 105.

The physical locale of the bridge 102 is transparent to the hand-held medical-data capture-device 104. However in some implementations data latency between the bridge 102 and the hand-held medical-data capture-devices 104 on the hand-held medical-data capture-device 104 is too large to provide a positive user experience.

Again as in the local install case, the same user access and security policies are in place for the single operating organization.

Remote Based—Multiple Client Support

In some implementations, for smaller organizations or for organizations that do not have a supporting IT infrastructure or capability that a remote bridge 102 system is deployed to support more than one organization. Where the remote bridge 102 system is deployed to support more than one organization, the bridge 102, or servers, can be hosted as a cloud based system. In this case the hand-held medical-data capture-devices 104 are located at the operational site for the supported different geographical location organizations and tied to the bridge 102 via standard networking methods via either private or public infrastructure, or a combination thereof.

Where a remote, i.e. non-local IT network, system is deployed to support more than one hospital or other organization EMR capture system 100 includes components that isolate each of the supported organizations security and user access policy's and methods along with isolating all data transfers and supporting each organizations data privacy requirements. In addition, system performance is required to be balanced evenly across all organizations. In this case each organization can require their specific EMR capture system 100 be used, their EMR capture system 100 will have to be concurrently operational with many diverse EMR capture systems 100.

Single Measurement Update

The primary function of the hand-held medical-data capture-device 104 is to take a patient temperature, display the result to the operator and to save the patient information and temperature to an EMR capture system 100 via the bridge 102.

Normally the hand-held medical-data capture-device 104 is in a low power state simply waiting for an operator to activate the unit for a patient measurement. Once activated by the operator EMR capture system 100 will power up and under normal operating conditions guide the operator through the process of patient temperature measurement and transmission of the patient record to the bridge 102 for saving to the EMR capture system 100.

Confirmation at each stage of the process to the operator is required, i.e. data is valid, to ensure a valid identified patient result is obtained and saved to the EMR, the key confirmation point is: Saving of data to EMR/Bridge 102

In some implementations, the confirmation at each stage in some implementations is provided by either the bridge 102 device or the EMR capture system 100.

When confirmation is provided by the bridge 102 it is an acknowledgment to the hand-held medical-data capture-device 104 that the bridge 102 has accepted the information for transfer to the EMR capture system 100(s) in a timely manner and is now responsible for the correct management and transfer of that data.

When confirmation is provided by the EMR capture system(s) 100, the bridge 102 is the mechanism via which the confirmation is returned to the hand-held medical-data capture-device 104. That is the hand-held medical-data capture-device 104 sends the data to the bridge 102 and then waits for the bridge 102 to send the data to the EMR and for the EMR to respond to the bridge 102 and then the bridge 102 to the hand-held medical-data capture-device 104, In some implementations, depending on the operational network and where the bridge 102 is physically located, i.e. local or remote, that the type of confirmation is configurable. For a remote located bridge 102 the latency time involved in the EMR level confirmation can be deem too long for an acceptable user experience.

In the event that the hand-held medical-data capture-device 104 cannot join the network or the bridge 102 device cannot be communicated with or the bridge 102 or EMR capture system 100(s) level confirmation is not received the hand-held medical-data capture-device 104 will maintain an internal non-volatile storage mechanism for unsaved patient records. It is not acceptable for the hand-held medical-data capture-device 104 to simply not provide its primary clinical purpose in light of these possible operational issue. If the hand-held medical-data capture-device 104 has saved records present in its internal memory then the hand-held medical-data capture-device 104 will in a timely automatic manner attempt to transfer the saved records to the bridge 102 for processing.

Heartbeat

The hand-held medical-data capture-devices 104 in order to obtain date/time, configuration setting, provide status information to the bridge 102, transfer saved patient records and check for a firmware update will provide a mechanism to on a configured interval automatically power up and communicate to the configured bridge 102 without operator intervention.

Accordingly, the and outside of the normal clinical use activation for the hand-held medical-data capture-device 104, the hand-held medical-data capture-device 104 can both update its internal settings, and provide status information to the bridge 102 system.

If these actions where left to only the operator startup case of the hand-held medical-data capture-device 104 for operational clinical use then there is an unacceptable delay to the operator in proceeding to the measurement action of the hand-held medical-data capture-device 104. This is deemed acceptable and the hand-held medical-data capture-device 104 in some implementations make best efforts to maintain its operational status independent of the clinical use case.

Automatic Transfer of Saved Patient Measurement Records (PMRs)

If the hand-held medical-data capture-device 104 for an unknown reason has been unable to either join the network or connect to the bridge 102 or receive a bridge 102 or EMR capture system 100(s) level acknowledge that data has been saved the hand-held medical-data capture-device 104 will still allow the primary clinical temperature measurement function to be carried out and will save the resultant PMR in non-volatile internal memory up to a supported, configured, maximum number of saved patient records on the hand-held medical-data capture-device 104.

When the hand-held medical-data capture-device 104 is started for a measurement action the hand-held medical-data capture-device 104 will determine if it contains any saved patient records in its internal memory. If one or more saved patient records are detected then the hand-held medical-data capture-device 104 will attempt to join the network immediately, connect to the bridge 102 and send the patient records one at a time to the bridge 102 device while waiting for the required confirmation that the bridge 102 has accepted the patient record. Note in this case confirmation from the EMR capture system 100 is not required. On receipt of the required validation response from the remote system the hand-held medical-data capture-device 104 will delete the patient record from its internal memory. Any saved patient record that is not confirmed as being accepted by the remote device is maintained in the hand-held medical-data capture-devices 104 internal memory for a transfer attempt on the next power up of the hand-held medical-data capture-device 104

The hand-held medical-data capture-device 104 on the heart beat interval all also carry out this function. In some implementations, the hand-held medical-data capture-device 104 will reduce its heart beat interval when saved patient records are present on the hand-held medical-data capture-device 104 in order to ensure that the records are transferred to the bridge 102, EMR, in a timely manner once the issue has been resolved. When this transfer mechanism is active status information is presented to the operator on the hand-held medical-data capture-device 104 screen.

Under this operation it is possible for the bridge 102 device to receive from a single hand-held medical-data capture-device 104 multiple patient record transfer requests in rapid sequence.

Device Configuration

The hand-held medical-data capture-device 104 on connection to the bridge 102, heart beat interval or operator activated, will provide the bridge 102 with its model number and all appropriate revisions numbers and unique identification to allow the bridge 102 to determine the hand-held medical-data capture-device 104 capabilities and specific configurations for that device.

The hand-held medical-data capture-device 104 will query the bridge 102 for its device parameters and if different from the hand-held medical-data capture-devices 104 current setting update the hand-held medical-data capture-devices 104 setting to the new setting value as provided by the bridge 102.

Accordingly, in some implementations the bridge 102 will act as the central repository for device configuration, either for a single device, a group of defined devices or an entire model range.

Device Date/Time Update

In implementations where there is no mechanism on the hand-held medical-data capture-device(s) 104 for the user to configure date and time on the hand-held medical-data capture-device 104 via its user interface.

All embedded systems with a real time clock function, RTC, will drift with time due to the accuracy of their specific RTC hardware, ambient and operational temperature.

It is therefore expected that each device on connection to the bridge 102 will query the bridge 102 for the current date and time and update the hand-held medical-data capture-devices 104 internal RTC clock based on the provided information.

The hand-held medical-data capture-devices 104 will query the bridge 102 on the defined heart beat interval or when they are started by the operator upon joining the network.

The bridge 102 is therefore expected to support an accurate date and time mechanism, with leap year capability, as per the local IT policy. If no local IT policy is in place then the bridge 102 is to maintain date and time against a known accurate source, e.g. a web based time server.

Accordingly, in some implementations all devices is maintained at the same date and time across the operation of EMR capture system 100 and the capabilities of the hand-held medical-data capture-devices 104.

Device Status Management

In some implementations, the bridge 102 provides a level of device management for the hand-held medical-data capture-devices 104 being used with EMR capture system 100. In some implementations, the bridge 102 is able to report and determine at least the following:

- Group and sort devices by manufacture, device model, revisions information and display devices serial numbers, unique device ID, asset number, revisions, etc. and any other localized identification information configured into the hand-held medical-data capture-device 104, e.g. ward location reference or Hospital reference
- The last time a specific unit connected to EMR capture system 100
- The current status of the a given device, battery level, last error, last date of re-calibration of check, or any other health indicator supported by the hand-held medical-data capture-device 104.
- Report devices out of their calibration period, or approaching their calibration check
- Report devices that require their internal battery replaced
- Report devices that require re-checking due to a detected device failure or error condition, or that have been treat in a harsh manner or dropped.
- Determine if a hand-held medical-data capture-device 104 has not connected for a period of time and identify the hand-held medical-data capture-device 104 as lost or stolen. If the hand-held medical-data capture-device 104 reconnects to the network after this period of time then the hand-held medical-data capture-device 104 in some implementations is highlighted as requiring an accuracy check to ensure that it is operational. Note the hand-held medical-data capture-devices 104 will likely also support this capability and after a pre-determined time disconnected from the network inhibit their measurement function until a hand-held medical-data capture-device 104 level recheck is carried out
- Provide a mechanism to commission and decommission devices onto and off of the network. If a hand-held medical-data capture-device 104 has not been specifically commissioned for operation on the network then it in some implementations is not be allowed to access the core services supported by the bridge 102 even if it has configured for operation on the EMR capture system 100

Firmware Update

In some implementations, a firmware update for a given device model is scheduled on the network as opposed to simply occurring. It is considered unacceptable if a hand-held medical-data capture-device 104 is activated for a patient measurement and then carries out a firmware update, this delays the patient vital sign measurement.

Instead the bridge 102 system will support a firmware update roll out mechanism where the date and time of the update can be scheduled and the number of devices being updated concurrently can be controlled.

In some implementations, when a hand-held medical-data capture-device 104 connects to the bridge 102 due to a heartbeat event that the hand-held medical-data capture-device 104 will query the bridge 102 to determine if the firmware update for that model of device is available and verify if its firmware, via revision number, is required to be updated. The bridge 102 will respond to the hand-held medical-data capture-device 104 based on if a firmware update is available and the defined schedule for the update process.

If there is an update available but the current time and date is not valid for the schedule then the bridge 102 will information the hand-held medical-data capture-device 104 that there is an update but that the update process is delayed and update the hand-held medical-data capture-devices 104 firmware check interval configuration. The firmware check interval setting will then be used by the hand-held medical-data capture-device 104 to reconnect to the bridge 102 on a faster interval than the heartbeat interval in order to facilitate a more rapid update. For e.g. the firmware update schedule on the bridge 102 in some implementations is for every night between 2 pm and 4 pm, the interval timer in some implementations will then be set to for example, every 15 minutes as opposed to a heartbeat time interval of, for example, every 24 hours.

The hand-held medical-data capture-device 104 if the firmware check interval is non-zero will then on the firmware check interval connect to the bridge 102 and retest for the firmware update to be carried out. Once the hand-held medical-data capture-device 104 has connected to the bridge 102 for the updated and the schedule date and time are valid, along with the concurrent number of devices being updated, the hand-held medical-data capture-devices 104 firmware update procedure is followed, the hand-held medical-data capture-devices 104 firmware updated and EMR capture system 100 verified for normal operational use. As part of the firmware update procedure the hand-held medical-data capture-devices 104 firmware check internal is reset back to 0 or done so by the hand-held medical-data capture-device 104 on the next active condition to the bridge 102.

In some implementations, the bridge 102 will manage the firmware update process for many different hand-held medical-data capture-devices 104 each with their specific update procedure, update file formats, and verification methods and from a date and time scheduling mechanism and the number of devices being update concurrently. In addition, in some implementations the bridge 102 will provide a mechanism to manage and validate the firmware update files maintain on the bridge 102 for use with the hand-held medical-data capture-devices 104.

This section concludes with short notes below on a number of different aspect of the EMR data capture system 100 and 200 follow on numerous topics:

Remote—single client: The bridge 102 architecture and implementation in some implementations cater for remote operation on a hospital network system. Remote operation is seen as external to the network infrastructure that the hand-held medical-data capture-devices 104 are operational on but considered to be still on the organizations network architecture. This can be the case where a multiple hospital-single organization group has deployed EMR capture system 100 but one bridge 102 device services all hospital locations and the bridge 102 is located at one of the hospital sites or their IT center.

Remote—multiple client support: The bridge 102 architecture and implementation in some implementations is limited to remote operation on a cloud based server that supports full functionality for more than one individual separate client concurrently. Where we deploy a cloud based single or multiple server system to service 1 or more individual hospital/clinical organization. The IT system and security requirements for each client in some implementations be meet in this case, different organizations will have different interface requirements.

Multiple concurrent EMR support: For a single remote bridge 102 servicing multiple clients EMR capture system 100 supports interfacing to an independent EMR, and different EMR vendor, concurrently for each support client. With one bridge 102 servicing multiple clients each client can/will require the patient measurements to be sent to a different EMR capture system 100. These EMR capture system(s) 100 will in all likelihood be provided by different vendors.

Single organization device support: The bridge 102 supports at least 10000+ hand-held medical-data capture-devices 104 for a single client for either local or remote implementation. Note the supported hand-held medical-data capture-devices 104 may be from diverse hand-held medical-data capture-device 104 manufacturers.

Support Different EMR for same client: The bridge 102 architecture for operation in a single client organization supports the user by the organization of different EMR capture system(s) 100 from different departments of wards in the operational environment. It is not uncommon for a single organization to support multiple different EMR capture system(s) 100 for different operational environments, for example, Cardiology and ER. EMR capture system 100 in some implementations takes this into account and routes the patient data to the correct EMR capture system 100. Therefore the bridge 102 is informed for a given hand-held medical-data capture-device 104 which indicates to the EMR the medical data has to be routed to.

Segregation of operations for multiple client operations on single bridge 102:

EMR capture system 100 supports per client interfaces and functionality to ensure that each client's configurations, performance, user accounts, security, privacy and data protection are maintained. For single server implementations that service multiple independent hospital groups the bridge 102 in some implementations maintain all functionality, and performance per client separately and ensure that separate user accounts, bridge 102 configuration, device operation, patient and non-patient data, ERM interfaces etc. are handled and isolated per client. A multiple cloud based implementation in this case will obviate this function as each client includes their own cloud based system, but this is at a higher cost.

Multiple organization device support: The bridge 102 supports at least 1 million+ hand-held medical-data capture-devices 104 for remote implementations that services multiple separate hospital systems. The supported hand-held medical-data capture-devices 104 can be from different hand-held medical-data capture-device 104 manufacturers.

EMR capture system support: The hand-held medical-data capture-device 104 supports a wide range of EMR capture system(s) 100 and is capable of interfacing to any commercially deployed EMR capture system 100.

EMR capture system interface and approvals: The bridge 102 device provides support for all required communication, encryption, security protocols and data formats to support the transfer of PMR information in accordance with all required operational, standards and approval bodies for EMR capture system(s) 100 supported by the EMR capture system 100.

Remote EMR capture system(s): The bridge 102 supports interfacing to the required EMRs systems independent of the EMR capture system(s) 100 location, either locally on the same network infrastructure or external to the network that the bridge 102 is resided on or a combination of both. The EMR capture system 100, or systems, that the bridge 102 is required to interact with and save the patient to can not be located on the same network or bridge 102 implementation location, therefore the bridge 102 implementation in some implementations ensure that the route to the EMR exists, and is reliable.

Bridge buffering of device patient records: The bridge 102 device provides a mechanism to buffer received PMRs from connected hand-held medical-data capture-devices 104 in the event of a communications failure to the EMR capture system 100, and when communications has been reestablished subsequently transfer the buffered measurement records to the EMR. It is expected from time to time in normal operation that the network connection from the bridge 102 to the configured EMR capture system 100 is lost. If communications has been lost to the configured EMR capture system(s) 100 then the bridge 102 in some implementations accepts measurement records from the hand-held medical-data capture-devices 104 and buffers the measurement records until communications has be reestablished. Buffering the measurement records allows the medical facility to transfer the current data of the medical facility to the bridge 102 for secure subsequent processing. In this event the bridge 102 will respond to the hand-held medical-data capture-device 104 that either 1. Dynamic validation of EMR acceptance is not possible, or 2. The bridge 102 has accepted the data correctly.

Bridge 102 real time acknowledge of EMR save to device: The bridge 102 provides a mechanism to pass to the hand-held medical-data capture-device 104 confirmation that the EMR has accepted and saved the PMR. The bridge 102 when configured to provide the hand-held medical-data capture-device 104 with real time confirmation that the EMR capture system 100($s$) have accepted and validated the PMR. This is a configuration option supported by the bridge 102.

Bridge 102 real time acknowledgement of acceptance of device PMR: The bridge 102 provides a mechanism to pass to the hand-held medical-data capture-device 104 confirmation that the bridge 102 has accepted the PMR for subsequent processing to the EMR. The hand-held medical-data capture-device 104 in some implementations verifies that the bridge 102 has accepted the PMR and informs the operator of the hand-held medical-data capture-device 104 that the data is secure. This level of confirmation to the hand-held medical-data capture-device 104 is considered the minimum level acceptable for use by the EMR capture system 100. Real time acknowledgement by the bridge 102 of acceptance of the PMR from the device is a configuration option supported by the bridge 102.

Bridge Date and Time: The bridge 102 maintains internal date and time against the local network time source or a source recommended by the IT staff for the network. All transitions and logging events in some implementations are time stamped in the logs of the bridge 102. The hand-held medical-data capture-device 104 will query the bridge 102 for the current date and time to update its internal RTC. The internal time of hand-held medical-data capture-device 104 can be maintained to a +/−1 second accuracy level, although there is no requirement to maintain time on the hand-held medical-data capture-device 104 to sub one-second intervals.

Graphical User Interface: The bridge 102 device provides a graphical user interface to present system information to the operator, or operators of EMR capture system 100. The user interface presented to the user for interaction with EMR capture system 100 in some implementations be graphical in nature and use modern user interface practices, controls and methods that are common use on other systems of this type. Command line or shell interfaces are not acceptable for operator use though can be provided for use by system admin staff.

Logging and log management: The bridge 102 is required to provide a logging capability that logs all actions carried out on the bridge 102 and provides a user interface to manage the logging information. Standard logging facilities are acceptable for this function for all server and user actions. Advanced logging of all device communications and data transfers in some implementations is also provided, that can be enabled/disable per hand-held medical-data capture-device or for product range of hand-held medical-data capture-devices.

User Accounts: The bridge 102 device provides a mechanism to support user accounts on the hand-held medical-data capture-device 104 for access control purposes. Standard methods for user access control are acceptable that complies with the operational requirements for the install/implementation site.

User Access Control: The bridge 102 device supports multiple user access control that defines the access control privileges for each type of user. Multiple accounts of each supported account type are to be support. Access to EMR capture system 100 in some implementations be controlled at a functional level. In some implementations, the following levels of access is provided:

- System Admin: provides access to all features and functions of EMR capture system 100, server and device based.
- Device Admin: provides access only to all device related features and functions supported by the EMR capture system 100.
- Device Operator: provides access only to device commissioning, and configuration.
- Device Installer: provides access only to device commissioning and test capabilities.
- A user account can be configured for permissions for one or more account types.

Multi-User Support: The bridge 102 device is required to provide concurrent multi-user support for access and management of the bridge 102 system across all functions. Providing multiple user access is deemed a necessary operational feature to support.

Modify User Accounts: The bridge 102 provides a method to create, delete, and edit the supported user accounts and supported access privileges per account.

Bridge Data Corruption/Recovery: The bridge 102 architecture and implementation in some implementations ensure that under a catastrophic failure of EMR capture system 100 or a storage component that no data is lost that has not been confirmed as saved to the either the EMR for PMRs or localize storage for operational data pertaining to the non-patient data maintained by the EMR capture system 100. The bridge 102 supports a method to ensure zero data lost under critical and catastrophic system failure of the bridge 102 or any of the bridge 102 components, network interfaces, storage systems, memory contents, etc. for any data handled by the EMR capture system 100. In the event of a recovery action where a catastrophic failure has occurred EMR capture system 100 supports both the recovery action and its normal operational activities to ensure that EMR capture system 100 is active for clinical use.

Bridge availability: The bridge 102 device is a high availably system for fail safe operation 24/7/365, with 99.99% availability, i.e. "four nines" system. The bridge 102 implementation is expected to meet an availability metric of 99.99%, i.e. a "four nines" system because the bridge 102 hardware in some implementations is implemented with a redundant dual server configuration to handle single fault conditions. The bridge 102 is required to have an independent power source or if the installation site has a policy for power loss operation the bridge 102 installation in some implementations comply with the policy requirements.

Bridge 102 Static IP address and port Number: The bridge 102 provides a mechanism to configure the bridge 102 for a primary use static IP address and port number. For hand-held medical-data capture-device 104 connection to the bridge 102, the bridge 102 in some implementations have a static IP address and that IP address in some implementations be known by the hand-held medical-data capture-device 104. Bridge 102 Dual network capability: The bridge 102 system provides a mechanism to support a dual operational network interface to allow for failure of the primary network interface. This secondary network interface is required to support a configurable static IP address and port number. A redundant network connection in some implementations be provided to cover the event that the primary network interface has failed. Note if the bridge 102 implementation for EMR capture system 100 employs two separate bridges 102 or other redundant mechanism to provide a backup system then this requirement can be relaxed from an operational view point, however EMR capture system 100 in some implementations support this mechanism.

Local WIFI commissioning network: The bridge 102 provides a mechanism on the local operational network to commission new hand-held medical-data capture-devices 104 for operational use. EMR capture system 100 is to supply a localized isolated network for the use of commissioning new devices onto the operational network. The bridge 102 is to have a known default IP address on this network and provide a DHCP server for the allocation of IP address to devices on EMR capture system 100. The commissioning of new devices is to be considered a core aspect of the bridge 102 functions. However it is acceptable that a separate non server based application in some implementations will manage the configuration process provided the same user interface is presented to the user and the same device level configuration options are provided. In some implementations, the configuration of a new hand-held medical-data capture-device 104 on the network is carried out in two stages: Stage 1: network configuration from the commissioning network to the operational network Stage 2: Once joined on the operational network specific configuration of the hand-held medical-data capture-device 104 for clinical/system function operation.

Remote commissioning of devices: EMR capture system 100 provides a mechanism where the bridge 102 device is not present on the local network for a new device is to be commissioned on the operational network. Even when the bridge 102 is on a cloud server external to the operational site network new devices in some implementations be commissioned onto the network in the same manner as if the bridge 102 was a local server. This does not preclude the installation of a commission relay server on to the operational network that supports this mechanism.

Device setup: The bridge 102 supports the configuration of a device level network operation and security settings for an existing or new hand-held medical-data capture-device 104 on either the commissioning network or the operational network. New devices are configured on the commissioning network. Existing devices on the operational network are also to be configurable for network and security requirements. Independent of the network that the hand-held medical-data capture-device 104 is currently connected to the bridge 102 provides the required user interface for the configuration of the network operational and security settings by the operator. Once configured, a method of verifying that the hand-held medical-data capture-device 104 has been configured correctly but be presented to the operator to prove that the hand-held medical-data capture-device 104 is operational. Devices are expected support a network command to reboot and rejoin the network for this verification purpose.

Bridge Configuration: The bridge provides a mechanism to support configuration of all required bridge 102 specific control options. A method to configure the bridge 102 functions in some implementations is provided for all features where a configuration option enable, disable or a range of parameters are required.

Bridge Hand-held medical-data capture-device acknowledgement method: The bridge 102 provides a configuration method to control the type of ACK required to be supported by the EMR capture system 100, one of: Device configuration dependent, EMR level ack, Bridge 102 level ack. In some implementations, A hand-held medical-data capture-device 104 requires from the bridge 102 an acknowledgement that the PMR has been saved by the EMR capture system 100 or accepted for processing by the bridge 102.

EMR Level: Bridge 102 confirms save by EMR capture system 100.

Bridge Level: bridge 102 controlled, accepted for processing by the bridge 102.

Enabled/Disable of firmware updated mechanism: The bridge 102 provides a method to globally enable or disable the supported hand-held medical-data capture-device 104 firmware updated feature. A global enable/disable allows the control of the firmware update process.

Server Management: The bridge 102 is required to provide a user interface that provides configuration and performance monitoring of the bridge 102 and platform functions.

System Reporting: The bridge 102 provides a mechanism to provide standard reports to the operator on all capabilities of the bridge 102 system. Standard reporting in some implementations includes selection of report parameters, sorting of report parameters, printing of reports, export of reports to known formats, WORD, excel, PDF etc., identification of reports, organization name, location, page numbers, name of report etc., date and time of log, generate by user type and extent of, provides full reporting for all system features and logs. Examples are: list of devices known to EMR capture system 100, with location reference and date and time of last connection, report on the battery status for all known hand-held medical-data capture-devices 104, report on any devices that reported an error, report on devices that have expired calibration dates, and report on devices that are approaching calibration dates.

Demo Patient Interface: The bridge 102 provides a mechanism for demo only purposed where an EMR capture system 100 is not available for interfacing to EMR capture system 100 to allow patient records received from a given device to be viewed and the vital sign data presented. For demonstrations of EMR capture system 100 where there is no EMR capture system 100 to connect the bridge 102 system to provides a user interface method to present the data sent to the bridge 102 by the connected hand-held medical-data capture-devices 104. In some implementations, this patient data interface manages and stores multiple patients and multiple record readings per patient and present the information to the operator in an understandable and consistent manner.

Interface to PMR database: The bridge 102 device provides an interface to the PMR database 108 system for the purpose of storing anonymous patient records and device specific status information. Anonymous PMRs are stored for the purposes of data analysis as well as provide a mechanism to monitor the operation of the hand-held medical-data capture-devices 104.

Device PMRs: The bridge 102 in some implementations accepts propriety formatted measurement records from hand-held medical-data capture-devices 104 connected and configured to communicate with the bridge 102 and translate the received measurement record into a suitable format for transfer to a EMR capture system 100. The bridge 102 is the hand-held medical-data capture-device 104 that will take the hand-held medical-data capture-device 104 based data and translate that data into a format suitable to pass along to a local or remote EMR system using the required protocols of that EMR capture system 100.

Device non patient measurement data: The bridge 102 in some implementations accept meta data from connected hand-held medical-data capture-devices 104 and provide meta data to a connected device. Meta data is any other data or setting parameter associated with the hand-held medical-data capture-device 104 that in some implementations is managed by the bridge 102, e.g. device configuration settings, firmware images, status information etc.

Device to Bridge 102 interface protocol: The bridge 102 supports a hand-held medical-data capture-device 104 to bridge 102 interface protocol, BRIP, for all communications between the hand-held medical-data capture-devices 104 and the bridge 102 device. Each device supports a single interface protocol, BRIF, but it in some implementations this can be impracticable and individual device or manufacture level protocols can have to be supported by the bridge 102, the bridge 102 architecture is therefore required to take this into account.

Network communications method: The bridge 102 is required to support a LAN based interface for processing connection requests and data transfers from remote hand-held medical-data capture-device 104. Standard communications methods such as UDP/TCP/HTTP etc. are supported, including TCP/IP sockets, but the interface is not restricted to this transfer mechanism, the architecture of EMR capture system 100 in some implementations support other transfer methods such as UDP, HTTP, web servers. Where more than one hand-held medical-data capture-device 104 type is supported in EMR capture system 100 the bridge 102 is required to support different transfer mechanism concurrently Hand-held medical-data capture-devices 104: The bridge 102 in some implementations accept connections and measurement data records from hand-held medical-data capture-device(s) 104.

Thermometer devices: The first hand-held medical-data capture-devices 104 to be supported by the EMR capture system 100 are to hand-held medical-data capture-device(s) 104.

Non-conforming Hand-held medical-data capture-devices: The bridge 102 in some implementations accepts connections and measurement data records from non-hand-held medical-data capture-device(s) 104 hand-held medical-data capture-devices 104 using device interface protocols specific to a given device or manufacture of a range of device. The EMR capture system 100 supports third party hand-held medical-data capture-devices 104 to provide the same core features and functions as those outlined in this document. In some implementations, a core system supports all hand-held medical-data capture-devices 104 connected to EMR capture system 100, for the purposes of measurement data, temperature, ECG, blood pressure, plus other vital signs, both single and continuous measurement based, for transfer to the selected EMR capture system 100, along with per device configuration and status monitoring.

Single Parameter Measurement Data: The bridge 102 in some implementations accept and processes for transfer to the configured EMR capture system 100, single event measurement data. Single event measurement data is defined as a patient vital sign single point measurement such as a patient temperature, blood pressure, heart rate or other data that is considered a one-time measurement event for a single measurement parameter. This type of data is generated from a hand-held medical-data capture-device 104 that supports a single vital sign.

Multiple Parameter Measurement Data: The bridge 102 in some implementations accept and process for transfer to the EMR multiple event measurement data. Multiple event measurement data is defined as a patient vital sign single point measurement such as a patient temperature, blood pressure, heart rate or other parameter that is considered a one-time measurement event for more than one parameter. This type of data is generated from a multi-vital sign hand-held medical-data capture-device 104.

Continuous Parameter Measurement Data: The bridge 102 in some implementations accept and process for transfer to the EMR single parameter continuous measurement data. Continuous measurement data is defined as a stream of measurement samples representing a time domain signal for a single vital sign parameter.

Unique Hand-held medical-data capture-device ID: The bridge 102 supports a unique identifier per hand-held medical-data capture-device 104, across all vendors and device types, for the purposes of device identification, reporting and operations. Each hand-held medical-data capture-device 104 that is supported by the EMR capture system 100 provides a unique ID based on the manufacture, product type, and serial number or other factors such as the FDA UID. The bridge 102 is required to track, take account of, and report this number in all interactions with the hand-held medical-data capture-device 104 and for logging. This device ID can also be used in the authentication process when a hand-held medical-data capture-device 104 connects to the bridge 102.

Device connection authentication: The bridge 102 provides a mechanism to authenticate a given hand-held medical-data capture-device 104 on connection to ensure that the hand-held medical-data capture-device 104 is known and allowed to transfer information to the bridge 102. Access to the bridge 102 functions in some implementations be controlled in order to restrict access to currently allowed devices only. Acceptance of a hand-held medical-data capture-device 104 making connection the bridge 102 for 2 main rationales. 1. the hand-held medical-data capture-device 104 is known to the bridge 102, and that 2. a management function to control access for a given device, i.e. allow or bar access.

Device date and time update: The bridge 102 device can provide a mechanism to allow a connected hand-held medical-data capture-device 104 to update its internal date and time settings against the bridge 102's current date and time. The hand-held medical-data capture-devices 104 are to update their internal real time clocks on connection to the bridge 102, accordingly, a time reference across all devices used with EMR capture system 100 is obtained from a central source. All embedded systems real time clock functions drift with time and operational and ambient temperature, this mechanism will form the basis of both time and date configuration on the hand-held medical-data capture-device 104 and dynamic update of time and date for the hand-held medical-data capture-device 104 thereby removing the need to set time and date on a given device. An accuracy of +/−1 second is acceptable for maintaining the time on a hand-held medical-data capture-device 104. Bridge 102 to device backwards compatibility: The bridge 102 device is required to be backwards compatible with all released versions of hand-held medical-data capture-device 104 firmware, interface protocols, and data formats supported by the bridge 102 device from first release of the bridge 102 system. Backwards compatibly of the bridge 102 with all released revisions of hand-held medical-data capture-device 104 is a in some implementations for the normal operation of EMR capture system 100. It cannot be guarantee that all devices of a given product are at the same revision level or that different products from a single manufacture or from different manufactures will support the same interface protocol or other critical component revision.

Last connection of device: The bridge 102 is required maintain a history of the connection dates and times for a given hand-held medical-data capture-device 104. This is required from a reporting and logging viewpoint. In some implementations, will also be used to determine if a hand-held medical-data capture-device 104 is lost/stolen or failed.

Calibration/Checker Monitoring: The bridge 102 is required to track the valid calibration dates for a given device and present to the operator does devices that are out of calibration or approaching calibration All hand-held medical-data capture-devices 104 in some implementations be checked for operation and accuracy on a regular bases. EMR capture system 100 can provide the facility to generate a report and high light devices that are either out of calibration and those approaching calibration. The check carried out by the bridge 102 is on the expiry date exposed by the hand-held medical-data capture-device 104. The bridge 102 is not required to actually check the hand-held medical-data capture-device 104 for calibration, only report if the hand-held medical-data capture-device 104 is out of calibration based on the hand-held medical-data capture-devices 104 expiry date. In some implementations, the expiry date is updated at the time of the hand-held medical-data capture-device 104 recalibration check.

Error/Issue monitoring: The bridge 102 is required to track the issues/errors reported by a given device and present that information to the operator in terms of a system report. Reporting of device level errors dynamically for a given device is diagnostics tool for system management. Providing the issue/error history for a given device will provide core system diagnostic information for the hand-held medical-data capture-device 104.

Battery Life monitoring: The bridge 102 is required to track the battery level of a given device and report the that information to the operator. EMR capture system 100 is to highlight to the operator that a given device has an expired or nearly expired or failed internal battery based on the information exposed by the hand-held medical-data capture-device 104. It is the hand-held medical-data capture-devices 104 responsibility to determine its own internal power source charge level or battery condition. The bridge 102 can provide a mechanism to report the known battery condition for all devices, e.g. say all devices that have 10% battery level remaining.

Lost/Stolen/Failed monitoring: The bridge 102 is required to determine for a given hand-held medical-data capture-device 104 if it has been lost/stolen/or failed and disable the hand-held medical-data capture-device 104 for system operation. Being able to determine if a system has not connected to the bridge 102 for a period of time is a feature for failed, lost or stolen reporting to the operator. If a hand-held medical-data capture-device 104 has not connected to EMR capture system 100 for a period of time, EMR capture system 100 determines that the hand-held medical-data capture-device 104 has been stolen or lost, in this event the operator is informed in terms of a system report and the hand-held medical-data capture-device 104 removed from the supported devices list. If and when the hand-held medical-data capture-device 104 reconnects to EMR capture system 100 the hand-held medical-data capture-device 104 is to be lighted as "detected" and forced to be rechecked and re-commissioned again for use on the network.

Device Keep Alive: The bridge 102 provides a mechanism to inform a target hand-held medical-data capture-device 104 upon connection to the bridge 102 to stay connected to the bridge 102 until released by the bridge 102. A hand-held medical-data capture-device 104 keep alive method in some implementations is provided so that the bridge 102 when a hand-held medical-data capture-device 104 connects can inform the hand-held medical-data capture-device 104 to stay powered and connected to the bridge 102 for the purposes of reconfiguration, status monitoring or diagnostics.

Reset device to network default: A method to reset a target device or group of selected devices to factory settings for all network parameters in some implementations be supported.

Reset device to factory default: A method to reset a target device or group of selected devices to their factory default settings in some implementations is supported.

Dynamic Device Parameter Configuration: The bridge 102 provides a mechanism to provide configuration information to a hand-held medical-data capture-device 104 when requested by the hand-held medical-data capture-device 104 on connection to the bridge 102 or via the keep device alive mechanism. Upon connecting to a bridge 102 a hand-held medical-data capture-device 104 as part of the communications protocol will determine if its current configuration is out of date, if any aspect of the hand-held medical-data capture-devices 104 configuration is out of date and is required to be updated then the bridge 102 provides the current configuration information for the hand-held medical-data capture-device 104 model and revision This is intended to be as simple as the hand-held medical-data capture-device 104 getting the configuration setting for each of its supported parameters. the bridge 102 is responsible to ensure that the supplied information is correct for the hand-held medical-data capture-device 104 model and revision level.

Device Configuration Grouping: Single device: The bridge 102 provides a mechanism to configure a single device, based on unique device id, to known configuration parameters. The bridge 102 in some implementations allows a single hand-held medical-data capture-device 104 to be updated when it connects to the bridge 102 either via the heart beat method or via operator use. This effectively means that the bridge 102 provides a method to manage and maintain individual device configuration settings and have those settings available dynamically for when the hand-held medical-data capture-device 104 connects. Further the bridge 102 is required to support per device configurations for different revisions of device firmware, for example rev 1 of device A has configure parameters x, y and z, but revision 2 of the hand-held medical-data capture-device 104 has configuration parameters has x, y, z and k and the valid allowed range for the y parameter has been reduced.

Device Configuration Grouping—Hand-held medical-data capture-device 104 model group: The bridge 102 provides a mechanism to configure all devices within a model range to known configuration parameters. The facility to reconfigure a selected sub-group of devices that are model x and at revision level all with the same configuration information.

Device Configuration Grouping—selected group within model range: The bridge 102 provides a mechanism to configure a selected number of devices within the same model range to known configuration parameters. The facility to reconfigure a selected sub-group of devices that are model x and at revision level y Device Configuration Grouping—defined sub group: The bridge 102 provides a mechanism to configure a selected number of devices with the same model based on device characteristics e.g. revision level, operational location etc. The facility to reconfigure all devices that are model x and at revision level y, OR all model x devices that are in operation in Ward 6 is a feature.

Device Configuration files: The bridge 102 provides a method to save, load, update and edit a configuration file for a hand-held medical-data capture-device 104 model number and/or group settings. The ability to save and load configuration files and change the configuration content in the file is a required feature for EMR capture system 100. A file management mechanism in some implementations is also provided for the saved configuration files.

Dynamic configuration content: The bridge 102 in some implementations dynamically per hand-held medical-data capture-device 104 connection determine upon request by the hand-held medical-data capture-device 104 the new configuration settings for that device. Given that the medial devices will connect in a random manner to the bridge 102, the bridge 102 is required for the connected device, model, revision, unique ID etc. to maintain the configuration settings for that device.

Association of hand-held medical-data capture-device 104 to target EMR capture system(s) 100: The bridge 102 provides a mechanism to control the patient record received from a hand-held medical-data capture-device 104 to transfer the record to one of more of the supported EMR capture system(s) 100. Where more than one EMR capture system 100 is maintained by a single organization, e.g. one for ER, cardiology use and possibility one for outpatients etc. EMR capture system 100 in some implementations manage either by specific device configuration or bridge 102 configuration which EMR the patient record is to be transmitted to by the bridge 102.

Device Configuration and Status Display: In some implementations, when a hand-held medical-data capture-device 104 connects to the bridge 102 that the hand-held medical-data capture-device 104 will query its current configuration settings against the bridge 102 settings for that specific device type and device as outlined below: 1. A given device based on a unique id for that device. Note each device is required to be uniquely identified in EMR capture system 100. 2. A group of devices allocated to a physical location in the hospital, ie. Based on a ward number of other unique location reference. Accordingly, in some implementations a group of devices in a given location in some implementations is updated separately from other devices of the same type located in a different location in the same hospital environment, i.e. recovery ward 1 as opposed to ER 1. 3. A group of devices based on product type, i.e. all MD3 hand-held medical-data capture-device(s) 104, updated with the same settings. Bridge 102 device configuration options adjusted based on hand-held medical-data capture-device 104. The bridge 102 in some implementations adjusts the configuration options presented to the operator based on the capabilities of the hand-held medical-data capture-device 104 being configured. Where multiple different hand-held medical-data capture-devices 104 are supported by the EMR capture system 100 it cannot be assumed that each device from a different manufacture or from the same manufacture but a different model will have the same device level configuration parameters. Therefore the bridge 102 in some implementations determine the configuration capabilities for the hand-held medical-data capture-device 104 to be configured and present only valid configuration options for that device with valid para ranges for these options.

Device parameter Validation: The bridge 102 provides a mechanism for a given model of hand-held medical-data capture-device 104 to validate that a given configuration parameter is set within valid parameter ranges for that device model and revision. The bridge 102 is required based on the hand-held medical-data capture-device 104 model and revision level to present valid parameter ranges for the operator to configure a hand-held medical-data capture-device 104 level parameter. Device patient record acceptance check response source. The bridge 102 provides a mechanism to configure the hand-held medical-data capture-device 104 to require either: 1. A confirmation from the bridge 102 device only that a patient record has been received for processing 2. A confirmation from the bridge 102 device that the EMR capture system 100 has received and saved the patient information. In some implementations, of the configuration of the hand-held medical-data capture-device 104 the hand-held medical-data capture-device 104 reports to the operator a status indicator.

Device Hospital/Clinic Reference: A device setting to allow an organization identifier to be configured on the hand-held medical-data capture-device 104. The hand-held medical-data capture-device 104 can be configured with an alphanumeric identification string, max 30 characters that allows the organization to indicate to the Hospital/clinic that the hand-held medical-data capture-device 104 is in use with, e.g. "Boston General".

Device Ward Location reference: A device setting to allow an operational location identifier to be configured on the hand-held medical-data capture-device 104. The hand-held medical-data capture-device 104 is to be configured with an alphanumeric identification string, max 30 characters that allows the organization to indicate an operational area within the organization, e.g. "General Ward #5".

Device Asset Number: A device setting to allow an organization asset number to be configured on the hand-held medical-data capture-device 104 The hand-held medical-data capture-device 104 is to be configured with an alphanumeric identification string, max 30 characters to allow the organization to provide an asset tag for the hand-held medical-data capture-device 104.

Display device Manufacture Name, Device Model and Serial Number: A method to display the manufacture name, device model number and device serial number for the unit is provided. EMR capture system 100 can provide a method to determine the manufacture name, model number and device level serial number for the hand-held medical-data capture-device 104 for display purposes only, alphanumeric identification string, max 60 characters in length for each of the three parameters.

Display hand-held medical-data capture-device 104 unique ID reference tag: A method to display the device level unique identifier for the unit. For regulatory traceability reasons, each device is to support a unique identification number this number in some implementations be displayed by the EMR capture system 100. In some implementations, an alphanumeric identification string is a maximum of 120 characters. This parameter is not to be updateable by the EMR capture system 100.

Device last Check/Calibration Date: A method to display and set the date of the last check or re-calibration action for the hand-held medical-data capture-device 104. This will allow the bridge 102 to determine which devices are required to be re-checked and present that information to the operator of EMR capture system 100. All hand-held medical-data capture-devices 104 with a measurement function are required to be checked for accuracy on a regular basis. EMR capture system 100 provides a mechanism to update the hand-held medical-data capture-device 104 date of last check/calibration when a device level check has been carried out.

Device Temperature Display units: Configuration option for the displayed temperature units for the hand-held medical-data capture-device 104, Centigrade or Fahrenheit. For patient temperature result the unit in some implementations be configured for reporting temperatures in degrees centigrade or Fahrenheit. Default is: Fahrenheit. Note this is for device level reporting to the operator for the hand-held medical-data capture-device 104, the hand-held medical-data capture-device 104 will report all temperatures in Kelvin. The bridge 102 will also require a configuration parameter for the display of any temperature results.

Operator scan enable/disable: The bridge 102 can provide a mechanism to enable or disable the hand-held medical-data capture-device 104 level operator ID scan action. The operator ID scan capability is to be configurable on a per device basis so that it can be enabled or disabled. Allow Operator Scan Repeat for more than one patient scan: The bridge 102 can provide a mechanism to enable/disable the hand-held medical-data capture-device 104 to take a single operator ID scan and associate that id with multiple patient measurements. Where the clinical work flow allows for a known number of patient scans, or predetermined time frame, to be taken by a single operator an enable/disable feature for the hand-held medical-data capture-device 104 is to be provided. Default is: disabled Max number of patient scans per operator scan: The bridge 102 can provide a configuration parameter for controlling the number of patient ID scans after an operator ID scan before the operator ID scan has to be taken again by the hand-held medical-data capture-device 104. A number 1 to 12 The number of patient scans that are allowed to be taken by the hand-held medical-data capture-device 104 and assigned the same operator ID Default: 1 Max time for multiple patient scans to one operator scan: The bridge 102 can provide a configuration parameter for controlling the time frame in seconds that a single operator ID scan can be used for multiple patient ID scans. A time limit in seconds 0 to (30*60) seconds, to allow a hand-held medical-data capture-device 104 to associate a single operator ID with multiple patient records in this time. In some implementations, a parameter of 0 disables the time limit range checking. The default is 0.

Figure 3:
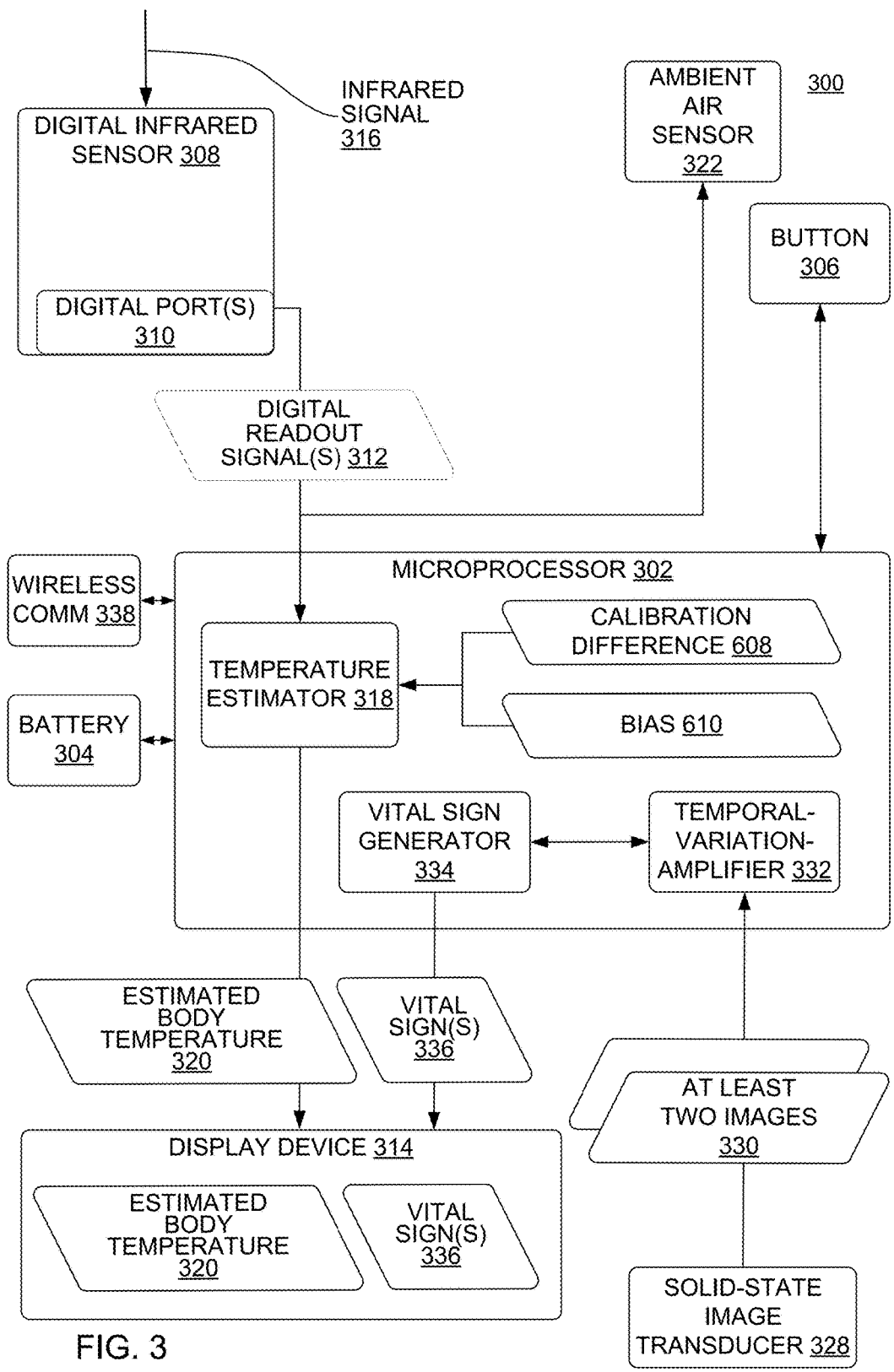
FIG. 3 is a block diagram of a non-touch biologic detector that includes a digital infrared sensor, according to an implementation.

Digital Non-Touch Thermometers and Vital Sign Motion Amplification Detectors Apparatus Implementations FIG. 3 is a block diagram of a non-touch biologic detector 300 that includes a digital infrared sensor, according to an implementation. Non-touch biologic detector 300 is an apparatus to measure temperature and other vital signs.

The non-touch biologic detector 300 includes a microprocessor 302. The non-touch biologic detector 300 includes a battery 304, a single button 306 and a digital infrared sensor 308 that is operably coupled to the microprocessor 302. The digital infrared sensor 308 includes digital ports 310 that provide only digital readout signal 312. The non-touch biologic detector 300 includes a display device 314 that is operably coupled to the microprocessor 302. The microprocessor 302 is operable to receive from the digital ports 310 that provide only digital readout signal 312. The digital readout signal 312 is representative of an infrared signal 316 detected by the digital infrared sensor 308. A temperature estimator 318 in the microprocessor 302 is operable to estimate the temperature 320 from the digital readout signal 312 that is representative of the infrared signal 316, a representation of an ambient air temperature reading from an ambient air sensor 322, a representation of a calibration difference from a memory location that stores a calibration difference 324 and a memory location that stores a representation of a bias 326 in consideration of a temperature sensing mode.

Some implementations of the non-touch biologic detector 300 include a solid-state image transducer 328 that is operably coupled to the microprocessor 302 and is operable to provide two or more images 330 to a temporal-variation-amplifier 332 and a vital sign generator 334 in the microprocessor 302 to estimate one or more vital signs 336 that are displayed on the display device 314.

The non-touch biologic detector 300 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

In some implementations, the digital IR sensor 308 is a low noise amplifier, 17-bit ADC and powerful DSP unit through which high accuracy and resolution of the estimated body temperature 320 by the apparatus in FIGS. 3-5, 8, 11-12 and 35-39 is achieved.

In some implementations, the digital IR sensor 308, 10-bit pulse width modulation (PWM) is configured to continuously transmit the measured temperature in range of −20 . . . 120° C., with an output resolution of 0.14° C. The factory default power on reset (POR) setting is SMBus.

In some implementations, the digital IR sensor 308 is packaged in an industry standard TO-39 package.

In some implementations, the generated object and ambient temperatures are available in RAM of the digital IR sensor 308 with resolution of 0.01° C. The temperatures are accessible by 2 wire serial SMBus compatible protocol (0.02° C. resolution) or via 10-bit PWM (Pulse Width Modulated) output of the digital IR sensor 308.

In some implementations, the digital IR sensor 308 is factory calibrated in wide temperature ranges: −40 . . . 85° C. for the ambient temperature and −70 . . . 380° C. for the object temperature.

In some implementations, of the digital IR sensor 308, the measured value is the average temperature of all objects in the Field Of View (FOV) of the sensor. In some implementations, the digital IR sensor 308 has a standard accuracy of ±0.5° C. around room temperatures, and in some implementations, the digital IR sensor 308 has an accuracy of ±0.2° C. in a limited temperature range around the human body temperature.

These accuracies are only guaranteed and achievable when the sensor is in thermal equilibrium and under isothermal conditions (there are no temperature differences across the sensor package). The accuracy of the detector can be influenced by temperature differences in the package induced by causes like (among others): Hot electronics behind the sensor, heaters/coolers behind or beside the sensor or by a hot/cold object very close to the sensor that not only heats the sensing element in the detector but also the detector package. In some implementations, of the digital IR sensor 308, the thermal gradients are measured internally and the measured temperature is compensated in consideration of the thermal gradients, but the effect is not totally eliminated. It is therefore important to avoid the causes of thermal gradients as much as possible or to shield the sensor from the thermal gradients.

In some implementations, the digital IR sensor 308 is calibrated for an object emissivity of 1, but in some implementations, the digital IR sensor 308 is calibrated for any emissivity in the range 0.1 . . . 1.0 without the need of recalibration with a black body.

In some implementations, of the digital IR sensor 308, the PWM can be easily customized for virtually any range desired by the customer by changing the content of 2 EEPROM cells. Changing the content of 2 EEPROM cells has no effect on the factory calibration of the device. The PWM pin can also be configured to act as a thermal relay (input is To), thus allowing for an easy and cost effective implementation in thermostats or temperature (freezing/boiling) alert applications. The temperature threshold is programmable by the microprocessor 302 of the non-touch biologic detector. In a non-touch biologic detector having a SMBus system the programming can act as a processor interrupt that can trigger reading all slaves on the bus and to determine the precise condition.

In some implementations, the digital IR sensor 308 has an optical filter (long-wave pass) that cuts off the visible and near infra-red radiant flux is integrated in the package to provide ambient and sunlight immunity. The wavelength pass band of the optical filter is from 5.5 till 14 μm.

In some implementations, the digital IR sensor 308 is controlled by an internal state machine, which controls the measurements and generations of the object and ambient temperatures and does the post-processing of the temperatures to output the temperatures through the PWM output or the SMBus compatible interface.

Some implementations of the non-touch biologic detector includes 2 IR sensors, the output of the IR sensors being amplified by a low noise low offset chopper amplifier with programmable gain, converted by a Sigma Delta modulator to a single bit stream and fed to a DSP for further processing. The signal is treated by programmable (by means of EEPROM contend) FIR and IIR low pass filters for further reduction of the bandwidth of the input signal to achieve the desired noise performance and refresh rate. The output of the IIR filter is the measurement result and is available in the internal RAM. 3 different cells are available: One for the on-board temperature sensor and 2 for the IR sensors. Based on results of the above measurements, the corresponding ambient temperature Ta and object temperatures To are generated. Both generated temperatures have a resolution of 0.01° C. The data for Ta and To is read in two ways: Reading RAM cells dedicated for this purpose via the 2-wire interface (0.02° C. resolution, fixed ranges), or through the PWM digital output (10 bit resolution, configurable range). In the last step of the measurement cycle, the measured Ta and To are rescaled to the desired output resolution of the PWM) and the regenerated data is loaded in the registers of the PWM state machine, which creates a constant frequency with a duty cycle representing the measured data.

In some implementations, the digital IR sensor 308 includes a SCL pin for Serial clock input for 2 wire communications protocol, which supports digital input only, used as the clock for SMBus compatible communication. The SCL pin has the auxiliary function for building an external voltage regulator. When the external voltage regulator is used, the 2-wire protocol for a power supply regulator is overdriven.

In some implementations, the digital IR sensor 308 includes a slave deviceA/PWM pin for Digital input/output. In normal mode the measured object temperature is accessed at this pin Pulse Width Modulated. In SMBus compatible mode the pin is automatically configured as open drain NMOS. Digital input/output, used for both the PWM output of the measured object temperature(s) or the digital input/output for the SMBus. In PWM mode the pin can be programmed in EEPROM to operate as Push/Pull or open drain NMOS (open drain NMOS is factory default). In SMBus mode slave deviceA is forced to open drain NMOS I/O, push-pull selection bit defines PWM/Thermal relay operation. The PWM/slave deviceA pin the digital IR sensor 308 operates as PWM output, depending on the EEPROM settings. When WPWM is enabled, after POR the PWM/slave deviceA pin is directly configured as PWM output. When the digital IR sensor 308 is in PWM mode, SMBus communication is restored by a special command. In some implementations, the digital IR sensor 308 is read via PWM or SMBus compatible interface. Selection of PWM output is done in EEPROM configuration (factory default is SMBus). PWM output has two programmable formats, single and dual data transmission, providing single wire reading of two temperatures (dual zone object or object and ambient). The PWM period is derived from the on-chip oscillator and is programmable.

In some implementations, the digital IR sensor 308 includes a VDD pin for External supply voltage and a VSS pin for ground.

The microprocessor 302 has read access to the RAM and EEPROM and write access to 9 EEPROM cells (at addresses 0x00, 0x01, 0x02, 0x03, 0x04, 0x05*, 0x0E, 0x0F, 0x09). When the access to the digital IR sensor 308 is a read operation, the digital IR sensor 308 responds with 16 data bits and 8 bit PEC only if its own slave address, programmed in internal EEPROM, is equal to the SA, sent by the master. A slave feature allows connecting up to 127 devices (SA=0x00 . . . 0x07F) with only 2 wires. In order to provide access to any device or to assign an address to a slave device before slave device is connected to the bus system, the communication starts with zero slave address followed by low R/W bit. When the zero slave address followed by low R/W bit sent from the microprocessor 302, the digital IR sensor 308 responds and ignores the internal chip code information.

In some implementations, two digital IR sensors 308 are not configured with the same slave address on the same bus.

In regards to bus protocol, after every received 8 bits the slave device should issue ACK or NACK. When a microprocessor 302 initiates communication, the microprocessor 302 first sends the address of the slave and only the slave device which recognizes the address will ACK, the rest will remain silent. In case the slave device NACKs one of the bytes, the microprocessor 302 stops the communication and repeat the message. A NACK could be received after the packet error code (PEC). A NACK after the PEC means that there is an error in the received message and the microprocessor 302 will try resending the message. PEC generation includes all bits except the START, REPEATED START, STOP, ACK, and NACK bits. The PEC is a CRC-8 with polynomial X8+X2+X1+1. The Most Significant Bit of every byte is transferred first.

In single PWM output mode the settings for PWM1 data only are used. The temperature reading can be generated from the signal timing as:

$$T_{OUT} = \left(\frac{2t_2}{T} \times (T_{O\_MAX} - T_{O\_MIN})\right) + T_{O\_MIN}$$

where Tmin and Tmax are the corresponding rescale coefficients in EEPROM for the selected temperature output (Ta, object temperature range is valid for both Tobj1 and Tobj2 as specified in the previous table) and T is the PWM period. Tout is TO1, TO2 or Ta according to Config Register [5:4] settings.

The different time intervals t1 . . . t4 have following meaning:

t1: Start buffer. During t1 the signal is always high. t1=0.125 s×T (where T is the PWM period)

t2: Valid Data Output Band, 0 . . . ½T. PWM output data resolution is 10 bit.

t3: Error band—information for fatal error in EEPROM (double error detected, not correctable).

t3=0.25 s× T. Therefore a PWM pulse train with a duty cycle of 0.875 will indicate a fatal error in EEPROM (for single PWM format). FE means Fatal Error.

In regards to a format for extended PWM, the temperature transmitted in Data 1 field can be generated using the following equation:

$$T_{OUT1} = \left(\frac{4t_2}{T} \times (T_{MAX1} - T_{MIN1})\right) + T_{MIN1}$$

For Data 2 field the equation is:

$$T_{OUT2} = \left(\frac{4t_5}{T} \times (T_{MAX2} - T_{MIN2})\right) + T_{MIN2}$$

Figure 4:
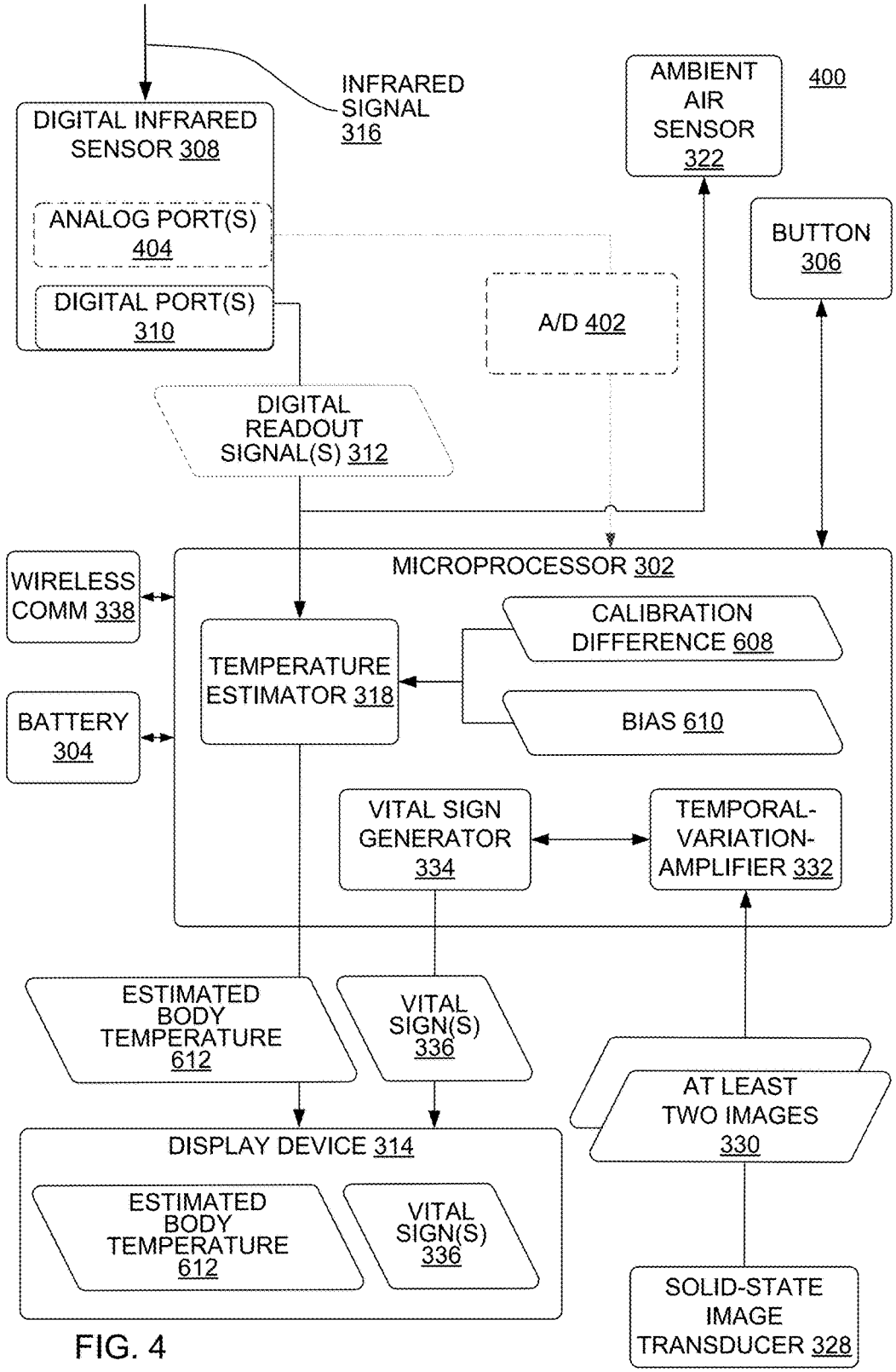
FIG. 4 is a block diagram of a non-touch biologic detector that includes a digital infrared sensor and that does not include an analog-to-digital converter, according to an implementation.

FIG. 4 is a block diagram of a non-touch biologic detector that includes a digital infrared sensor and that does not include an analog-to-digital converter, according to an implementation. The non-touch biologic detector 400 does not include an analog-to-digital (A/D) converter 402 operably coupled between the digital infrared sensor 308 and the microprocessor 302. The digital infrared sensor 308 also does not include analog readout ports 404. The dashed lines of the A/D converter 402 and the analog readout ports 404 indicates absence of the A/D converter 402 and the analog readout ports 404 in the non-touch biologic detector 400.

The non-touch biologic detector 400 includes a microprocessor 302. The non-touch biologic detector 400 includes a battery 304, a single button 306, a display device 314 and a digital infrared sensor 308 that is operably coupled to the microprocessor 302. No analog-to-digital converter is operably coupled between the digital infrared sensor 308 and the microprocessor 302. The digital infrared sensor 308 has only digital ports 310 and the digital infrared sensor 308 has no analog sensor readout ports. The microprocessor 302 is operable to receive from the digital ports 310 a digital readout signal 312 that is representative of an infrared signal 316 detected by the digital infrared sensor 308 and to determine the temperature 320 from the digital readout signal 312 that is representative of the infrared signal 316.

Some implementations of the non-touch biologic detector 400 include a solid-state image transducer 328 that is operably coupled to the microprocessor 302 and is operable to provide two or more images 330 to a temporal-variation-amplifier 332 and a vital sign generator 334 in the microprocessor 302 to estimate one or more vital signs 336 that are displayed on the display device 314.

The non-touch biologic detector 400 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

Figure 5:
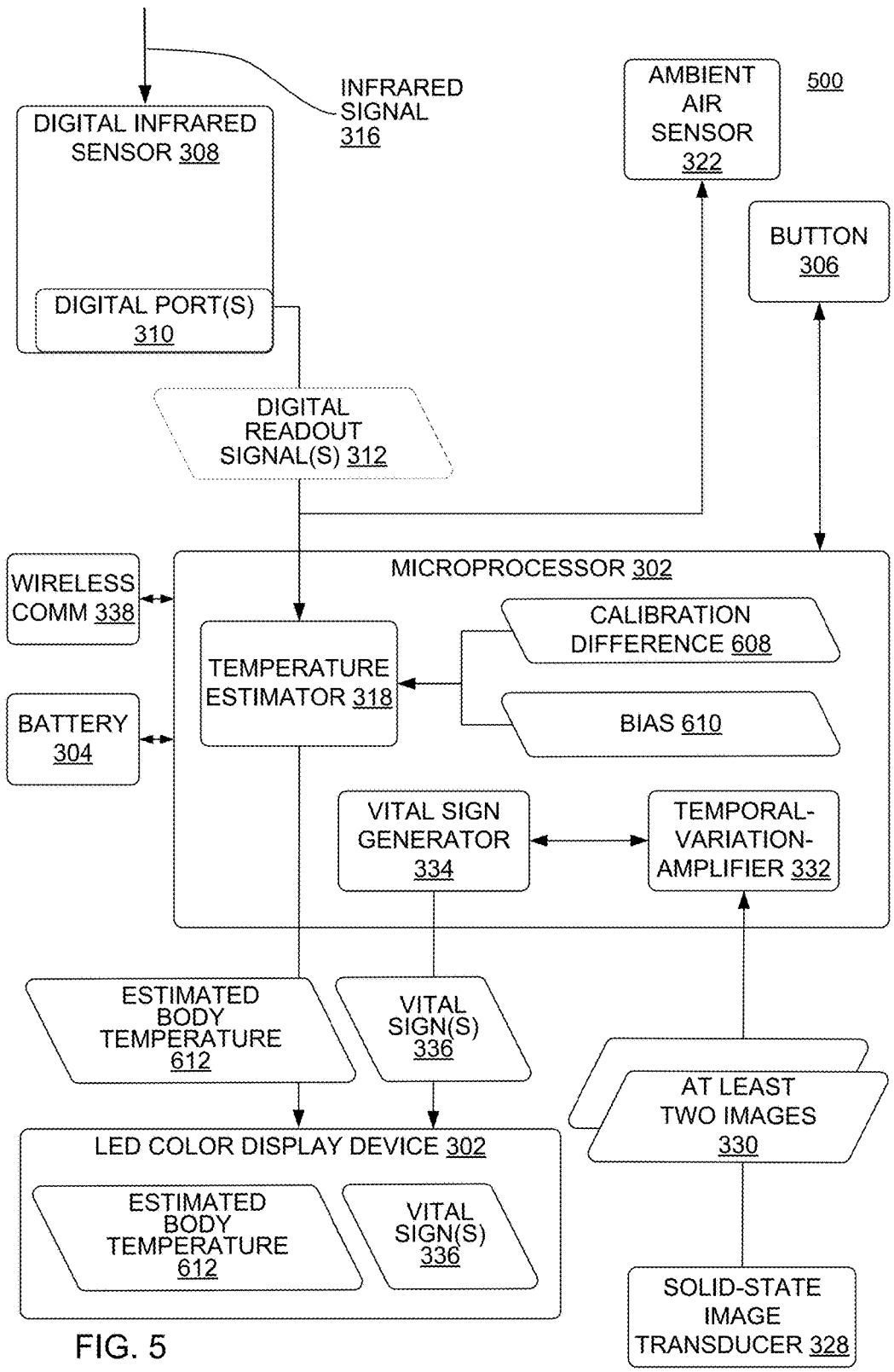
FIG. 5 is a block diagram of a non-touch biologic detector that includes a digital infrared sensor and a color display device, according to an implementation.

FIG. 5 is a block diagram of a non-touch biologic detector 500 that includes a digital infrared sensor and a color display device, according to an implementation. In FIG. 5, the display device 314 of FIG. 3 is a LED color display device 502.

The non-touch biologic detector 500 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

Non-Touch Cubic-Estimation Thermometers Apparatus Implementations

Figure 6:
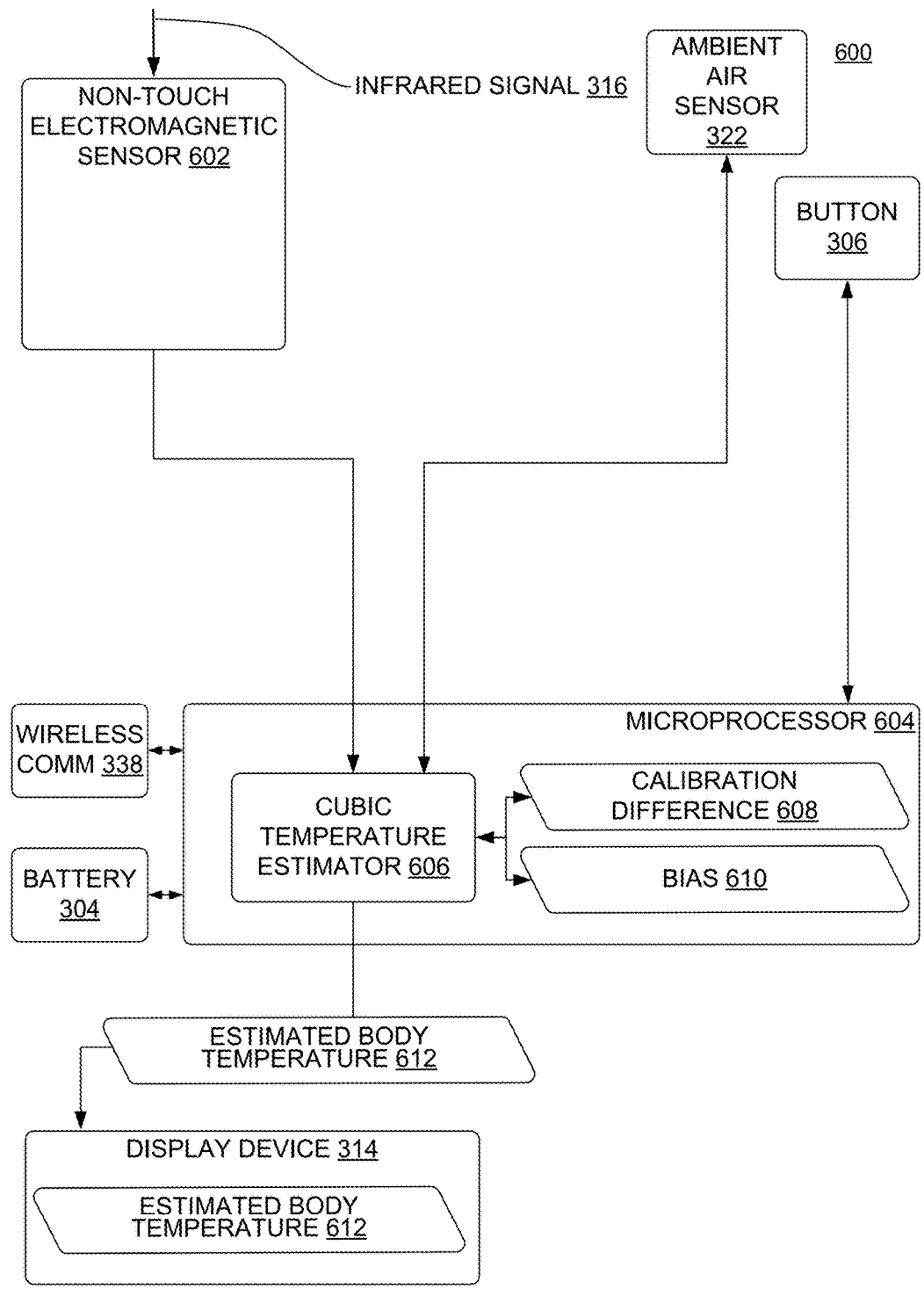
FIG. 6 is a block diagram of apparatus that estimates a body core temperature of an external source point from a no-touch electromagnetic sensor, according to an implementation.

FIG. 6 is a block diagram of apparatus 600 that estimates a body core temperature of an external source point from a non-touch electromagnetic sensor, according to an implementation. The apparatus 600 includes a battery 304, a single button 306, a display device 314, a non-touch electromagnetic sensor 602 and an ambient air sensor 322 that are operably coupled to the microprocessor 604. The microprocessor 604 is operable to receive a representation of an infrared signal 316 of the external source point from the non-touch electromagnetic sensor 602. The microprocessor 604 includes a cubic temperature estimator 606 that is operable to estimate the body core temperature 612 of the subject from the representation of the electromagnetic energy of the external source point.

The cubic temperature estimator 606 that estimates body temperature in reference to a cubic relationship that represents three thermal ranges between the body core temperature and the numerical representation of the electromagnetic energy of the external source point. The cubic relationship includes a coefficient representative of different relationships between the external source point and the body core temperature in the three thermal ranges in reference to the numerical representation of the electromagnetic energy of the external source point, numerical constants for each cubic factor, ambient air temperature and the three thermal ranges.

The cubic relationship for all ranges of ambient temperatures provides best results because a linear or a quadratic relationship provide inaccurate estimates of body temperature, yet a quartic relationship, a quintic relationship, sextic relationship, a septic relationship or an octic relationship provide estimates along a highly irregular curve that is far too wavy or twisting with relatively sharp deviations from one ambient temperature to another ambient temperature.

The non-touch electromagnetic sensor 602 detects temperature in response to remote sensing of a surface a human or animal. In some implementations, the non-touch thermometer is an infrared temperature sensor. All humans or animals radiate infrared energy. The intensity of this infrared energy depends on the temperature of the human or animal, thus the amount of infrared energy emitted by a human or animal can be interpreted as a proxy or indication of the temperature of the human or animal. The non-touch electromagnetic sensor 602 measures the temperature of a human or animal based on the electromagnetic energy radiated by the human or animal. The measurement of electromagnetic energy is taken by the non-touch electromagnetic sensor 602 which constantly analyzes and registers the ambient temperature. When the operator of apparatus in FIG. 3 holds the non-touch electromagnetic sensor 602 about 5-8 cm (2-3 inches) from the forehead and activates the radiation sensor, the measurement is instantaneously measured. To measure a temperature using the non-touch electromagnetic sensor 602, pushing the button 306 causes a reading of temperature measurement from the non-touch electromagnetic sensor 602 and the measured temperature is thereafter displayed on the display device 314.

Body temperature of a human or animal can be measured in many surface locations of the body. Most commonly, temperature measurements are taken of the forehead, mouth (oral), inner ear (tympanic), armpit (axillary) or rectum. In addition, temperature measurements are taken of a carotid artery (the external carotid artery on the right side of a human neck). An ideal place to measure temperature is the forehead in addition to the carotid artery. When electromagnetic energy is sensed from two or more source points, for example, the forehead and the external carotid artery on the right side of a human neck, a cubic temperature estimator 606 performs one or more of the actions in the methods that are described in FIG. 27-31. The cubic temperature estimator 606 correlates the temperatures sensed by the non-touch electromagnetic sensor 602 from the multiple source points (e.g. the forehead and the carotid artery) to another temperature, such as a core temperature of the subject, an axillary temperature of the subject, a rectal temperature of the subject and/or an oral temperature of the subject. The cubic temperature estimator 606 can be implemented as a component on a microprocessor, such as main processor 3202 in FIG. 32, processing unit 3304 in FIG. 33 or microprocessor 3504 in FIG. 35 or on a memory such as flash memory 3208 in FIG. 32 or system memory 3306.

The apparatus 600 also detects the body temperature of a human or animal regardless of the room temperature because the measured temperature of the non-touch electromagnetic sensor 602 is adjusted in reference to the ambient temperature in the air in the vicinity of the apparatus. The human or animal must not have undertaken vigorous physical activity prior to temperature measurement in order to avoid a misleading high temperature. Also, the room temperature should be moderate, 50° F. to 120° F.

The apparatus 600 provides a non-invasive and non-irritating means of measuring human or animal temperature to help ensure good health.

When evaluating results, the potential for daily variations in temperature can be considered. In children less than 6 months of age daily variation is small. In children 6 months to 4 years old the variation is about 1 degree. By age 6 variations gradually increase to 4 degrees per day. In adults there is less body temperature variation.

The apparatus 600 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

Figure 7:
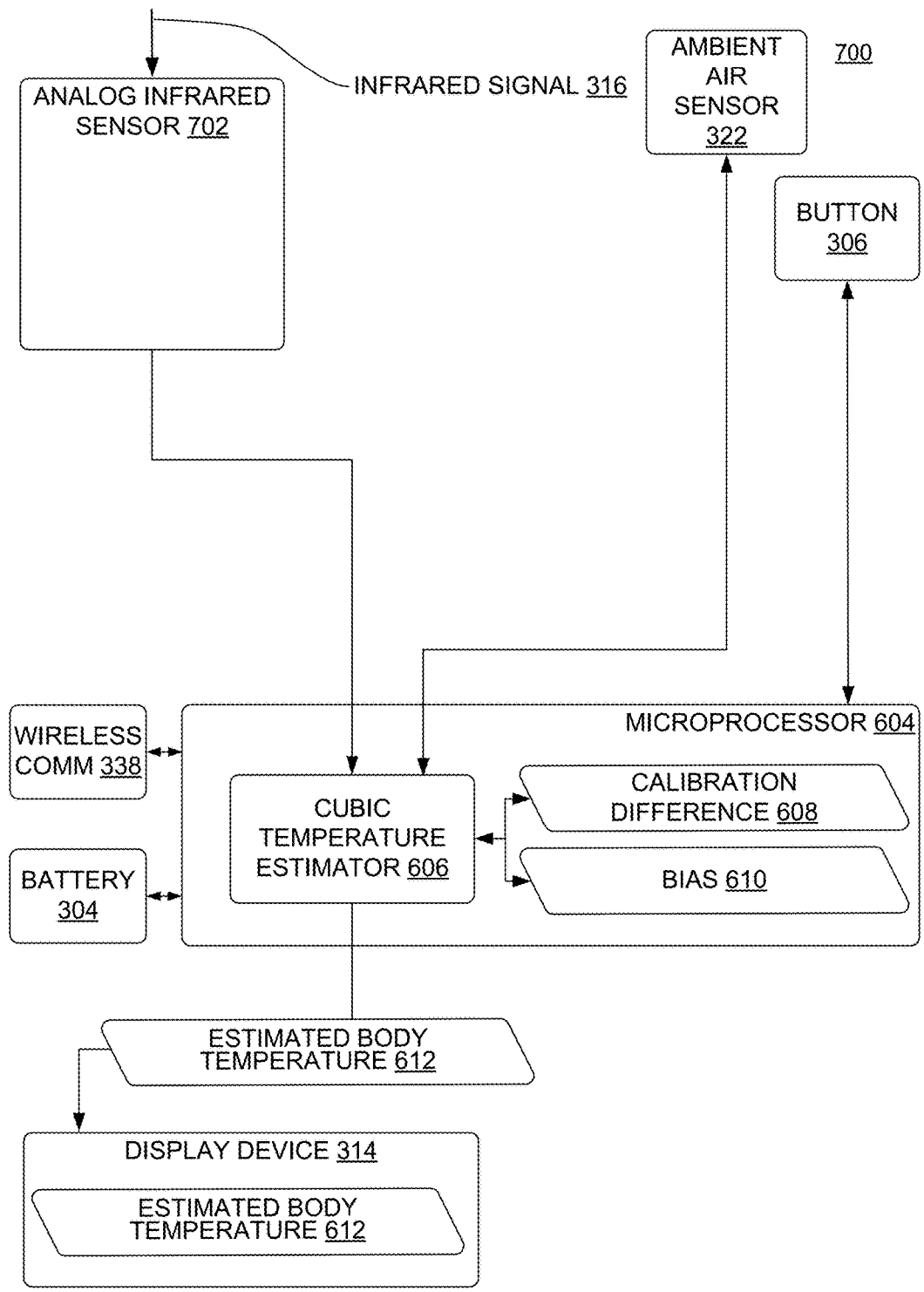
FIG. 7 is a block diagram of apparatus to estimate a body core temperature from an external source point from an analog infrared sensor, according to an implementation.

FIG. 7 is a block diagram of apparatus 700 to estimate a body core temperature from an external source point from an analog infrared sensor, according to an implementation. The apparatus 700 includes a battery 304, a single button 306, a display device 314, an analog infrared sensor 702 and an ambient air sensor 322 that are operably coupled to the microprocessor 604. The microprocessor 604 is operable to receive a representation of an infrared signal 316 of the external source point from the analog infrared sensor 702. The microprocessor 604 includes a cubic temperature estimator 606 that is operable to estimate the body core temperature 612 of the subject from the representation of the electromagnetic energy of the external source point.

The apparatus 700 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

Figure 8:
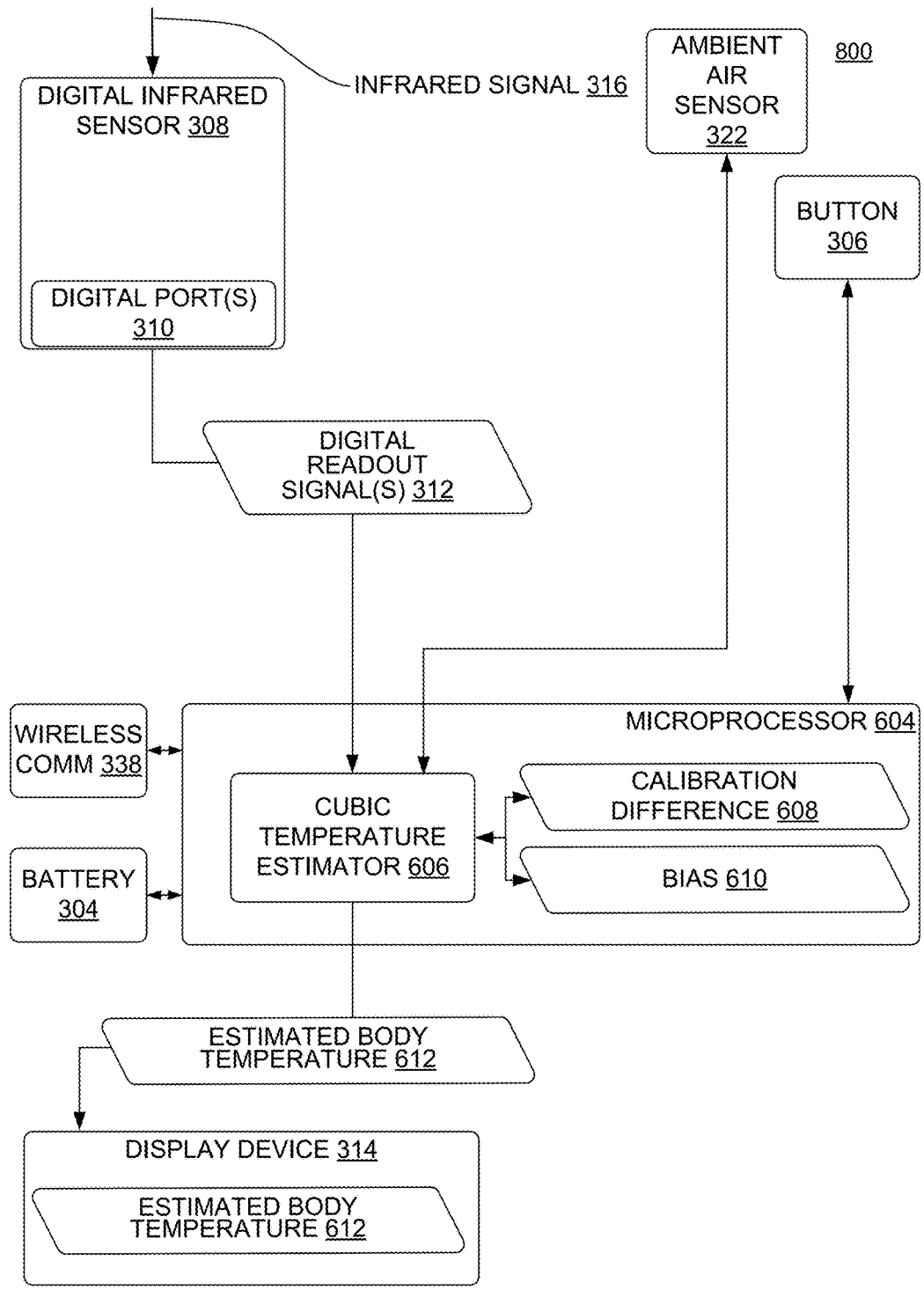
FIG. 8 is a block diagram of apparatus to estimate a body core temperature from an external source point from a digital infrared sensor, according to an implementation.

FIG. 8 is a block diagram of apparatus 800 to estimate a body core temperature from an external source point from a digital infrared sensor, according to an implementation. The apparatus 800 includes a battery 304, a single button 306, a display device 314, a digital infrared sensor 308 and an ambient air sensor 322 that are operably coupled to the microprocessor 604. The microprocessor 604 is operable to receive a representation of an infrared signal 316 of the external source point from the digital infrared sensor 308. The microprocessor 604 includes a cubic temperature estimator 606 that is operable to estimate the body core temperature 612 of the subject from the representation of the electromagnetic energy of the external source point.

The apparatus 800 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

Figure 9:
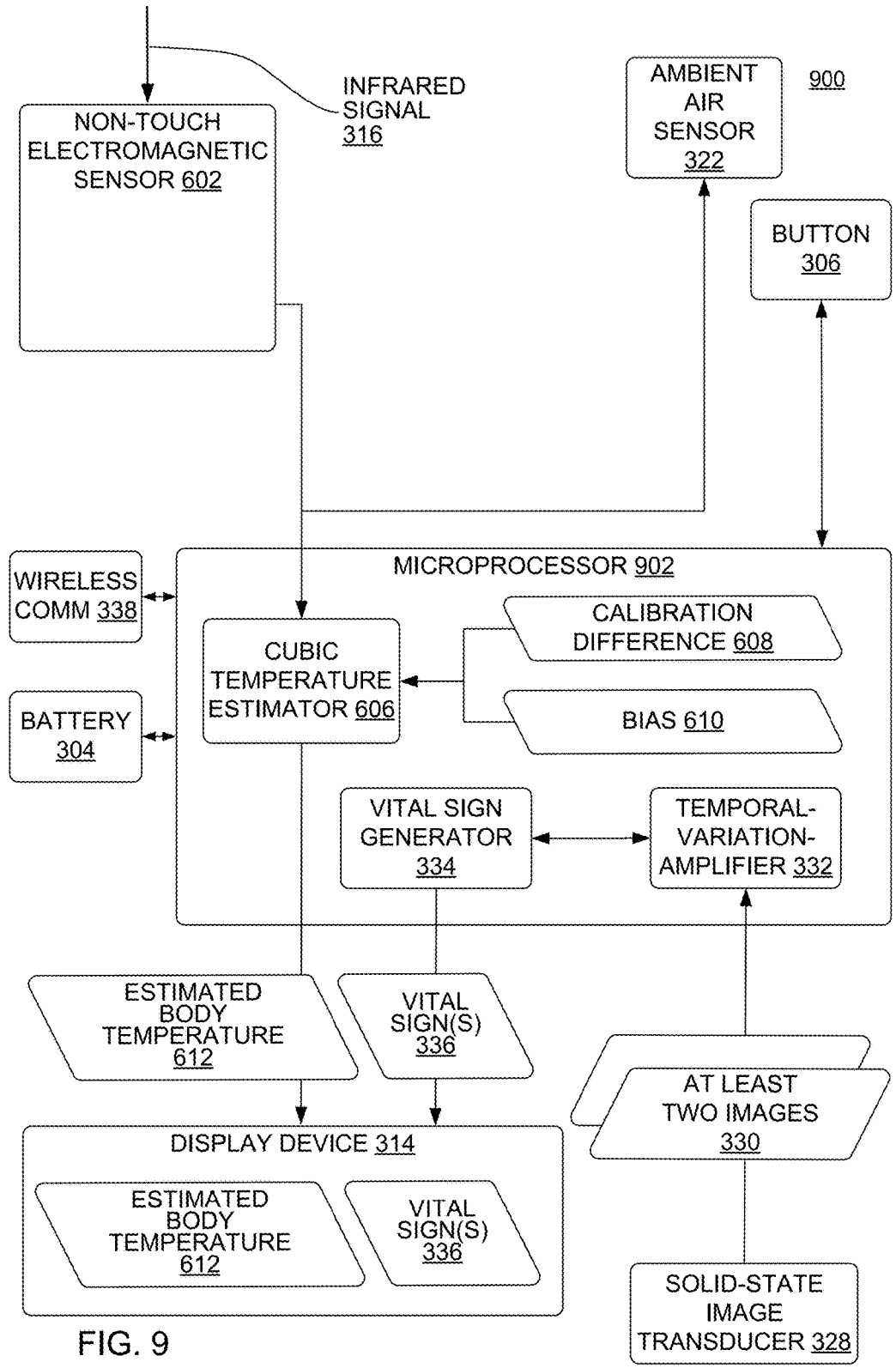
FIG. 9 is a block diagram of apparatus that estimates a body core temperature of an external source point from a non-touch electromagnetic sensor and that detects vital-signs from images captured by a solid-state image transducer, according to an implementation.

Non-Touch Cubic-Estimation Thermometer and
Vital Sign Detection Apparatus Implementations FIG. 9 is a block diagram of apparatus 900 that estimates a body core temperature of an external source point from a non-touch electromagnetic sensor and that detects vital-signs from images captured by a solid-state image transducer, according to an implementation. The apparatus 900 includes a battery 304, a single button 306, a display device 314, a non-touch electromagnetic sensor 902 and an ambient air sensor 322 that are operably coupled to the microprocessor 902. The microprocessor 902 is operable to receive a representation of an infrared signal 316 of the external source point from the non-touch electromagnetic sensor 902. The microprocessor 902 includes a cubic temperature estimator 606 that is operable to estimate the body core temperature 612 of the subject from the representation of the electromagnetic energy of the external source point. The apparatus 900 includes a solid-state image transducer 328 that is operably coupled to the microprocessor 902 and is operable to provide two or more images 330 to the microprocessor 902.

The apparatus 900 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

Figure 10:
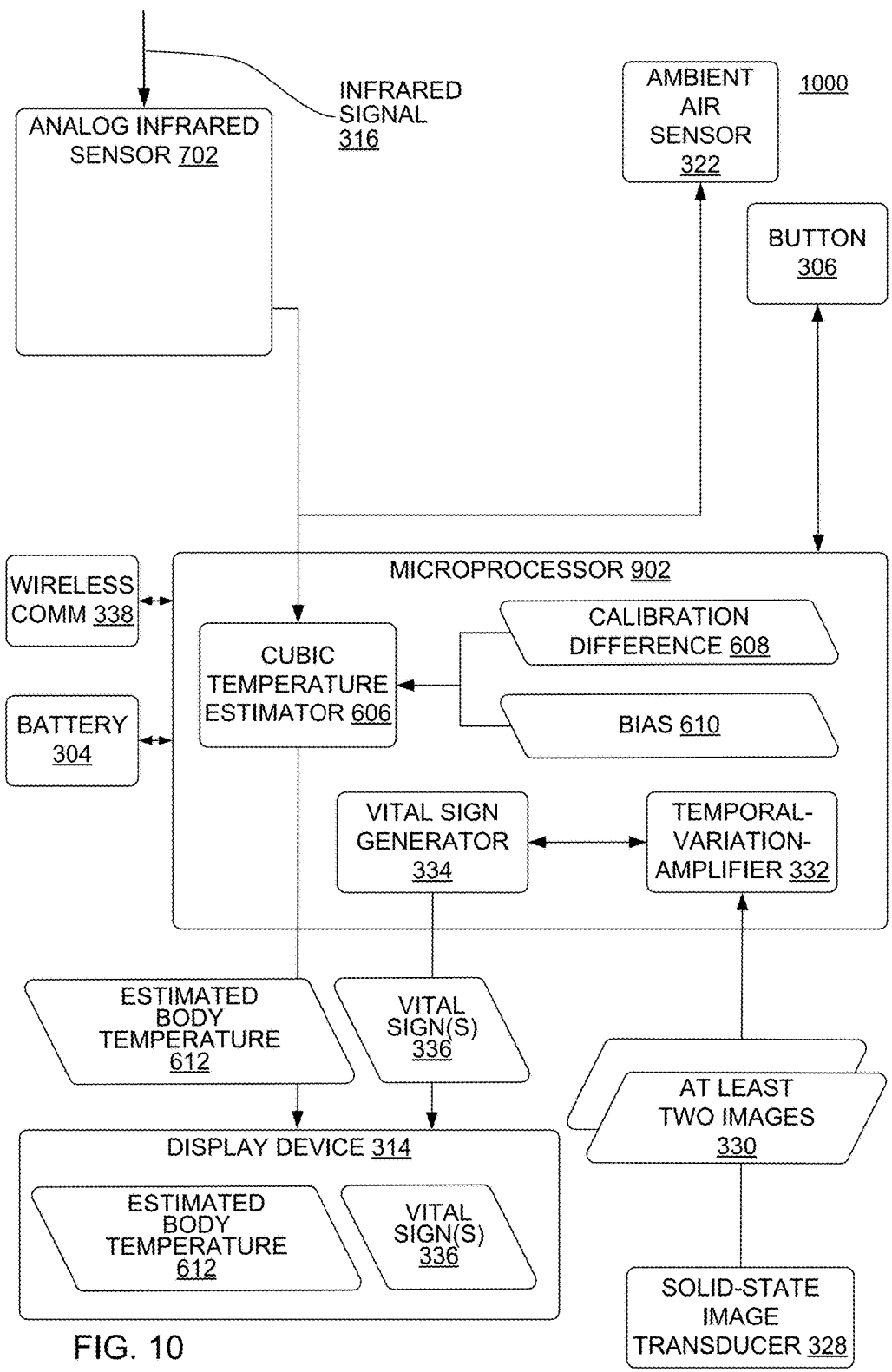
FIG. 10 is a block diagram of apparatus that estimates a body core temperature of an external source point from an analog infrared sensor and that detects vital-signs from images captured by a solid-state image transducer, according to an implementation.

FIG. 10 is a block diagram of apparatus 1000 that estimates a body core temperature of an external source point from an analog infrared sensor and that detects vital-signs from images captured by a solid-state image transducer, according to an implementation. The apparatus 1000 includes a battery 304, a single button 306, a display device 314, an analog infrared sensor 702 and an ambient air sensor 322 that are operably coupled to the microprocessor 902. The microprocessor 902 is operable to receive a representation of an infrared signal 316 of the external source point from the analog infrared sensor 702. The microprocessor 902 includes a cubic temperature estimator 606 that is operable to estimate the body core temperature 612 of the subject from the representation of the electromagnetic energy of the external source point. The apparatus 1000 includes a solid-state image transducer 328 that is operably coupled to the microprocessor 902 and is operable to provide two or more images 330 to the microprocessor 902.

The apparatus 1000 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

Figure 11:
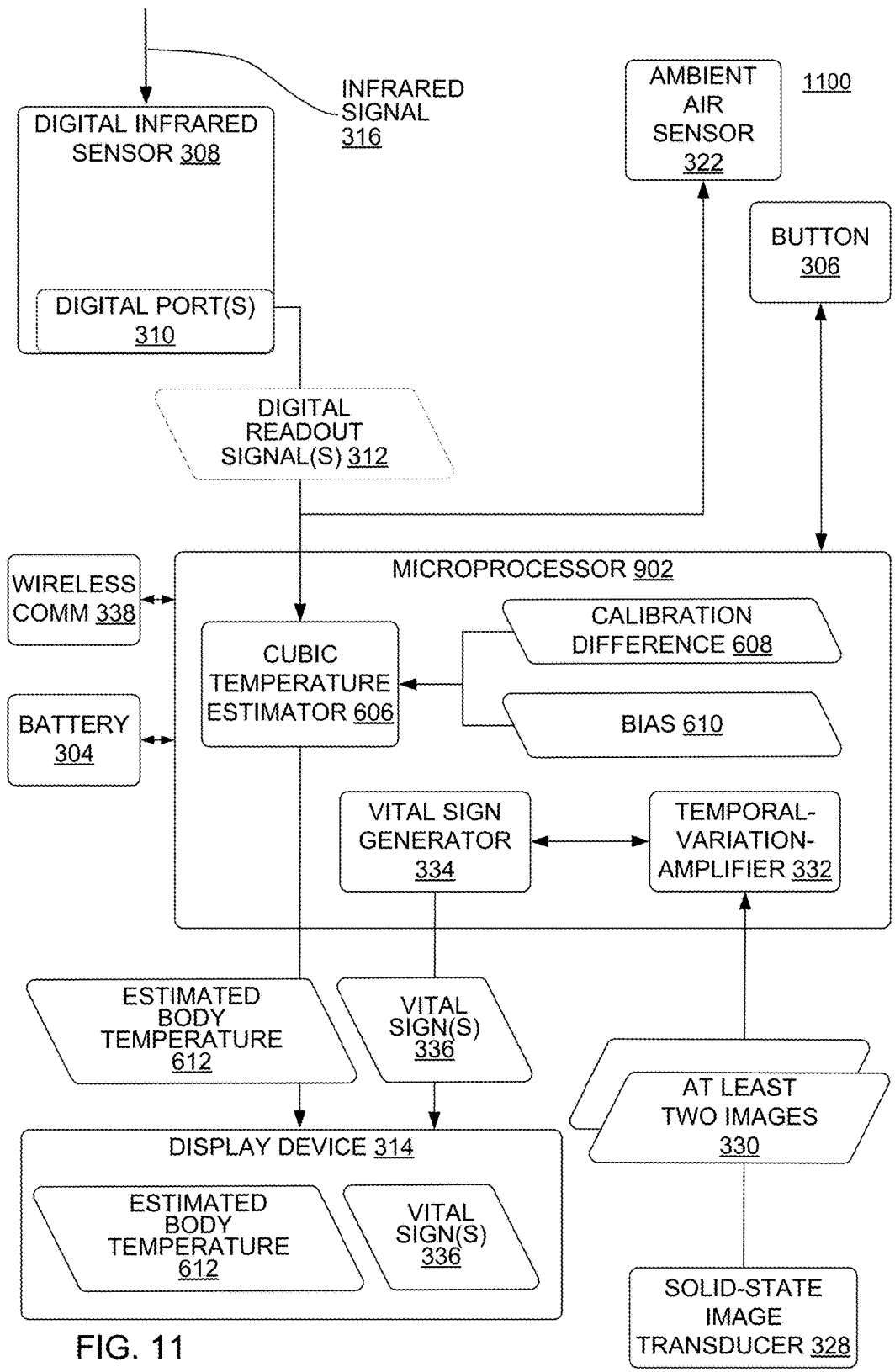
FIG. 11 is a block diagram of apparatus that estimates a body core temperature of an external source point from a digital infrared sensor and that detects vital-signs from images captured by a solid-state image transducer, according to an implementation.

FIG. 11 is a block diagram of apparatus 1100 that estimates a body core temperature of an external source point from a digital infrared sensor and that detects vital-signs from images captured by a solid-state image transducer, according to an implementation. The apparatus 1100 includes a battery 304, a single button 306, a display device 314, a digital infrared sensor 308 and an ambient air sensor 322 that are operably coupled to the microprocessor 902. The microprocessor 902 is operable to receive a representation of an infrared signal 316 of the external source point from the digital infrared sensor 308. The microprocessor 902 includes a cubic temperature estimator 606 that is operable to estimate the body core temperature 612 of the subject from the representation of the electromagnetic energy of the external source point. The apparatus 1100 includes a solid-state image transducer 328 that is operably coupled to the microprocessor 902 and is operable to provide two or more images 330 to the microprocessor 902.

The apparatus 1100 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

Figure 12:
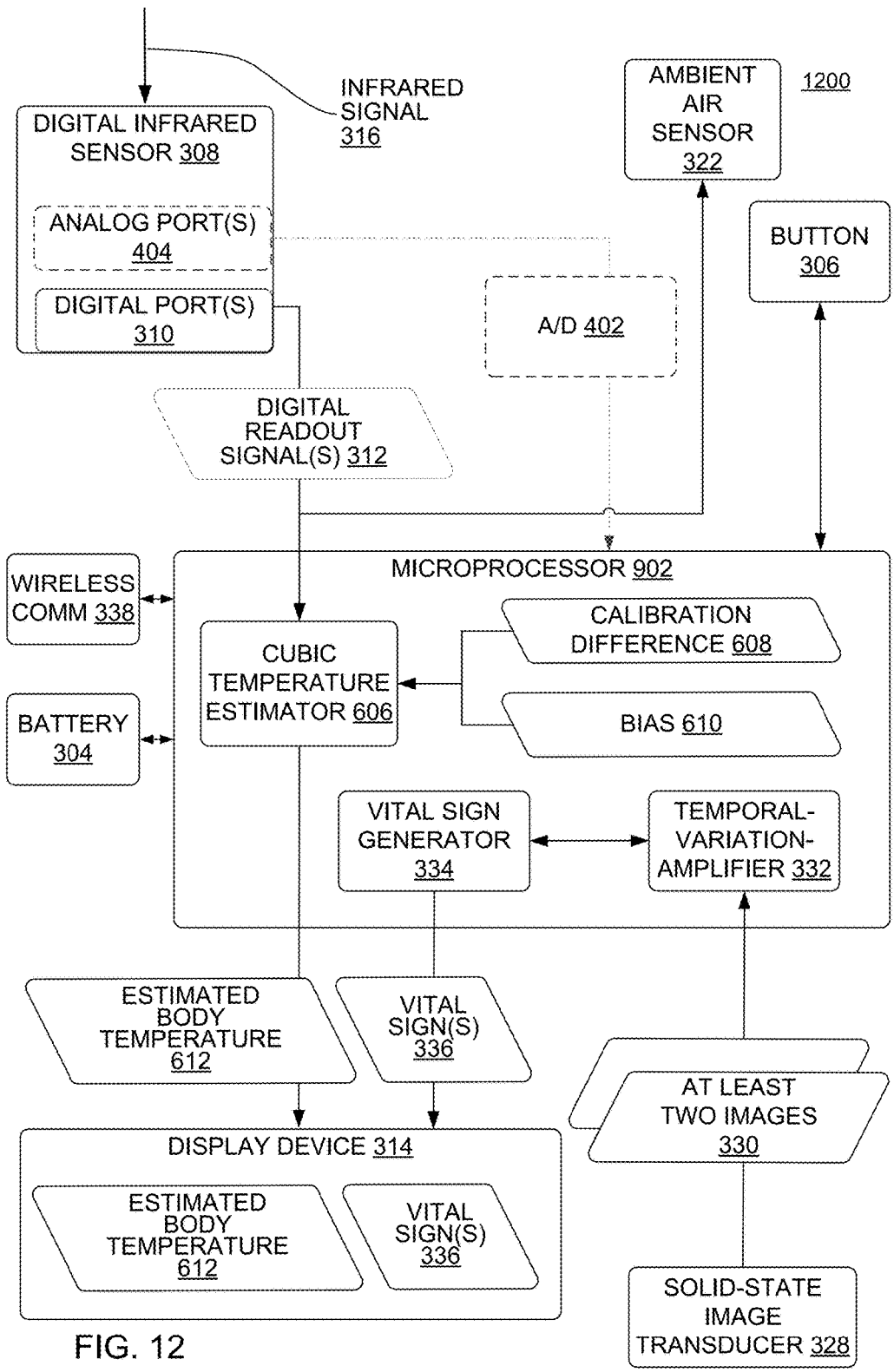
FIG. 12 is a block diagram of apparatus that estimates a body core temperature of an external source point from a digital infrared sensor, that does not include an analog-to-digital converter and that detects vital-signs from images captured by a solid-state image transducer, according to an implementation.

FIG. 12 is a block diagram of apparatus 1200 that estimates a body core temperature of an external source point from a digital infrared sensor, that does not include an analog-to-digital converter and that detects vital-signs from images captured by a solid-state image transducer, according to an implementation. The apparatus 1200 includes a battery 304, a single button 306, a display device 314, a digital infrared sensor 308 and an ambient air sensor 322 that are operably coupled to the microprocessor 902. The microprocessor 902 is operable to receive a representation of an infrared signal 316 of the external source point from the digital infrared sensor 308. The microprocessor 902 includes a cubic temperature estimator 606 that is operable to estimate the body core temperature 612 of the subject from the representation of the electromagnetic energy of the external source point. The apparatus 1200 includes a solid-state image transducer 328 that is operably coupled to the microprocessor 902 and is operable to provide two or more images 330 to the microprocessor 902. The apparatus 900 does not include an analog-to-digital (A/D) converter 402 operably coupled between the digital infrared sensor 308 and the microprocessor 902. The digital infrared sensor 308 also does not include analog readout ports 404. The dashed lines of the analog-to-digital (A/D) converter 402 and the analog readout ports 404 indicates absence of the A/D converter 402 and the analog readout ports 404 in the apparatus 900.

The apparatus 1200 also includes a wireless communication subsystem 338 or other external communication subsystem such as an Ethernet port, that provides communication to the EMR capture system 100. In some implementations, the wireless communication subsystem 338 is communication subsystem 3204 in FIG. 41.

In regards to the structural relationship of the digital infrared sensor 308 and the microprocessor 302 in FIGS. 3-5, 8 and 11-12, heat radiation on the digital infrared sensor 308 from any source such as the microprocessor 302 or heat sink, will distort detection of infrared energy by the digital infrared sensor 308. In order to prevent or at least reduce heat transfer between the digital infrared sensor 308 and the microprocessor 302, the apparatus in FIGS. 3-5, 8 and 11-12 are low-powered devices and thus low heat-generating devices that are also powered by a battery 304; and that are only used for approximately a 5 second period of time for each measurement (1 second to acquire the temperature samples and generate the body core temperature result, and 4 seconds to display that result to the operator) so there is little heat generated by the apparatus in FIGS. 3-5, 8 and 11-12 in active use.

The internal layout of the apparatus in FIGS. 3-5, 8 and 11-12 minimizes as practically as possible the digital infrared sensor as far away in distance from all other components such the microprocessor (302, 604 or 902) within the practical limitations of the industrial design of the apparatus in FIGS. 3-5, 8 and 11-12.

Figure 34:
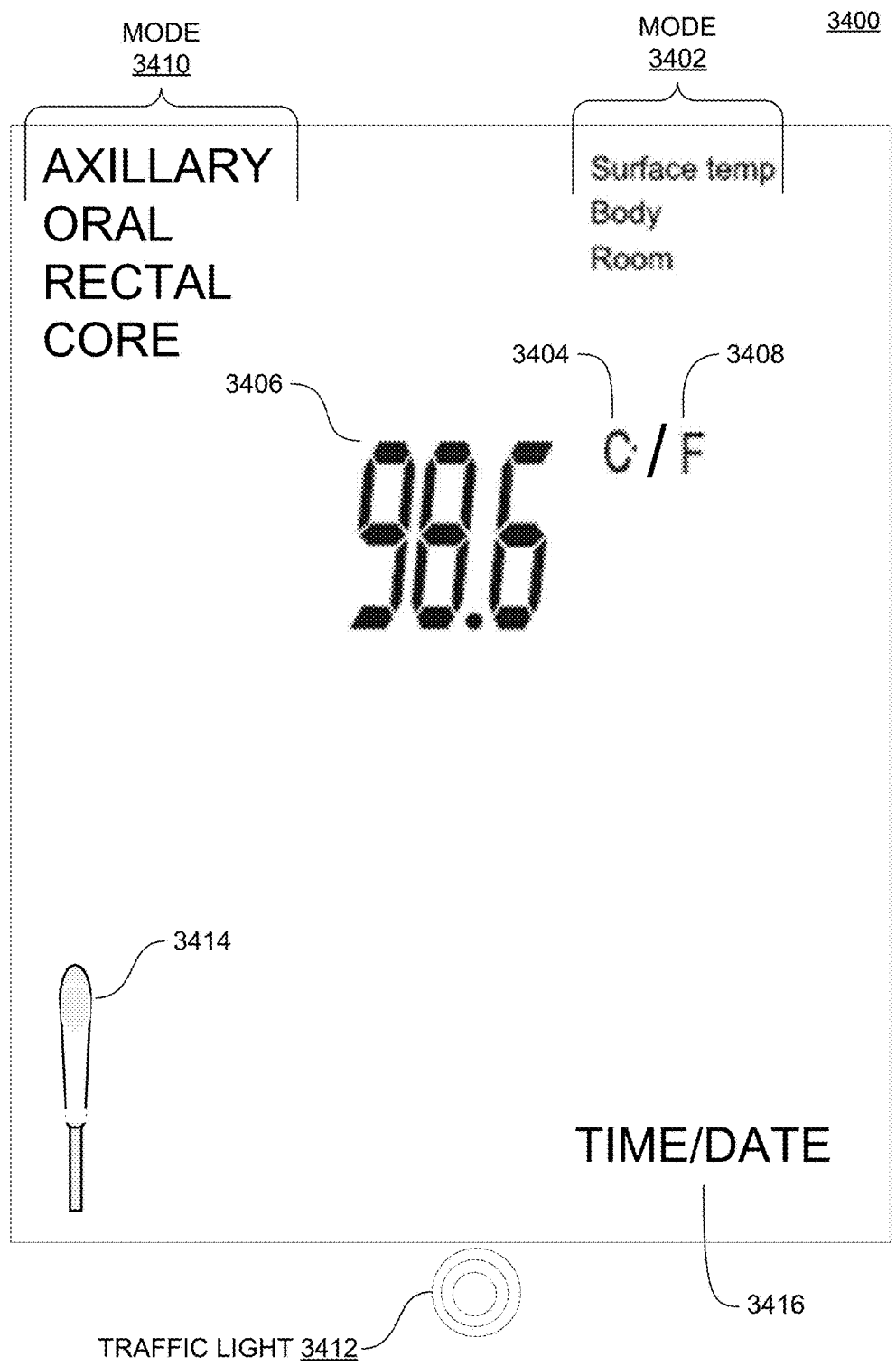
FIG. 34 is a representation of a display that is presented on the display device of apparatus in FIGS. 3-14 and 35-39, according to an implementation.

More specifically, to prevent or at least reduce heat transfer between the digital infrared sensor 308 and the microprocessor (102, 604 or 902) in some implementations the digital infrared sensor 308 is isolated on a separate PCB from the PCB that has the microprocessor (102, 604 or 902), as shown in FIG. 34, and the two PCBs are connected by only a connector that has 4 pins. The minimal connection of the single connector having 4 pins reduces heat transfer from the microprocessor (102, 604 or 902) to the digital infrared sensor 308 through the electrical connector and through transfer that would occur through the PCB material if the digital infrared sensor 308 and the microprocessor 302 were mounted on the same PCB.

In some implementations, the apparatus in FIG. 3-12 includes only one printed circuit board, in which case the printed circuit board includes the microprocessor 302 and the digital infrared sensor 308, non-touch electromagnetic sensor 602 or the analog infrared sensor 702 are mounted on the singular printed circuit board. In some implementations, the apparatus in FIG. 3-12 includes two printed circuit boards, such as a first printed circuit board and a second printed circuit board in which the microprocessor 302 is on the first printed circuit board and the digital infrared sensor 308, non-touch electromagnetic sensor 602 or the analog infrared sensor 702 are on the second printed circuit board. In some implementations, the apparatus in FIG. 3-12 includes only one display device 314, in which case the display device 314 includes not more than one display device 314. In some implementations, the display device 314 is a liquid-crystal diode (LCD) display device. In some implementations, the display device 314 is a light-emitting diode (LED) display device. In some implementations, the apparatus in FIG. 3-12 includes only one battery 304.

Digital Infrared Thermometer Method Implementations

In the previous section, apparatus of the operation of an implementation was described. In this section, the particular methods performed by FIGS. 3-5, 8 and 11-12 are described by reference to a series of flowcharts.

Figure 13:
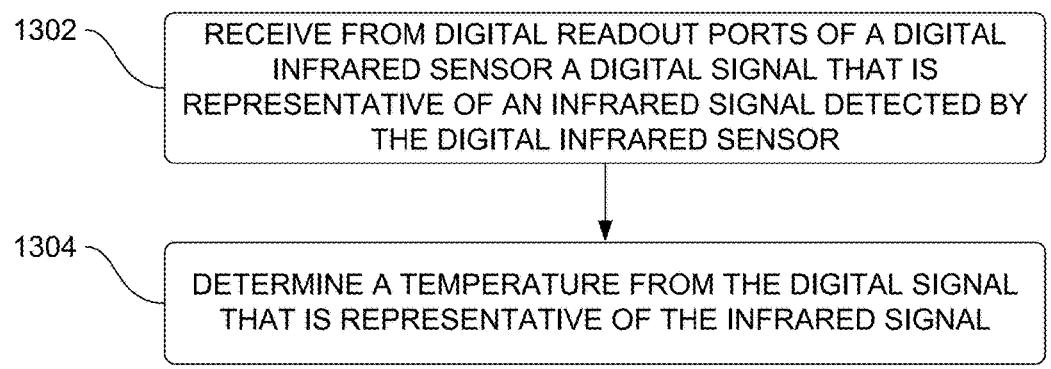
FIG. 13 is a flowchart of a method to determine a temperature from a digital infrared sensor, according to an implementation.

FIG. 13 is a flowchart of a method 1300 to determine a temperature from a digital infrared sensor, according to an implementation. Method 1300 includes receiving from the digital readout ports of a digital infrared sensor a digital signal that is representative of an infrared signal detected by the digital infrared sensor, at block 1302. No signal that is representative of the infrared signal is received from an analog infrared sensor.

Method 1300 also includes determining a temperature from the digital signal that is representative of the infrared signal, at block 1304.

Figure 14:
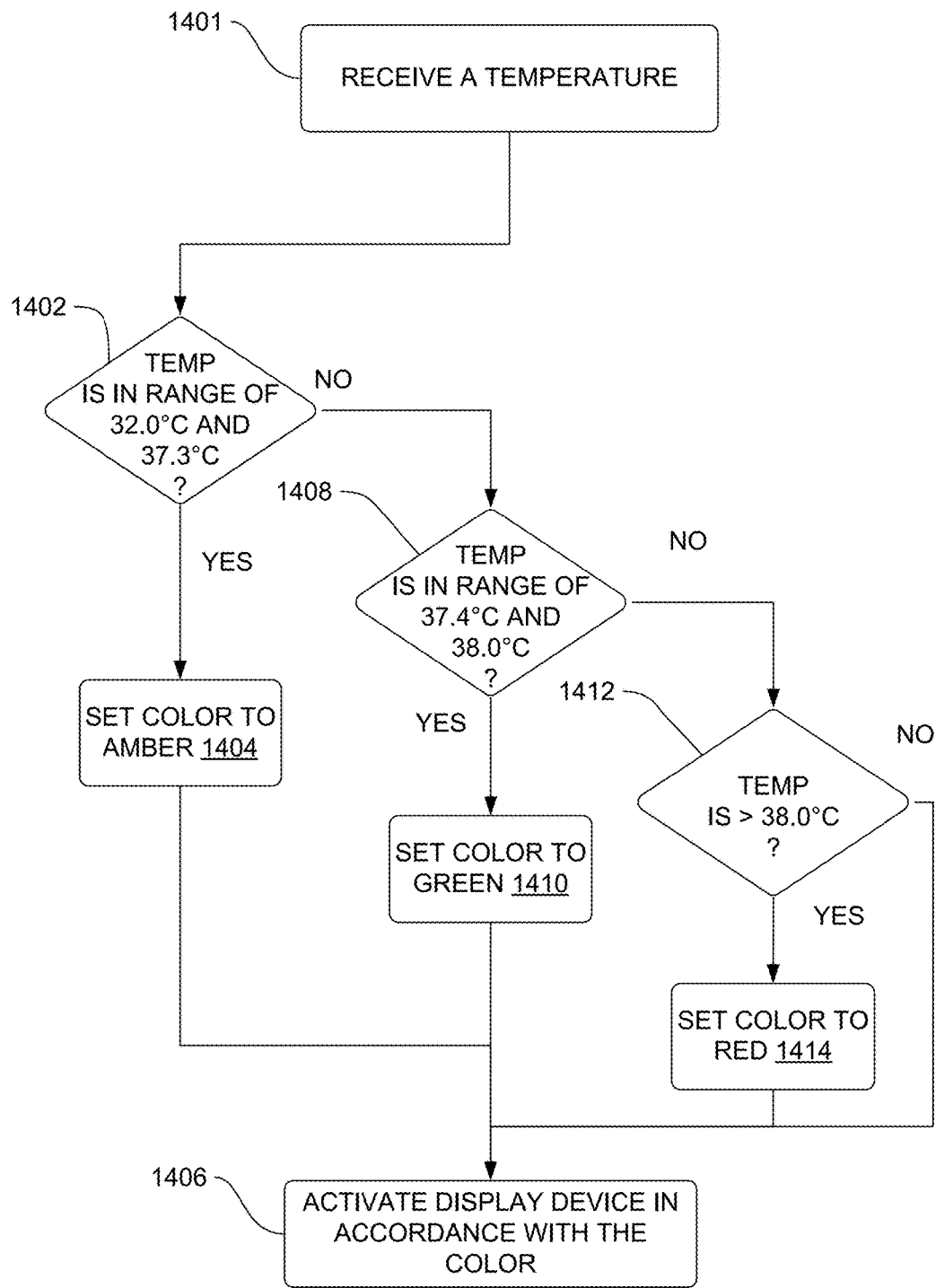
FIG. 14 is a flowchart of a method to display temperature color indicators, according to an implementation of three colors.

FIG. 14 is a flowchart of a method 1400 to display temperature color indicators, according to an implementation of three colors. Method 1400 provides color rendering in the color LED 3412 to indicate a general range of a temperature.

Method 1400 includes receiving a temperature (such as temperature 340 in FIG. 3), at block 1401.

Method 1400 also includes determining whether or not the temperature is in the range of 32.0° C. and 37.3° C., at block 1402. If the temperature is in the range of 32.0° C. and 37.3° C., then the color is set to 'amber' to indicate a temperature that is low, at block 1404 and the background of the color LED 3412 is activated in accordance with the color, at block 1406.

If the temperature is not the range of 32.0° C. and 37.3° C., then method 1400 also includes determining whether or not the temperature is in the range of 37.4° C. and 38.0° C., at block 1408. If the sensed temperature is in the range of 37.4° C. and 38.0° C., then the color is set to green to indicate no medical concern, at block 1410 and the background of the color LED 3412 is activated in accordance with the color, at block 1406.

If the temperature is not the range of 37.4° C. and 38.0° C., then method 1400 also includes determining whether or not the temperature is over 38.0° C., at block 1412. If the temperature is over 38.0° C., then the color is set to 'red' to indicate alert, at block 1412 and the background of the color LED 3412 is activated in accordance with the color, at block 1406.

Method 1400 assumes that temperature is in gradients of 10ths of a degree. Other temperature range boundaries are used in accordance with other gradients of temperature sensing.

In some implementations, some pixels in the color LED 3412 are activated as an amber color when the temperature is between 36.3° C. and 37.3° C. (97.3° F. to 99.1° F.), some pixels in the color LED 3412 are activated as a green when the temperature is between 37.4° C. and 37.9° C. (99.3° F. to 100.2° F.), some pixels in the color LED 3412 are activated as a red color when the temperature is greater than 38° C. (100.4° F.). In some implementations, the color LED 3412 is a backlit LCD screen 502 in FIG. 5 (which is easy to read in a dark room) and some pixels in the color LED 3412 are activated (remain lit) for about 5 seconds after the single button 306 is released. After the color LED 3412 has shut off, another temperature reading can be taken by the apparatus. The color change of the color LED 3412 is to alert the operator of the apparatus of a potential change of body temperature of the human or animal subject. The temperature reported on the display can be used for treatment decisions.

Figure 15:
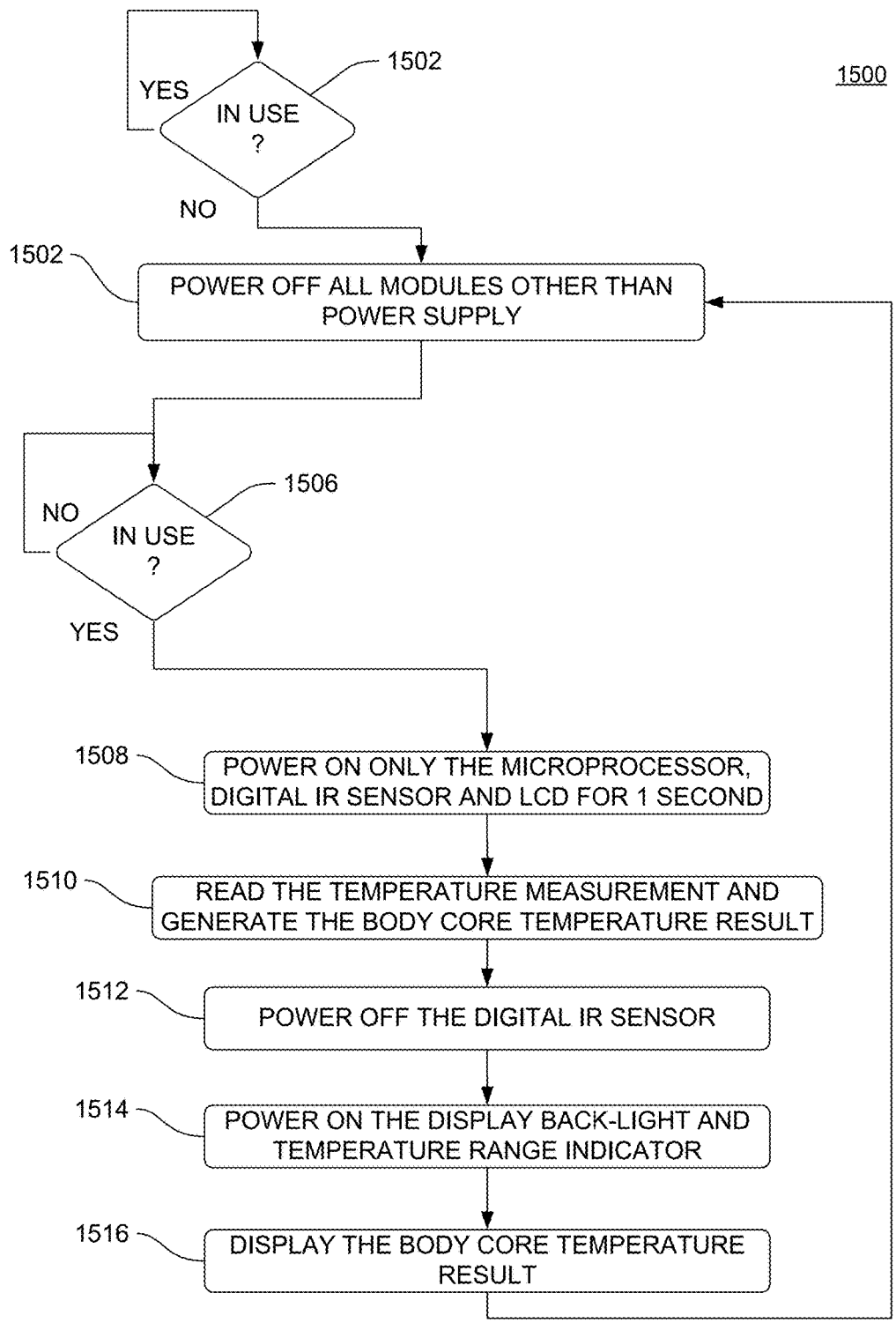
FIG. 15 is a flowchart of a method to manage power in a non-touch biologic detector or thermometer having a digital infrared sensor, according to an implementation.

FIG. 15 is a flowchart of a method 1500 to manage power in a non-touch device having a digital infrared sensor, according to an implementation. The method 1500 manages power in the device, such as non-touch biologic detectors and thermometers in FIG. 3-12, the non-touch thermometer 3500 in FIG. 35, the hand-held device 3200 in FIG. 32 and/or the computer 3300 in FIG. 33 in order to reduce heat pollution in the digital infrared sensor.

Figure 32:
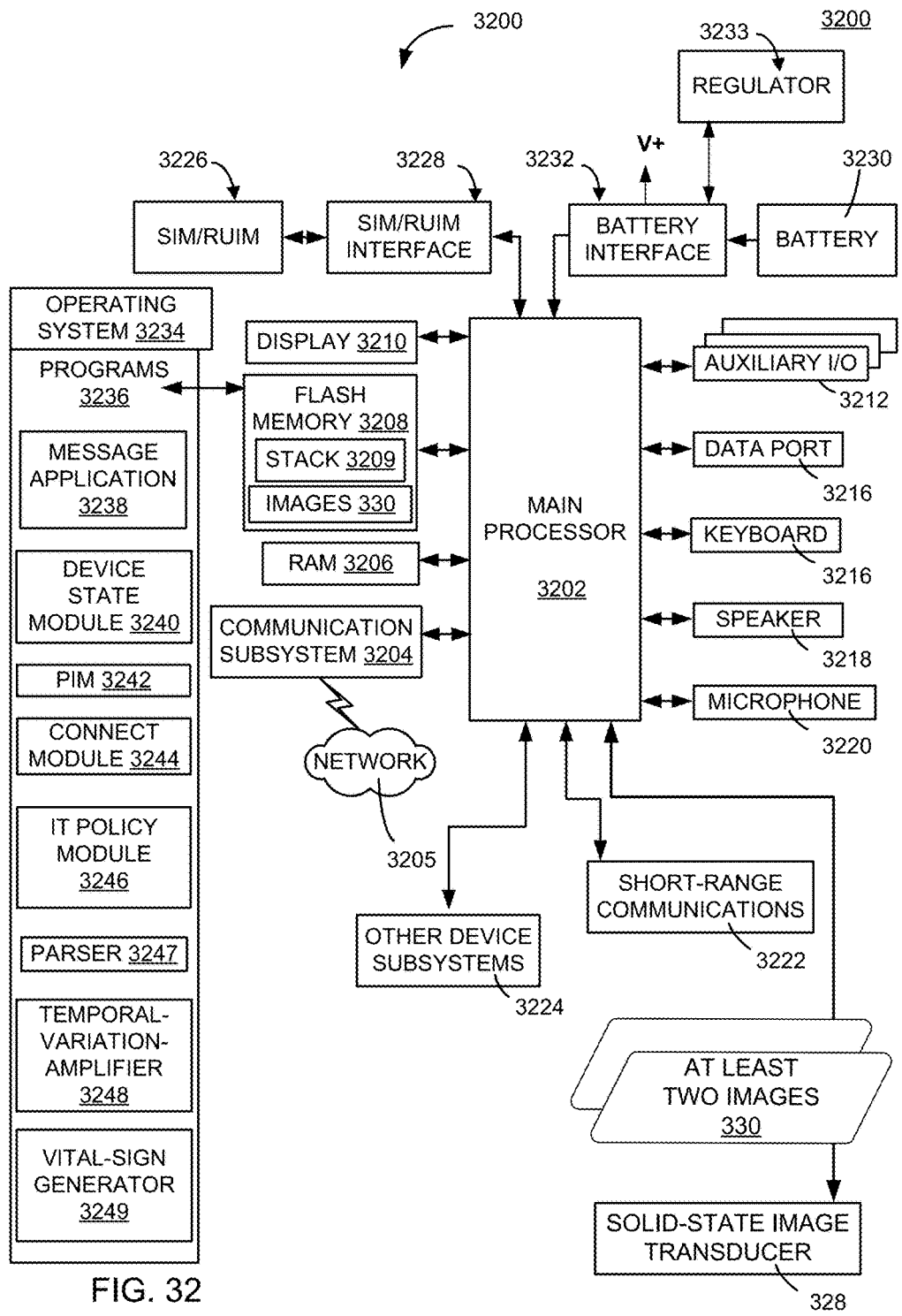
FIG. 32 is a block diagram of a hand-held device, according to an implementation.
Figure 33:
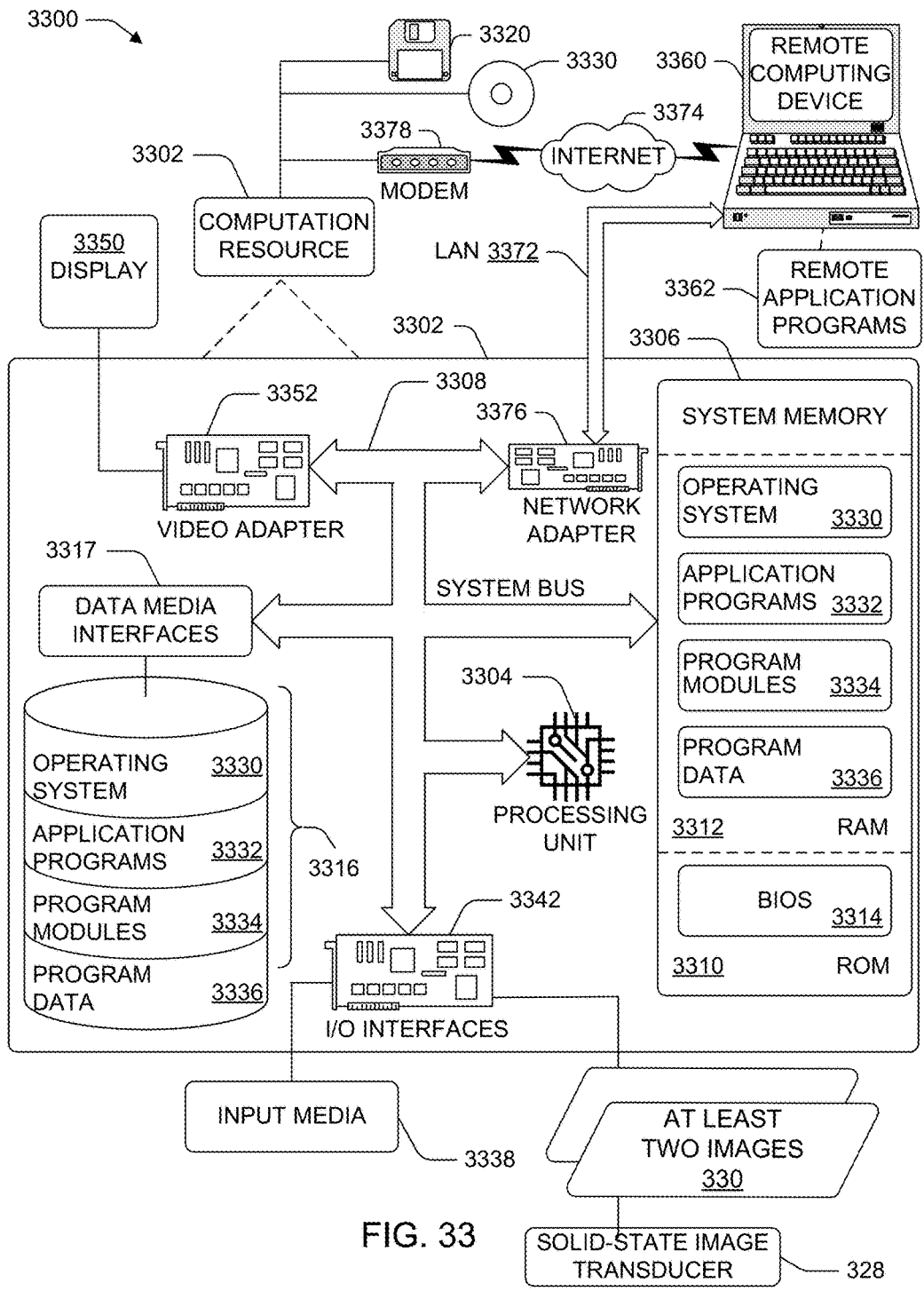
FIG. 33 illustrates an example of a computer environment, according to an implementation.
Figure 35:
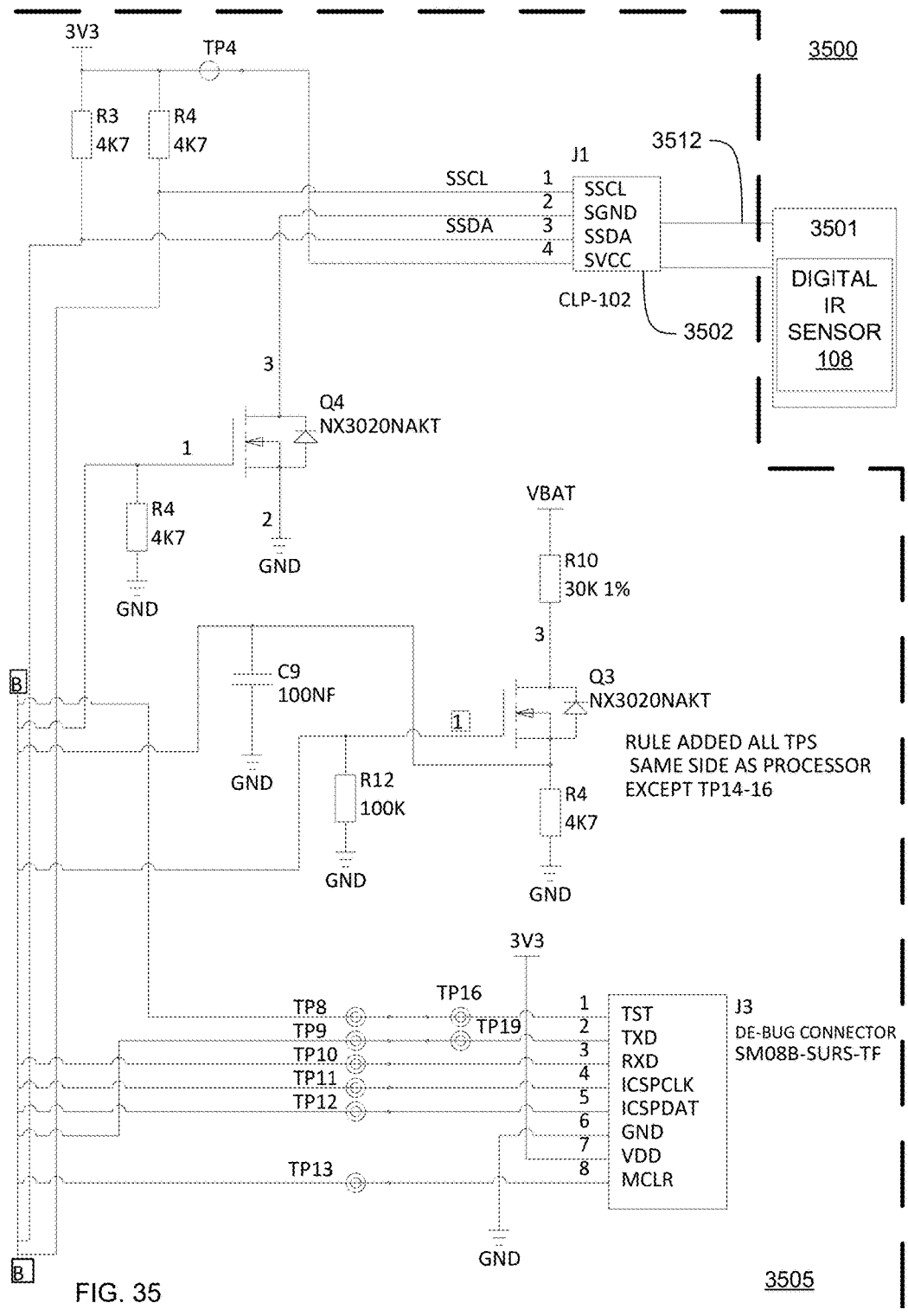
FIG. 35 is a portion of a schematic of a circuit board of a non-touch thermometer, according to an implementation.

To prevent or at least reduce heat transfer between the digital infrared sensor 308 and the microprocessor 302, microprocessor 604, microprocessor 3504 In FIG. 35, main processor 3202 in FIG. 32 or processing unit 3304 in FIG. 33, the components of the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33 are power controlled, i.e. the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33 turn sub-systems on and off, and the components are only activated when needed in the measurement and display process, which reduces power consumption and thus heat generation by the microprocessor 302, microprocessor 3504 In FIG. 35, main processor 3202 in FIG. 32 or processing unit 3304 in FIG. 33, of the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33, respectively. When not in use, at block 1502, the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33 are completely powered-off, at block 1504 (including the main PCB having the microprocessor 302, microprocessor 604, microprocessor 3504 In FIG. 35, main processor 3202 in FIG. 32 or processing unit 3304 in FIG. 33, and the sensor PCB having the digital infrared sensor 308) and not drawing any power, other than a power supply, i.e. a boost regulator, which has the effect that the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33 draw only drawing micro-amps from the battery 304 while in the off state, which is required for the life time requirement of 3 years of operation, but which also means that in the non-use state there is very little powered circuitry in the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33 and therefore very little heat generated in the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33.

When the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33 are started by the operator, at block 1506, only the microprocessor 302, microprocessor 604, microprocessor 3504 In FIG. 35, main processor 3202 in FIG. 32 or processing unit 3304 in FIG. 33, digital infrared sensor 308, and low power LCD (e.g. display device 314) are turned on for the first 1 second, at block 1508, to take the temperature measurement via the digital infrared sensor 308 and generate the body core temperature result via the microprocessor 302 in FIG. 3-12, microprocessor 3504 in FIG. 35, main processor 3202 in FIG. 32 or processing unit 3304 in FIG. 33, at block 1510. In this way, the main heat generating components (the LCD 314, the main PCB having the microprocessor 302 and the sensor PCB having the digital infrared sensor 308), the display back-light and the temperature range indicator (i.e. the traffic light indicator 3412) are not on and therefore not generating heat during the critical start-up and measurement process, no more than 1 second. After the measurement process of block 1510 has been completed, the digital infrared sensor 308 is turned off, at block 1512, to reduce current usage from the batteries and heat generation, and also the display back-light and temperature range indicators are turned on, at block 1514.

The measurement result is displayed for 4 seconds, at block 1516, and then the non-touch biologic detectors 300, 400, 500, 600, 700, 800, 900, 1000, 1100 and 1200 in FIG. 3-12, the non-touch thermometer 3500 in FIG. 35, the hand-held device 3200 in FIG. 32 and/or the computer 3300 in FIG. 33 are put in low power-off state, at block 1518.

In some implementations, of methods and apparatus of FIG. 3-39 an operator can take the temperature of a subject at multiple locations on a patient and from the temperatures at multiple locations to determine the temperature at a number of other locations of the subject. The multiple source points of which the electromagnetic energy is sensed are mutually exclusive to the location of the correlated temperature. In one example, the carotid artery source point on the subject and a forehead source point are mutually exclusive to the core temperature of the subject, an axillary temperature of the subject, a rectal temperature of the subject and an oral temperature of the subject.

The correlation of action can include a calculation based on Formula 1:

$$T_{body} = |f_{stb}(T_{surface\ temp} + f_{ntc}(T_{ntc})) + F4_{body}| \quad \text{Formula 1}$$

where $T_{body}$ is the temperature of a body or subject
where $f_{stb}$ is a mathematical formula of a surface of a body
where $f_{ntc}$ is mathematical formula for ambient temperature reading
where $T_{surface\ temp}$ is a surface temperature determined from the sensing.
where $T_{ntc}$ is an ambient air temperature reading
where $F4_{body}$ is a calibration difference in axillary mode, which is stored or set in a memory of the apparatus either during manufacturing or in the field. The apparatus also sets, stores and retrieves $F4_{oral}$, $F4_{core}$, and $F4_{rectal}$ in the memory.

$f_{ntc}(T_{ntc})$ is a bias in consideration of the temperature sensing mode. For example $f_{axillary}(T_{axillary})=0.2°$ C., $f_{oral}(T_{oral})=0.4°$ C., $f_{rectal}(T_{rectal})=0.5°$ C. and $f_{core}(T_{core})=0.3°$ C.

In some implementations, of determining a correlated body temperature of carotid artery by biasing a sensed temperature of a carotid artery, the sensed temperature is biased by $+0.5°$ C. to yield the correlated body temperature. In another example, the sensed temperature is biased by $-0.5°$ C. to yield the correlated body temperature. An example of correlating body temperature of a carotid artery follows:

$f_{ntc}(T_{ntc})=0.2°$ C. when $T_{ntc}=26.2°$ C. as retrieved from a data table for body sensing mode.

assumption: $T_{surface\ temp}=37.8°$ C.

$$T_{surface\ temp} + f_{ntc}(T_{ntc}) = 37.8°\ C. + 0.2°\ C. = 38.0°\ C.$$

$$f_{stb}(T_{surface\ temp} + f_{ntc}(T_{ntc})) = 38°\ C. + 1.4°\ C. = 39.4°\ C.$$

assumption: $F4_{body}=0.5°$ C.

$$T_{body} = |f_{stb}(T_{surface\ temp} + f_{ntc}(T_{ntc})) + F4_{body}| = |39.4°\ C. + 0.5\ C| = 39.9°\ C.$$

The correlated temperature for the carotid artery is 40.0° C.

In an example of correlating temperature of a plurality of external locations, such as a forehead and a carotid artery to an axillary temperature, first a forehead temperature is calculated using formula 1 as follows:

$f_{ntc}(T_{ntc})=0.2°$ C. when $T_{ntc}=26.2°$ C. as retrieved from a data table for axillary sensing mode.

assumption: $T_{surface\ temp}=37.8°$ C.

$$T_{surface\ temp} + f_{ntc}(T_{ntc}) = 37.8°\ C. + 0.2°\ C. = 38.0°\ C.$$

$$f_{stb}(T_{surface\ temp} + f_{ntc}(T_{ntc})) = 38°\ C. + 1.4°\ C. = 39.4°\ C.$$

assumption: $F4_{body}=0°$ C.

$$T_{body} = |f_{stb}(T_{surface\ temp} + f_{ntc}(T_{ntc})) + F4_{body}| = |39.4°\ C. + 0\ C| = 39.4°\ C.$$

And second, a carotid temperature is calculated using formula 1 as follows:

$f_{ntc}(T_{ntc})=0.6°$ C. when $T_{ntc}=26.4°$ C. as retrieved from a data table.

assumption: $T_{surface\ temp}=38.0°$ C.

$$T_{surface\ temp} + f_{ntc}(T_{ntc}) = 38.0°\ C. + 0.6°\ C. = 38.6°\ C.$$

$$f_{stb}(T_{surface\ temp} + f_{ntc}(T_{ntc})) = 38.6°\ C. + 1.4\ C = 40.0°\ C.$$

assumption: $F4_{body}=0°$ C.

$$T_{body} = |f_{stb}(T_{surface\ temp} + f_{ntc}(T_{ntc})) + F4_{body}| = |40.0°\ C. + 0\ C| = 40.0°\ C.$$

Thereafter the correlated temperature for the forehead (39.4° C.) and the correlated temperature for the carotid artery (40.0° C.) are averaged, yielding the final result of the scan of the forehead and the carotid artery as 39.7° C.

Vital Sign Motion Amplification Apparatus Implementations

Apparatus in FIG. 16-24 use spatial and temporal signal processing to generate vital signs from a series of digital images.

Figure 16:
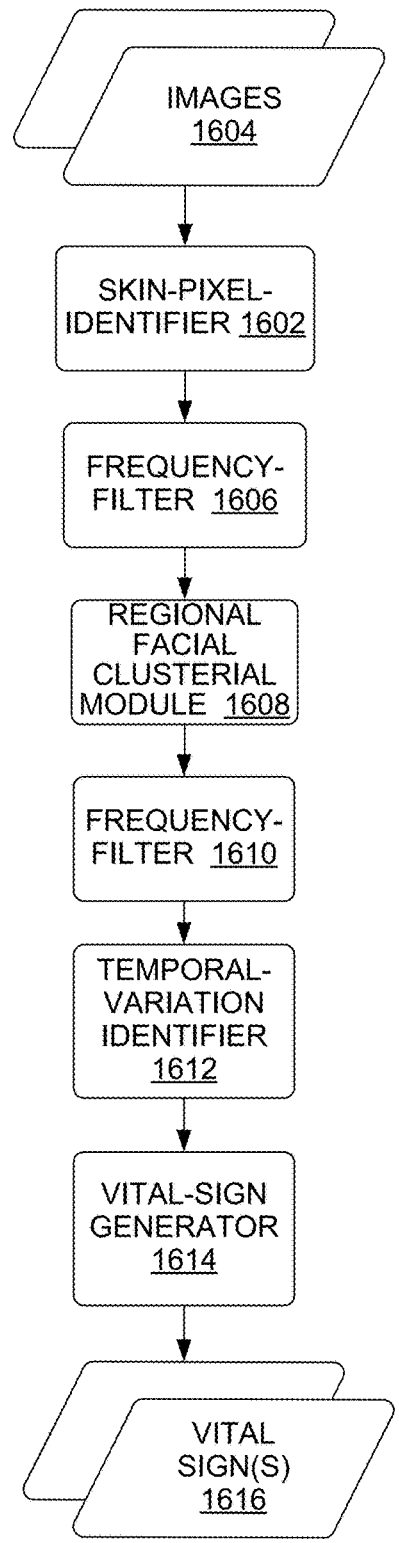
FIG. 16 is a block diagram of an apparatus of variation amplification, according to an implementation.

FIG. 16 is a block diagram of an apparatus 1600 of variation amplification, according to an implementation. Apparatus 1600 analyzes the temporal and spatial variations in digital images of an animal subject in order to generate and communicate biological vital signs.

Figure 25:
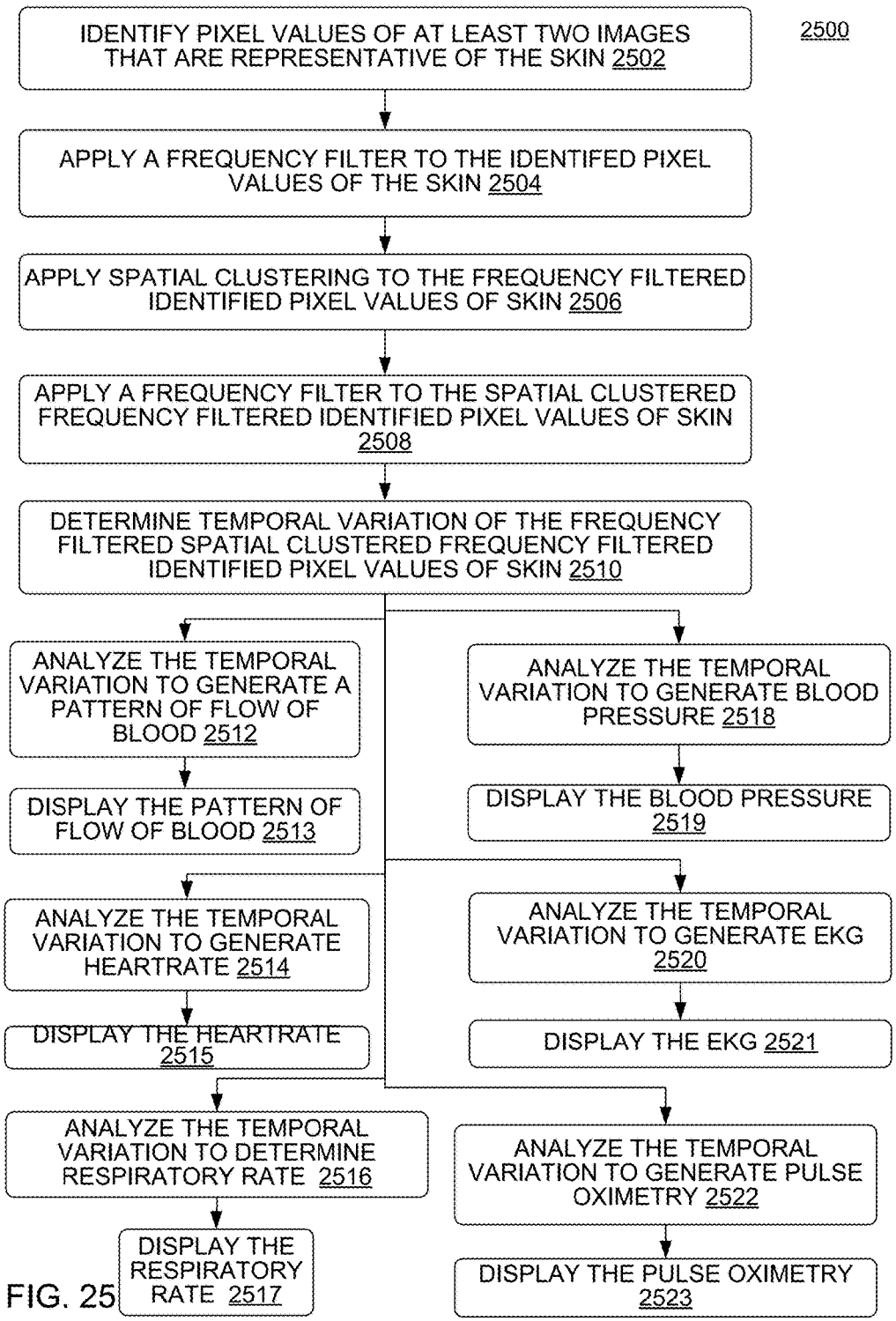
FIG. 25 is a flowchart of a method of variation amplification, according to an implementation.
Figure 26:
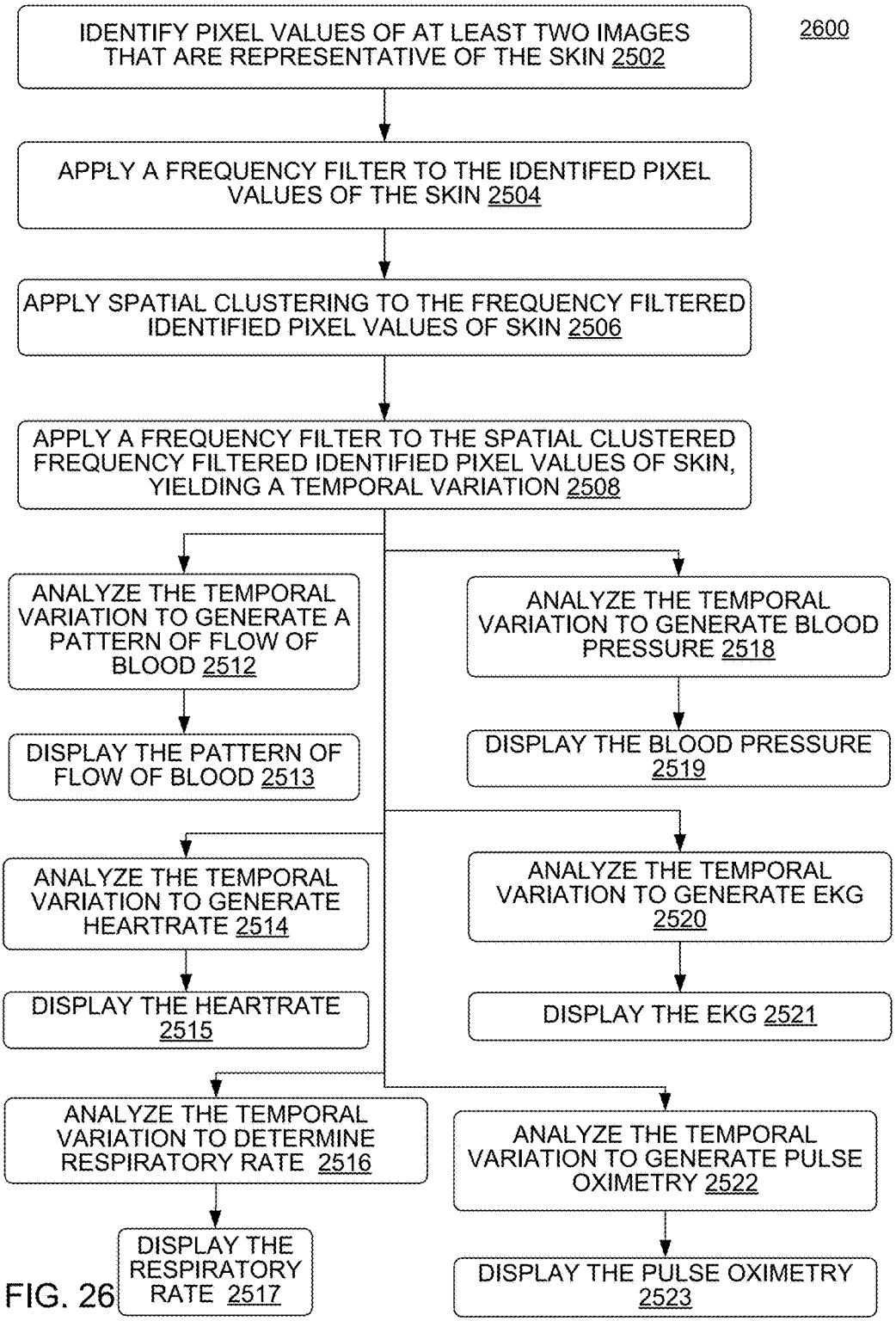
FIG. 26 is a flowchart of a method of variation amplification, according to an implementation that does not include a separate action of determining a temporal variation.
Figure 27:
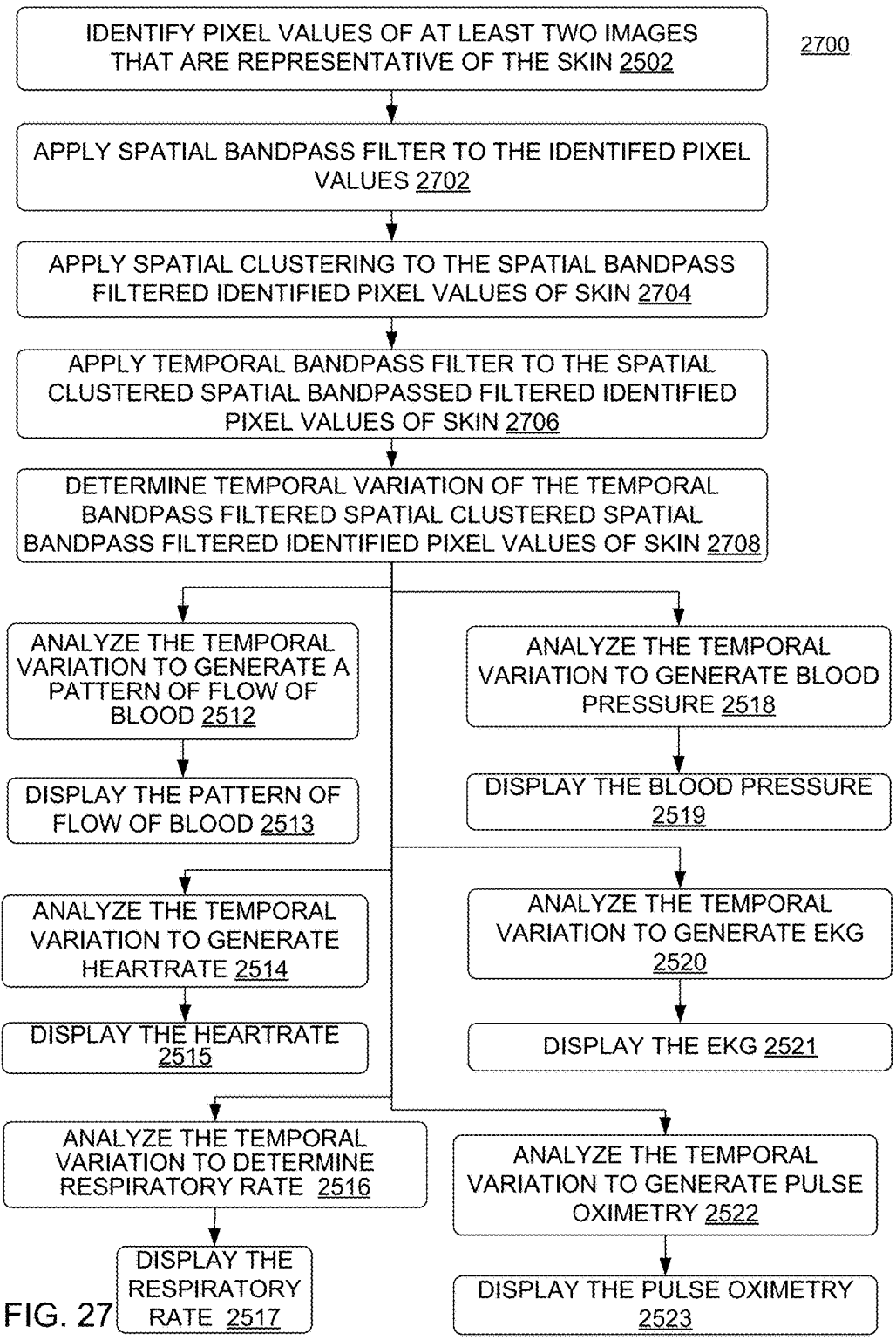
FIG. 27 is a flowchart of a method of variation amplification, according to an implementation.

In some implementations, apparatus 1600 includes a skin-pixel-identifier 1602 that identifies pixel values that are representative of the skin in two or more images 1604. In some implementations, the images 1604 are frames of a video. The skin-pixel-identifier 1602 performs block 2502 in FIG. 25. Some implementations of the skin-pixel-identifier 1602 perform an automatic seed point based clustering process on the two or more images 1604. In some implementations, apparatus 1600 includes a frequency filter 1606 that receives the output of the skin-pixel-identifier 1602 and applies a frequency filter to the output of the skin-pixel-identifier 1602. The frequency filter 1606 performs block 2504 in FIG. 25 to process the images 1604 in the frequency domain. In implementations where the apparatus in FIG. 16-24 or the methods in FIG. 25-27 are implemented on non-touch biologic detectors and thermometers in FIG. 3-10, the images 1604 in FIG. 16-24 are the images 330 in FIG. 3-12. In some implementations, the apparatus in FIG. 16-22 or the methods in FIG. 25-29 are implemented on the hand-held device 3200 in FIG. 32.

In some implementations, apparatus 1600 includes a regional facial clusterial module 1608 that applies spatial clustering to the output of the frequency filter 1606. The regional facial clusterial module 1608 performs block 2506 in FIG. 25. In some implementations, the regional facial clusterial module 1608 includes fuzzy clustering, k-means clustering, expectation-maximization process, Ward's apparatus or seed point based clustering.

In some implementations, apparatus 1600 includes a frequency-filter 1610 that applies a frequency filter to the output of the regional facial clusterial module 1608. The frequency-filter 1610 performs block 2508 in FIG. 25. In some implementations, the frequency-filter 1610 is a one-dimensional spatial Fourier Transform, a high pass filter, a low pass filter, a bandpass filter or a weighted bandpass filter. Some implementations of frequency-filter 1610 includes de-noising (e.g. smoothing of the data with a Gaussian filter). The skin-pixel-identifier 1602, the frequency filter 1606, the regional facial clusterial module 1608 and the frequency-filter 1610 amplify temporal variations (as a temporal-variation-amplifier) in the two or more images 1604.

In some implementations, apparatus 1600 includes a temporal-variation identifier 1612 that identifies temporal variation of the output of the frequency-filter 1610. Thus, the temporal variation represents temporal variation of the images 1604. The temporal-variation identifier 1612 performs block 2510 in FIG. 25.

In some implementations, apparatus 1600 includes a vital-sign generator 1614 that generates one or more vital sign(s) 1616 from the temporal variation. The vital sign(s) 1616 are displayed for review by a healthcare worker or stored in a volatile or nonvolatile memory for later analysis, or transmitted to other devices for analysis.

Fuzzy clustering a class of processes for cluster analysis in which the allocation of data points to clusters is not "hard" (all-or-nothing) but "fuzzy" in the same sense as fuzzy logic. Fuzzy logic being a form of many-valued logic which with reasoning that is approximate rather than fixed and exact. In fuzzy clustering, every point has a degree of belonging to clusters, as in fuzzy logic, rather than belonging completely to just one cluster. Thus, points on the edge of a cluster, may be in the cluster to a lesser degree than points in the center of cluster. Any point x has a set of coefficients giving the degree of being in the kth cluster $w_k(x)$. With fuzzy c-means, the centroid of a cluster is the mean of all points, weighted by a degree of belonging of each point to the cluster:

$$c_k = \frac{\sum_x w_k(x)^m x}{\sum_x w_k(x)}.$$

The degree of belonging, $w_k(x)$, is related inversely to the distance from x to the cluster center as calculated on the previous pass. The degree of belonging, $w_k(x)$ also depends on a parameter m that controls how much weight is given to the closest center.

k-means clustering is a process of vector quantization, originally from signal processing, that is popular for cluster analysis in data mining, k-means clustering partitions n observations into k clusters in which each observation belongs to the cluster with the nearest mean, serving as a prototype of the cluster. This results in a partitioning of the data space into Voronoi cells. A Voronoi Cell being a region within a Voronoi Diagram that is a set of points which is specified beforehand. A Voronoi Diagram is a technique of dividing space into a number of regions. k-means clustering uses cluster centers to model the data and tends to find clusters of comparable spatial extent, like K-means clustering, but each data point has a fuzzy degree of belonging to each separate cluster.

An expectation-maximization process is an iterative process for finding maximum likelihood or maximum a posteriori (MAP) estimates of parameters in statistical models, where the model depends on unobserved latent variables. The expectation-maximization iteration alternates between performing an expectation step, which creates a function for the expectation of the log-likelihood evaluated using the current estimate for the parameters, and a maximization step, which computes parameters maximizing the expected log-likelihood found on the expectation step. These parameter-estimates are then used to determine the distribution of the latent variables in the next expectation step.

The expectation maximization process seeks to find the maximization likelihood expectation of the marginal likelihood by iteratively applying the following two steps:

1. Expectation step (E step): Calculate the expected value of the log likelihood function, with respect to the conditional distribution of Z given X under the current estimate of the parameters $\theta^{(t)}$:

$$Q(\theta|\theta^{(t)}) = E_{Z|X,\theta^{(t)}}[\log L(\theta;X,Z)]$$

2. Maximization step (M step): find the parameter that maximizes this quantity:

$$\theta^{(t+1)} = \arg\max_\theta Q(\theta|\theta^{(t)})$$

Note that in typical models to which expectation maximization is applied:

1. The observed data points X may be discrete (taking values in a finite or countably infinite set) or continuous (taking values in an uncountably infinite set). There may in fact be a vector of observations associated with each data point.

2. The missing values (aka latent variables) Z are discrete, drawn from a fixed number of values, and there is one latent variable per observed data point.

3. The parameters are continuous, and are of two kinds: Parameters that are associated with all data points, and parameters associated with a particular value of a latent variable (i.e. associated with all data points whose corresponding latent variable has a particular value).

The Fourier Transform is an important image processing tool which is used to decompose an image into its sine and cosine components. The output of the transformation represents the image in the Fourier or frequency domain, while the input image is the spatial domain equivalent. In the Fourier domain image, each point represents a particular frequency contained in the spatial domain image.

The Discrete Fourier Transform is the sampled Fourier Transform and therefore does not contain all frequencies forming an image, but only a set of samples which is large enough to fully describe the spatial domain image. The number of frequencies corresponds to the number of pixels in the spatial domain image, i.e. the image in the spatial and Fourier domains are of the same size.

For a square image of size N×N, the two-dimensional DFT is given by:

$$F(k, l) = \sum_{i=0}^{N-1} \sum_{j=0}^{N-1} f(i, j) e^{-i2\pi\left(\frac{ki}{N} + \frac{lj}{N}\right)}$$

where f(a,b) is the image in the spatial domain and the exponential term is the basis function corresponding to each point F(k,l) in the Fourier space. The equation can be interpreted as: the value of each point F(k,l) is obtained by multiplying the spatial image with the corresponding base function and summing the result.

The basis functions are sine and cosine waves with increasing frequencies, i.e. F(0,0) represents the DC-component of the image which corresponds to the average brightness and F(N−1,N−1) represents the highest frequency.

A high-pass filter (HPF) is an electronic filter that passes high-frequency signals but attenuates (reduces the amplitude of) signals with frequencies lower than the cutoff frequency. The actual amount of attenuation for each frequency varies from filter to filter. A high-pass filter is usually modeled as a linear time-invariant system. A high-pass filter can also be used in conjunction with a low-pass filter to make a band-pass filter. The simple first-order electronic high-pass filter is implemented by placing an input voltage across the series combination of a capacitor and a resistor and using the voltage across the resistor as an output. The product of the resistance and capacitance (R×C) is the time constant (τ); the product is inversely proportional to the cutoff frequency $f_c$, that is:

$$f_c = \frac{1}{2\pi\tau} = \frac{1}{2\pi RC},$$

where $f_c$ is in hertz, τ is in seconds, R is in ohms, and C is in farads.

A low-pass filter is a filter that passes low-frequency signals and attenuates (reduces the amplitude of) signals with frequencies higher than the cutoff frequency. The actual amount of attenuation for each frequency varies depending on specific filter design. Low-pass filters are also known as high-cut filter, or treble cut filter in audio applications. A low-pass filter is the opposite of a high-pass filter. Low-pass filters provide a smoother form of a signal, removing the short-term fluctuations, and leaving the longer-term trend.

One simple low-pass filter circuit consists of a resistor in series with a load, and a capacitor in parallel with the load. The capacitor exhibits reactance, and blocks low-frequency signals, forcing the low-frequency signals through the load instead. At higher frequencies the reactance drops, and the capacitor effectively functions as a short circuit. The combination of resistance and capacitance gives the time constant of the filter. The break frequency, also called the turnover frequency or cutoff frequency (in hertz), is determined by the time constant.

A band-pass filter is a device that passes frequencies within a certain range and attenuates frequencies outside that range. These filters can also be created by combining a low-pass filter with a high-pass filter. Bandpass is an adjective that describes a type of filter or filtering process; bandpass is distinguished from passband, which refers to the actual portion of affected spectrum. Hence, a dual bandpass filter has two passbands. A bandpass signal is a signal containing a band of frequencies not adjacent to zero frequency, such as a signal that comes out of a bandpass filter.

Figure 17:
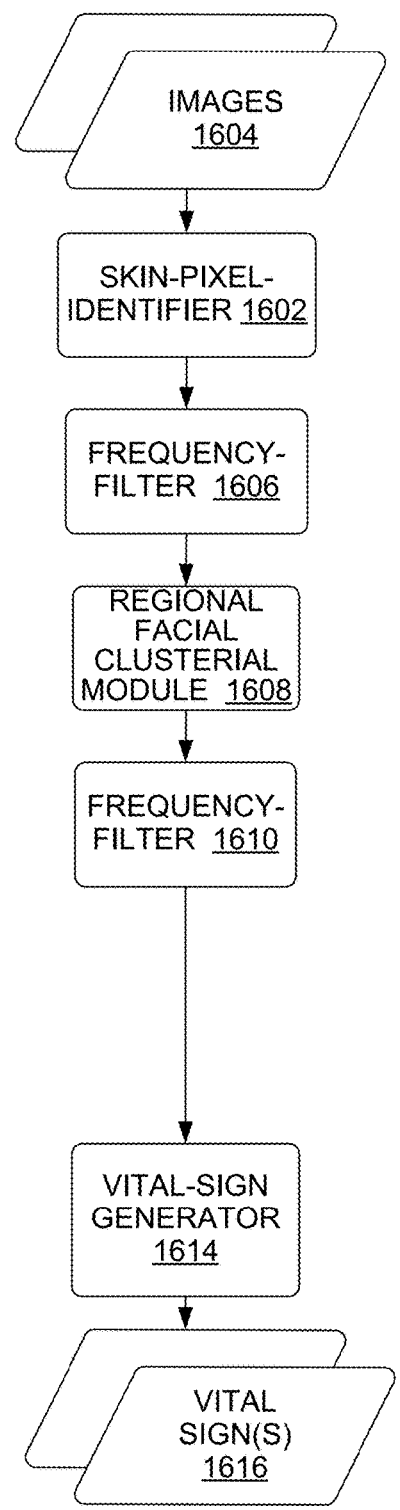
FIG. 17 is a block diagram of an apparatus of variation amplification, according to an implementation.

FIG. 17 is a block diagram of an apparatus 1700 of variation amplification, according to an implementation. Apparatus 1700 analyzes the temporal and spatial variations in digital images of an animal subject in order to generate and communicate biological vital signs.

In some implementations, apparatus 1700 includes a skin-pixel-identifier 1602 that identifies pixel values that are representative of the skin in two or more images 1604. The skin-pixel-identifier 1602 performs block 2502 in FIG. 25. Some implementations of the skin-pixel-identifier 1602 performs an automatic seed point based clustering process on the least two images 1604.

In some implementations, apparatus 1700 includes a frequency filter 1606 that receives the output of the skin-pixel-identifier 1602 and applies a frequency filter to the output of the skin-pixel-identifier 1602. The frequency filter 1606 performs block 2504 in FIG. 25 to process the images 1604 in the frequency domain.

In some implementations, apparatus 1700 includes a regional facial clusterial module 1608 that applies spatial clustering to the output of the frequency filter 1606. The regional facial clusterial module 1608 performs block 2506 in FIG. 25. In some implementations, the regional facial clusterial module 1608 includes fuzzy clustering, k-means clustering, expectation-maximization process, Ward's apparatus or seed point based clustering.

In some implementations, apparatus 1700 includes a frequency-filter 1610 that applies a frequency filter to the output of the regional facial clusterial module 1608, to generate a temporal variation. The frequency-filter 1610 performs block 2508 in FIG. 25. In some implementations, the frequency-filter 1610 is a one-dimensional spatial Fourier Transform, a high pass filter, a low pass filter, a bandpass filter or a weighted bandpass filter. Some implementations of frequency-filter 1610 includes de-noising (e.g. smoothing of the data with a Gaussian filter). The skin-pixel-identifier 1602, the frequency filter 1606, the regional facial clusterial module 1608 and the frequency-filter 1610 amplify temporal variations in the two or more images 1604.

In some implementations, apparatus 1700 includes a vital-sign generator 1614 that generates one or more vital sign(s) 1616 from the temporal variation. The vital sign(s) 1616 are displayed for review by a healthcare worker or stored in a volatile or nonvolatile memory for later analysis, or transmitted to other devices for analysis.

Figure 18:
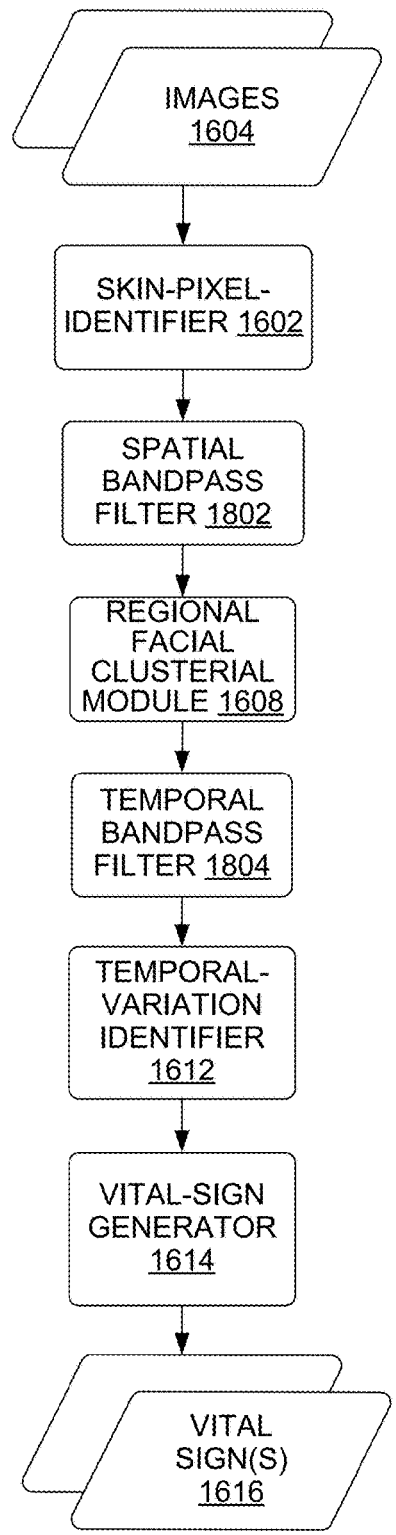
FIG. 18 is a block diagram of an apparatus of variation amplification, according to an implementation.

FIG. 18 is a block diagram of an apparatus 1800 of variation amplification, according to an implementation.

Apparatus 1800 analyzes the temporal and spatial variations in digital images of an animal subject in order to generate and communicate biological vital signs.

In some implementations, apparatus 1800 includes a skin-pixel-identifier 1602 that identifies pixel values that are representative of the skin in two or more images 1604. The skin-pixel-identifier 1602 performs block 2502 in FIG. 25. Some implementations of the skin-pixel-identifier 1602 performs an automatic seed point based clustering process on the least two images 1604.

In some implementations, apparatus 1800 includes a spatial bandpass filter 1802 that receives the output of the skin-pixel-identifier 1602 and applies a spatial bandpass filter to the output of the skin-pixel-identifier 1602.

In some implementations, apparatus 1800 includes a regional facial clusterial module 1608 that applies spatial clustering to the output of the frequency filter 1606. In some implementations, the regional facial clusterial module 1608 includes fuzzy clustering, k-means clustering, expectation-maximization process, Ward's apparatus or seed point based clustering.

In some implementations, apparatus 1800 includes a temporal bandpass filter 1804 that applies a frequency filter to the output of the regional facial clusterial module 1608. In some implementations, the temporal bandpass filter 1804 is a one-dimensional spatial Fourier Transform, a high pass filter, a low pass filter, a bandpass filter or a weighted bandpass filter. Some implementations of temporal bandpass filter 1804 includes de-noising (e.g. smoothing of the data with a Gaussian filter).

The skin-pixel-identifier 1602, the spatial bandpass filter 1802, the regional facial clusterial module 1608 and the temporal bandpass filter 1804 amplify temporal variations in the two or more images 1604.

In some implementations, apparatus 1800 includes a temporal-variation identifier 1612 that identifies temporal variation of the output of the frequency-filter 1610. Thus, the temporal variation represents temporal variation of the images 1604.

In some implementations, apparatus 1800 includes a vital-sign generator 1614 that generates one or more vital sign(s) 1616 from the temporal variation. The vital sign(s) 1616 are displayed for review by a healthcare worker or stored in a volatile or nonvolatile memory for later analysis, or transmitted to other devices for analysis.

Figure 19:
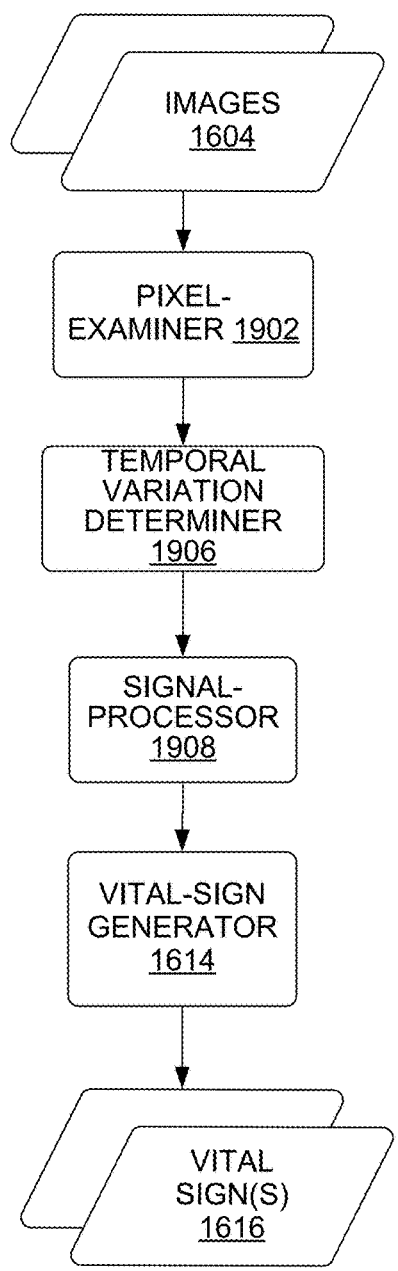
FIG. 19 is a block diagram of an apparatus of variation amplification, according to an implementation.

FIG. 19 is a block diagram of an apparatus 1900 of variation amplification, according to an implementation.

In some implementations, apparatus 1900 includes a pixel-examiner 1902 that examines pixel values of two or more images 1604.

In some implementations, apparatus 1900 includes a temporal variation determiner 1906 that determines a temporal variation of examined pixel values.

In some implementations, apparatus 1900 includes a signal-processor 1908 that applies signal processing to the pixel value temporal variation, generating an amplified temporal variation. The signal processing amplifies the temporal variation, even when the temporal variation is small. In some implementations, the signal processing performed by signal-processor 1908 is temporal bandpass filtering that analyzes frequencies over time. In some implementations, the signal processing performed by signal-processor 1908 is spatial processing that removes noise. Apparatus 1900 amplifies only small temporal variations in the signal-processing module.

In some implementations, apparatus 1800 includes a vital-sign generator 1614 that generates one or more vital sign(s) 1616 from the temporal variation. The vital sign(s) 1616 are displayed for review by a healthcare worker or stored in a volatile or nonvolatile memory for later analysis, or transmitted to other devices for analysis.

While apparatus 1900 can process large temporal variations, an advantage in apparatus 1900 is provided for small temporal variations. Therefore apparatus 1900 is most effective when the two or more images 1604 have small temporal variations between the two or more images 1604. In some implementations, a vital sign is generated from the amplified temporal variations of the two or more images 1604 from the signal-processor 1908.

Figure 20:
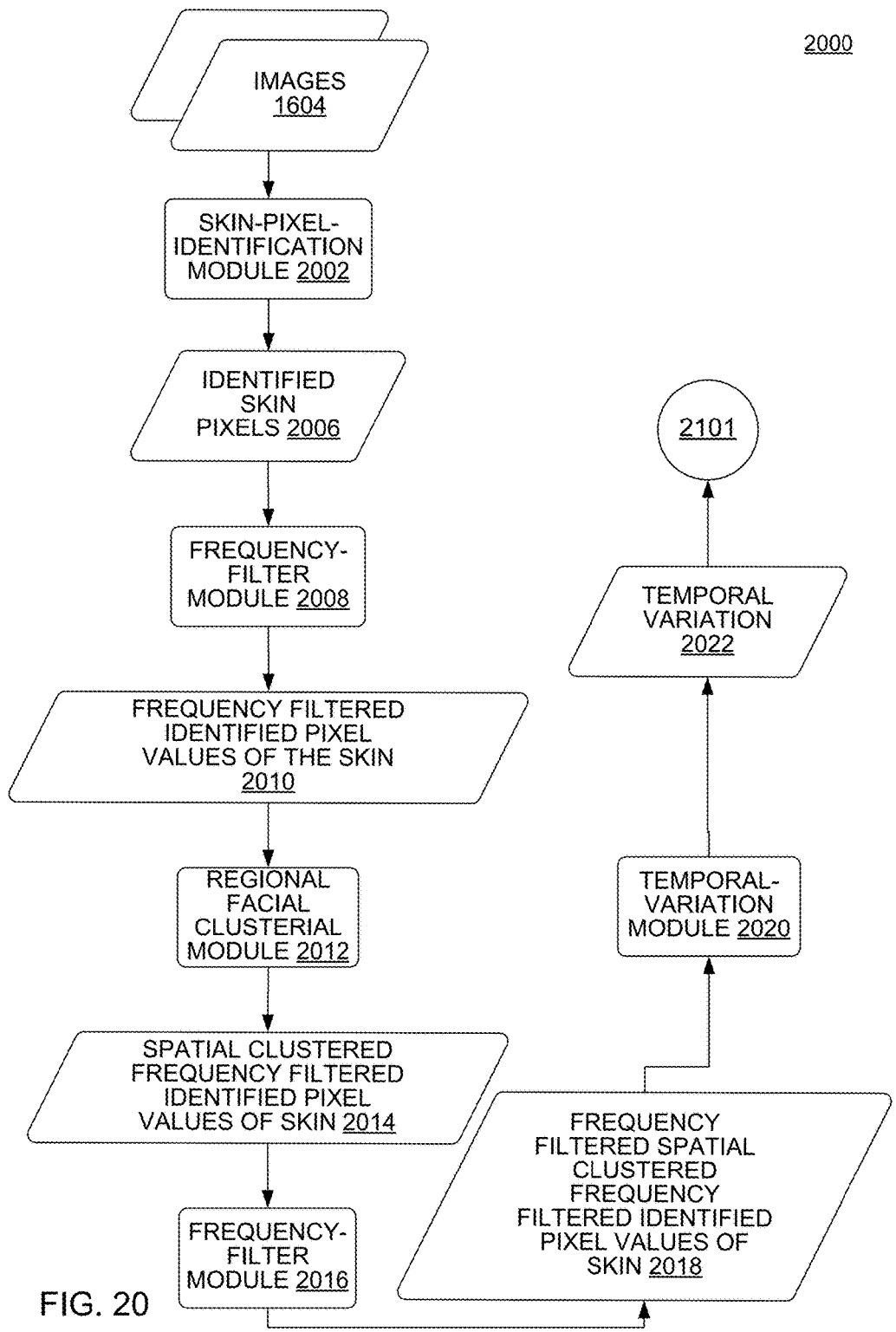
FIG. 20 is a block diagram of an apparatus of variation amplification, according to an implementation.

FIG. 20 is a block diagram of an apparatus 2000 of variation amplification, according to an implementation. Apparatus 2000 analyzes the temporal and spatial variations in digital images of an animal subject in order to generate and communicate biological vital signs.

In some implementations, apparatus 2000 includes a skin-pixel-identification module 2002 that identifies pixel values 2006 that are representative of the skin in two or more images 2004. The skin-pixel-identification module 2002 performs block 2502 in FIG. 25. Some implementations of the skin-pixel-identification module 2002 perform an automatic seed point based clustering process on the least two images 2004.

In some implementations, apparatus 2000 includes a frequency-filter module 2008 that receives the identified pixel values 2006 that are representative of the skin and applies a frequency filter to the identified pixel values 2006. The frequency-filter module 2008 performs block 2504 in FIG. 25 to process the images 1604 in the frequency domain. Each of the images 1604 is Fourier transformed, multiplied with a filter function and then re-transformed into the spatial domain. Frequency filtering is based on the Fourier Transform. The operator takes an image 1604 and a filter function in the Fourier domain. The image 1604 is then multiplied with the filter function in a pixel-by-pixel fashion using the formula:

$$G(k,l)=F(k,l)H(k,l)$$

where F(k,l) is the input image 1604 of identified pixel values 2006 in the Fourier domain, H(k,l) the filter function and G(k,l) is the filtered image 2010. To obtain the resulting image in the spatial domain, G(k,l) is re-transformed using the inverse Fourier Transform. In some implementations, the frequency-filter module 2008 is a two-dimensional spatial Fourier Transform, a high pass filter, a low pass filter, a bandpass filter or a weighted bandpass filter.

In some implementations, apparatus 2000 includes a spatial-cluster module 2012 that applies spatial clustering to the frequency filtered identified pixel values of skin 2010, generating spatial clustered frequency filtered identified pixel values of skin 2014. The spatial-cluster module 2012 performs block 2506 in FIG. 25. In some implementations, the spatial-cluster module 2012 includes fuzzy clustering, k-means clustering, expectation-maximization process, Ward's apparatus or seed point based clustering.

In some implementations, apparatus 2000 includes a frequency-filter module 2016 that applies a frequency filter to the spatial clustered frequency filtered identified pixel values of skin 2014, which generates frequency filtered spatial clustered frequency filtered identified pixel values of skin 2018. The frequency-filter module 2016 performs block 2508 in FIG. 25. In some implementations, the frequency-filter module 2016 is a one-dimensional spatial Fourier Transform, a high pass filter, a low pass filter, a bandpass filter or a weighted bandpass filter. Some implementations of frequency-filter module 2016 includes de-noising (e.g. smoothing of the data with a Gaussian filter).

The skin-pixel-identification module 2002, the frequency-filter module 2008, the spatial-cluster module 2012 and the frequency-filter module 2016 amplify temporal variations in the two or more images 1604.

In some implementations, apparatus 2000 includes a temporal-variation module 2020 that determines temporal variation 2022 of the frequency filtered spatial clustered frequency filtered identified pixel values of skin 2018. Thus, temporal variation 2022 represents temporal variation of the images 1604. The temporal-variation module 2020 performs block 2510 in FIG. 25.

Figure 21:
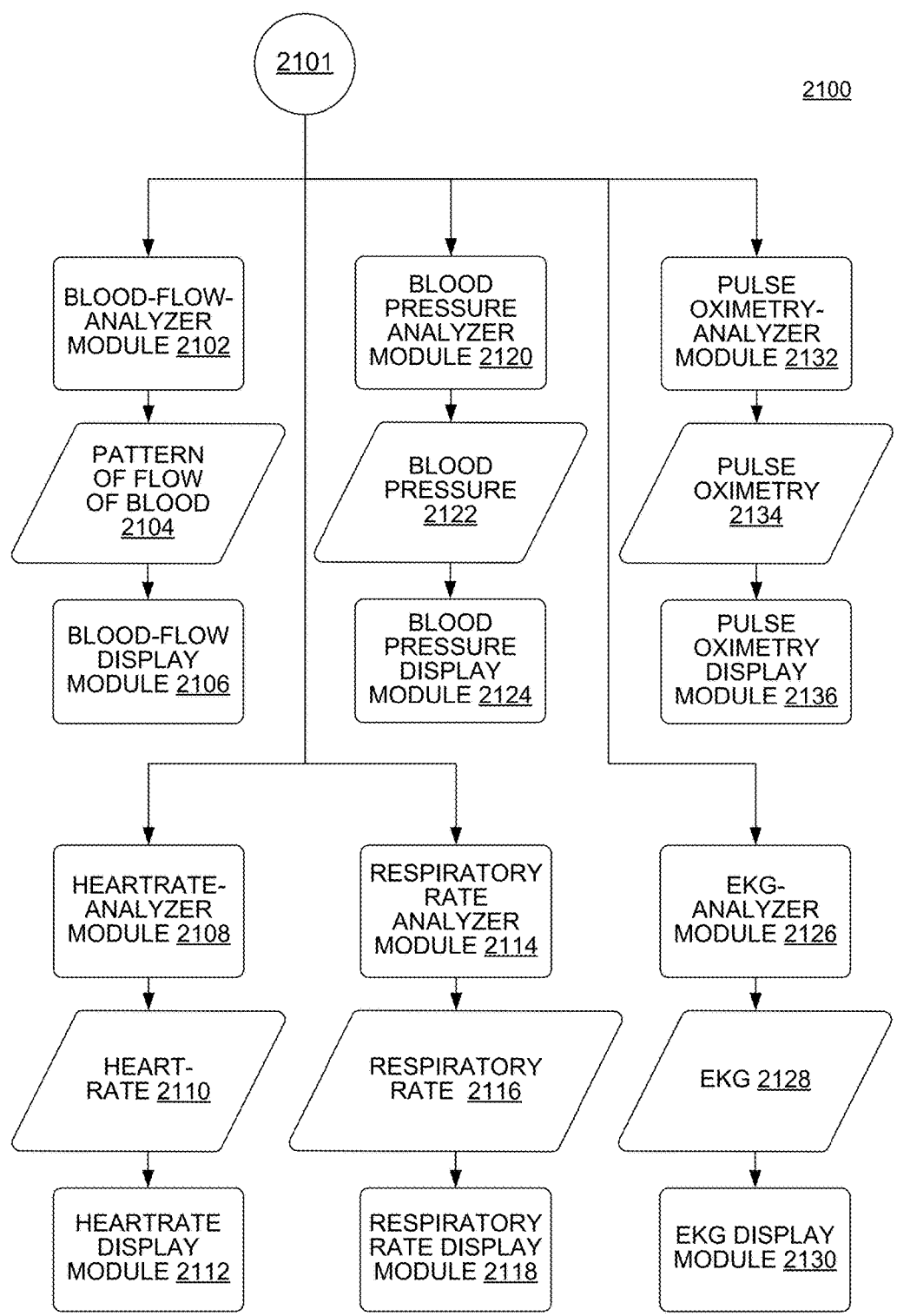
FIG. 21 is a block diagram of an apparatus to generate and present any one of a number of biological vital signs from amplified motion, according to an implementation.

FIG. 21 is a block diagram of an apparatus 2100 to generate and present any one of a number of biological vital signs from amplified motion, according to an implementation.

In some implementations, apparatus 2100 includes a blood-flow-analyzer module 2102 that analyzes a temporal variation to generate a pattern of flow of blood 2104. One example of the temporal variation is temporal variation 2022 in FIG. 20. In some implementations, the pattern flow of blood 2104 is generated from motion changes in the pixels and the temporal variation of color changes in the skin of the images 1604. In some implementations, apparatus 2100 includes a blood-flow display module 2106 that displays the pattern of flow of blood 2104 for review by a healthcare worker.

In some implementations, apparatus 2100 includes a heartrate-analyzer module 2108 that analyzes the temporal variation to generate a heartrate 2110. In some implementations, the heartrate 2110 is generated from the frequency spectrum of the temporal signal in a frequency range for heart beats, such as (0-10 Hertz). In some implementations, apparatus 2100 includes a heartrate display module 2112 that displays the heartrate 2110 for review by a healthcare worker.

In some implementations, apparatus 2100 includes a respiratory rate-analyzer module 2114 that analyzes the temporal variation to determine a respiratory rate 2116. In some implementations, the respiratory rate 2116 is generated from the motion of the pixels in a frequency range for respiration (0-5 Hertz). In some implementations, apparatus 2100 includes respiratory rate display module 2118 that displays the respiratory rate 2116 for review by a healthcare worker.

In some implementations, apparatus 2100 includes a blood-pressure analyzer module 2120 that analyzes the temporal variation to a generate blood pressure 2122. In some implementations, the blood-pressure analyzer module 2120 generates the blood pressure 2122 by analyzing the motion of the pixels and the color changes based on a clustering process and potentially temporal data. In some implementations, apparatus 2100 includes a blood pressure display module 2124 that displays the blood pressure 2122 for review by a healthcare worker.

In some implementations, apparatus 2100 includes an EKG analyzer module 2126 that analyzes the temporal variation to generate an EKG 2128. In some implementations, apparatus 2100 includes an EKG display module 2130 that displays the EKG 2128 for review by a healthcare worker.

In some implementations, apparatus 2100 includes a pulse oximetry analyzer module 2132 that analyzes the temporal variation to generate pulse oximetry 2134. In some implementations, the pulse oximetry analyzer module 2132 generates the pulse oximetry 2134 by analyzing the temporal color changes based in conjunction with the k-means clustering process and potentially temporal data. In some implementations, apparatus 2100 includes a pulse oximetry display module 2136 that displays the pulse oximetry 2134 for review by a healthcare worker.

Figure 22:
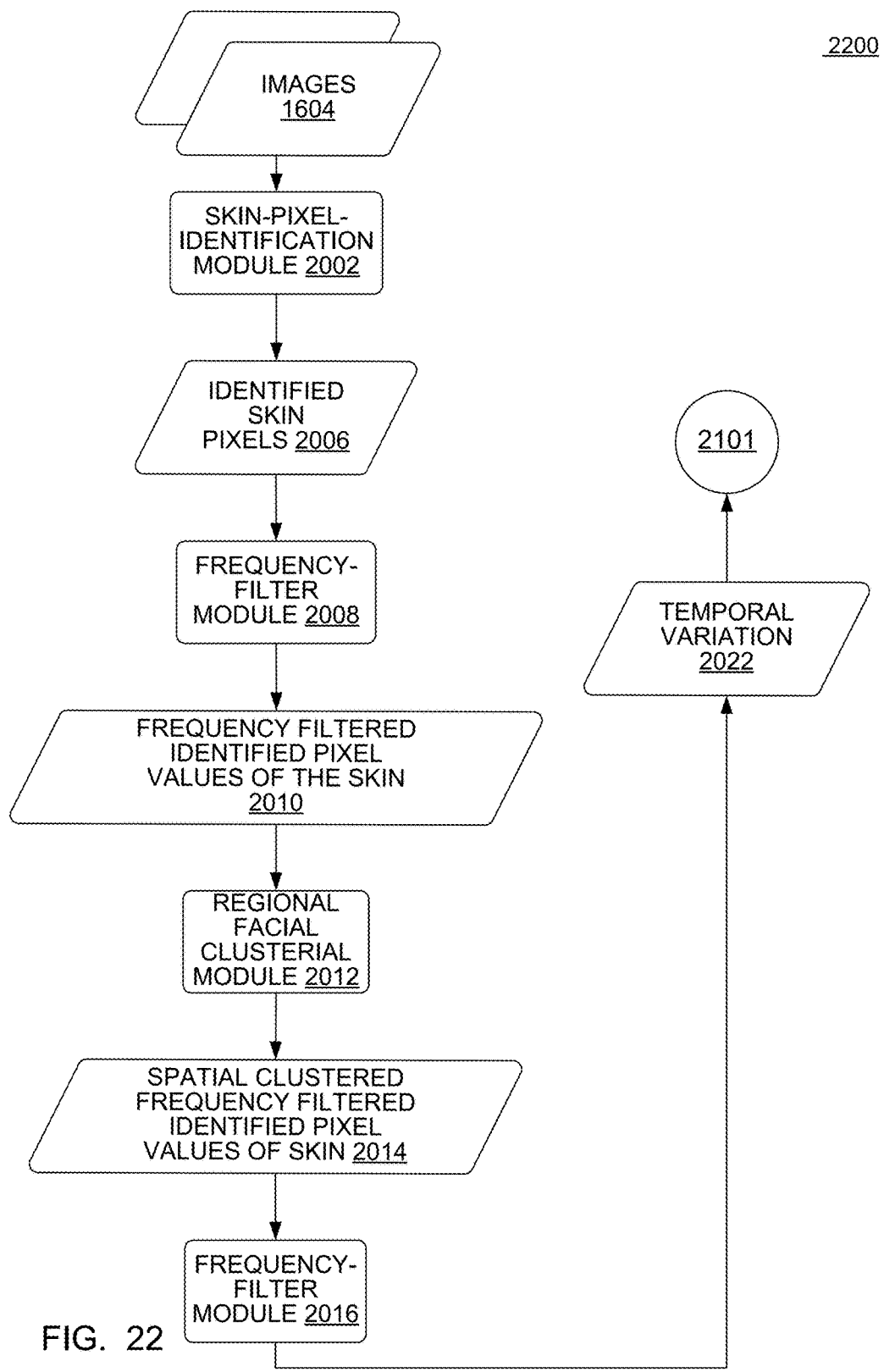
FIG. 22 is a block diagram of an apparatus of variation amplification, according to an implementation.

FIG. 22 is a block diagram of an apparatus 2200 of variation amplification, according to an implementation. Apparatus 2200 analyzes the temporal and spatial variations in digital images of an animal subject in order to generate and communicate biological vital signs.

In some implementations, apparatus 2200 includes a skin-pixel-identification module 2002 that identifies pixel values 2006 that are representative of the skin in two or more images 1604. The skin-pixel-identification module 2002 performs block 2502 in FIG. 25. Some implementations of the skin-pixel-identification module 2002 perform an automatic seed point based clustering process on the least two images 1604.

In some implementations, apparatus 2200 includes a frequency-filter module 2008 that receives the identified pixel values 2006 that are representative of the skin and applies a frequency filter to the identified pixel values 2006. The frequency-filter module 2008 performs block 2504 in FIG. 25 to process the images 1604 in the frequency domain. Each of the images 1604 is Fourier transformed, multiplied with a filter function and then re-transformed into the spatial domain. Frequency filtering is based on the Fourier Transform. The operator takes an image 1604 and a filter function in the Fourier domain. The image 1604 is then multiplied with the filter function in a pixel-by-pixel fashion using the formula: $G(k,l) = F(k,l)H(k,l)$ where $F(k,l)$ is the input image 1604 of identified pixel values 2006 in the Fourier domain, $H(k,l)$ the filter function and $G(k,l)$ is the filtered image 2010. To obtain the resulting image in the spatial domain, $G(k,l)$ is re-transformed using the inverse Fourier Transform. In some implementations, the frequency-filter module 2008 is a two-dimensional spatial Fourier Transform, a high pass filter, a low pass filter, a bandpass filter or a weighted bandpass filter.

In some implementations, apparatus 2200 includes a spatial-cluster module 2012 that applies spatial clustering to the frequency filtered identified pixel values of skin 2010, generating spatial clustered frequency filtered identified pixel values of skin 2014. The spatial-cluster module 2012 performs block 2506 in FIG. 25. In some implementations, the spatial clustering includes fuzzy clustering, k-means clustering, expectation-maximization process, Ward's apparatus or seed point based clustering.

In some implementations, apparatus 2200 includes a frequency-filter module 2016 that applies a frequency filter to the spatial clustered frequency filtered identified pixel values of skin 2014, which generates frequency filtered spatial clustered frequency filtered identified pixel values of skin 2018. The frequency-filter module 2016 performs block 2508 in FIG. 25 to generate a temporal variation 2022. In some implementations, the frequency-filter module 2016 is a one-dimensional spatial Fourier Transform, a high pass filter, a low pass filter, a bandpass filter or a weighted bandpass filter. Some implementations of the frequency-filter module 2016 includes de-noising (e.g. smoothing of the data with a Gaussian filter). The skin-pixel-identification module 2002, the frequency-filter module 2008, the spatial-cluster module 2012 and the frequency-filter module 2016 amplify temporal variations in the two or more images 1604.

The frequency-filter module 2016 is operably coupled to one of more modules in FIG. 21 to generate and present any one or a number of biological vital signs from amplified motion in the temporal variation 2022.

Figure 23:
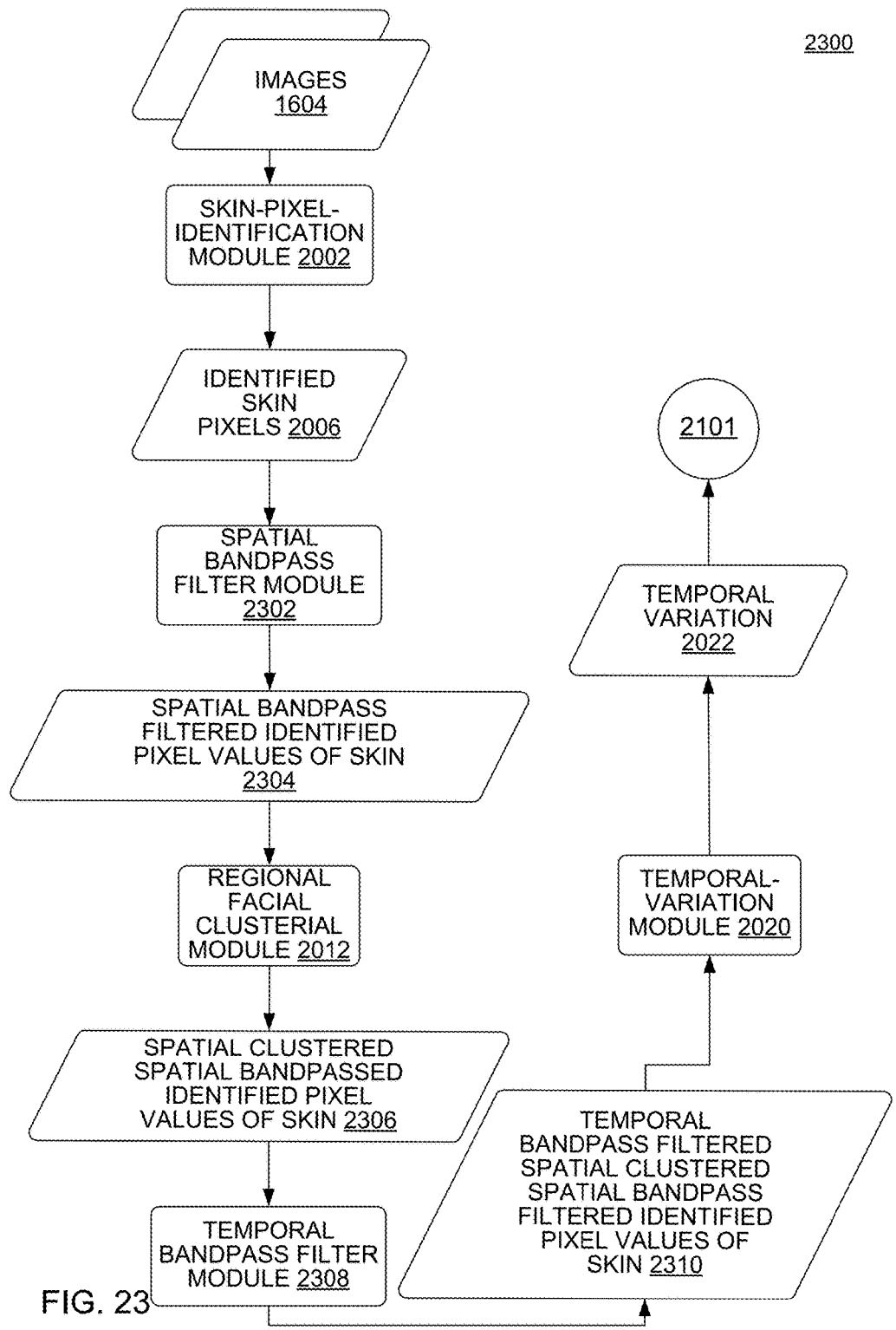
FIG. 23 is a block diagram of an apparatus of variation amplification, according to an implementation.

FIG. 23 is a block diagram of an apparatus 2300 of variation amplification, according to an implementation. Apparatus 2300 analyzes the temporal and spatial variations in digital images of an animal subject in order to generate and communicate biological vital signs.

In some implementations, apparatus 2300 includes a skin-pixel-identification module 2002 that identifies pixel values 2006 that are representative of the skin in two or more images 1604. The skin-pixel-identification module 2002 performs block 2502 in FIG. 27. Some implementations of the skin-pixel-identification module 2002 perform an automatic seed point based clustering process on the least two images 1604. In some implementations, apparatus 2300 includes a spatial bandpass filter module 2302 that applies a spatial bandpass filter to the identified pixel values 2006, generating spatial bandpassed filtered identified pixel values of skin 2304. In some implementations, the spatial bandpass filter module 2302 includes a two-dimensional spatial Fourier Transform, a high pass filter, a low pass filter, a bandpass filter or a weighted bandpass filter. The spatial bandpass filter module 2302 performs block 2702 in FIG. 27.

In some implementations, apparatus 2300 includes a spatial-cluster module 2012 that applies spatial clustering to the frequency filtered identified pixel values of skin 2010, generating spatial clustered spatial bandpassed identified pixel values of skin 2306. In some implementations, the spatial clustering includes fuzzy clustering, k-means clustering, expectation-maximization process, Ward's apparatus or seed point based clustering. The spatial-cluster module 2012 performs block 2704 in FIG. 27.

In some implementations, apparatus 2300 includes a temporal bandpass filter module 2308 that applies a temporal bandpass filter to the spatial clustered spatial bandpass filtered identified pixel values of skin 2306, generating temporal bandpass filtered spatial clustered spatial bandpass filtered identified pixel values of skin 2310. In some implementations, the temporal bandpass filter is a one-dimensional spatial Fourier Transform, a high pass filter, a low pass filter, a bandpass filter or a weighted bandpass filter. The temporal bandpass filter module 2308 performs block 2706 in FIG. 27.

In some implementations, apparatus 2300 includes a temporal-variation module 2020 that determines temporal variation 2422 of the temporal bandpass filtered spatial clustered spatial bandpass filtered identified pixel values of skin 2310. Thus, temporal variation 2422 represents temporal variation of the images 1604. The temporal-variation module 2420 performs block 2708 of FIG. 27. The temporal-variation module 2420 is operably coupled to one or more modules in FIG. 21 to generate and present any one of a number of biological vital signs from amplified motion in the temporal variation 2422.

Figure 24:
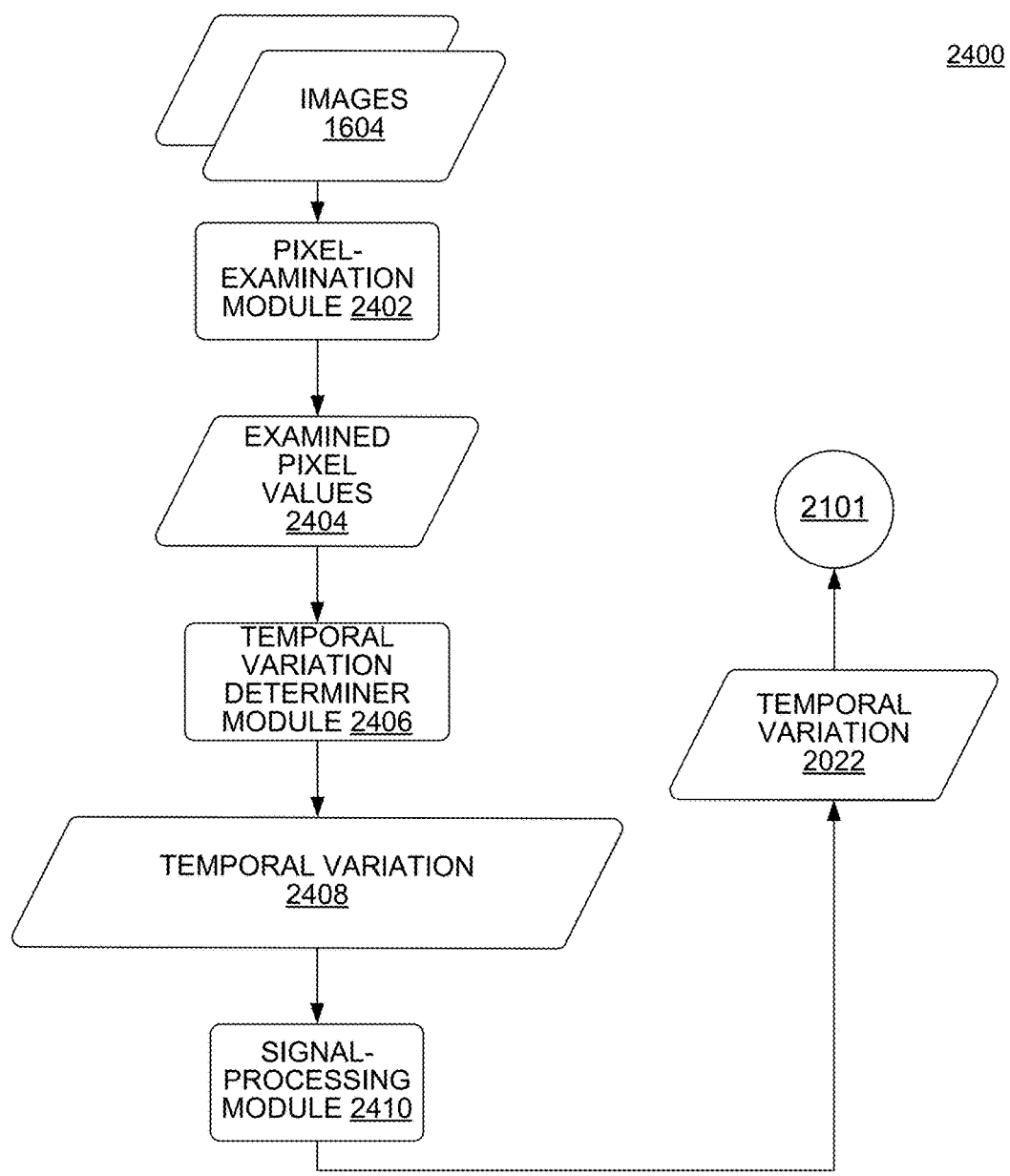
FIG. 24 is an apparatus that performs variation amplification to generate biological vital signs, according to an implementation.

FIG. 24 is a block diagram of an apparatus 2400 of variation amplification, according to an implementation.

In some implementations, apparatus 2400 includes a pixel-examination-module 2402 that examines pixel values of two or more images 1604, generating examined pixel values 2404. The pixel-examination-module 2402 performs block 2802 in FIG. 28.

In some implementations, apparatus 2400 includes a temporal variation determiner module 2406 that determines a temporal variation 2408 of the examined pixel values 2404. The temporal variation determiner module 2406 performs block 2804 in FIG. 28.

In some implementations, apparatus 2400 includes a signal-processing module 2410 that applies signal processing to the pixel value temporal variations 2408, generating an amplified temporal variation 2422. The signal-processing module 2410 performs block 2806 in FIG. 28. The signal processing amplifies the temporal variation 2408, even when the temporal variation 2408 is small. In some implementations, the signal processing performed by signal-processing module 2410 is temporal bandpass filtering that analyzes frequencies over time. In some implementations, the signal processing performed by signal-processing module 2410 is spatial processing that removes noise. Apparatus 2400 amplifies only small temporal variations in the signal-processing module.

While apparatus 2400 can process large temporal variations, an advantage in apparatus 2400 is provided for small temporal variations. Therefore apparatus 2400 is most effective when the two or more images 1604 have small temporal variations between the two or more images 1604. In some implementations, a vital sign is generated from the amplified temporal variations of the two or more images 1604 from the signal-processing module 2410.

Vital Sign Amplification Method Implementations

FIG. 25-29 each use spatial and temporal signal processing to generate vital signs from a series of digital images.

FIG. 25 is a flowchart of a method 2500 of variation amplification, according to an implementation. Method 2500 analyzes the temporal and spatial variations in digital images of an animal subject in order to generate and communicate biological vital signs.

In some implementations, method 2500 includes identifying pixel values of two or more images that are representative of the skin, at block 2502. Some implementations of identifying pixel values that are representative of the skin includes performing an automatic seed point based clustering process on the least two images.

In some implementations, method 2500 includes applying a frequency filter to the identified pixel values that are representative of the skin, at block 2504. In some implementations, the frequency filter in block 2504 is a two-dimensional spatial Fourier Transform, a high pass filter, a low pass filter, a bandpass filter or a weighted bandpass filter.

In some implementations, method 2500 includes applying spatial clustering to the frequency filtered identified pixel values of skin, at block 2506. In some implementations, the spatial clustering includes fuzzy clustering, k-means clustering, expectation-maximization process, Ward's method or seed point based clustering.

In some implementations, method 2500 includes applying a frequency filter to the spatial clustered frequency filtered identified pixel values of skin, at block 2508. In some implementations, the frequency filter in block 2508 is a one-dimensional spatial Fourier Transform, a high pass filter, a low pass filter, a bandpass filter or a weighted bandpass filter. Some implementations of applying a frequency filter at block 2508 include de-noising (e.g. smoothing of the data with a Gaussian filter).

Actions 2502, 2504, 2506 and 2508 amplify temporal variations in the two or more images.

In some implementations, method 2500 includes determining temporal variation of the frequency filtered spatial clustered frequency filtered identified pixel values of skin, at block 2510.

In some implementations, method 2500 includes analyzing the temporal variation to generate a pattern of flow of blood, at block 2512. In some implementations, the pattern flow of blood is generated from motion changes in the pixels and the temporal variation of color changes in the skin. In some implementations, method 2500 includes displaying the pattern of flow of blood for review by a healthcare worker, at block 2513.

In some implementations, method 2500 includes analyzing the temporal variation to generate heartrate, at block 2514. In some implementations, the heartrate is generated from the frequency spectrum of the temporal variation in a frequency range for heart beats, such as (0-10 Hertz). In some implementations, method 2500 includes displaying the heartrate for review by a healthcare worker, at block 2515.

In some implementations, method 2500 includes analyzing the temporal variation to determine respiratory rate, at block 2516. In some implementations, the respiratory rate is generated from the motion of the pixels in a frequency range for respiration (0-5 Hertz). In some implementations, method 2500 includes displaying the respiratory rate for review by a healthcare worker, at block 2517.

In some implementations, method 2500 includes analyzing the temporal variation to generate blood pressure, at block 2518. In some implementations, the blood pressure is generated by analyzing the motion of the pixels and the color changes based on the clustering process and potentially temporal data from the infrared sensor. In some implementations, method 2500 includes displaying the blood pressure for review by a healthcare worker, at block 2519.

In some implementations, method 2500 includes analyzing the temporal variation to generate EKG, at block 2520. In some implementations, method 2500 includes displaying the EKG for review by a healthcare worker, at block 2521.

In some implementations, method 2500 includes analyzing the temporal variation to generate pulse oximetry, at block 2522. In some implementations, the pulse oximetry is generated by analyzing the temporal color changes based in conjunction with the k-means clustering process and potentially temporal data from the infrared sensor. In some implementations, method 2500 includes displaying the pulse oximetry for review by a healthcare worker, at block 2523.

FIG. 26 is a flowchart of a method of variation amplification, according to an implementation that does not include a separate action of determining a temporal variation. Method 2600 analyzes the temporal and spatial variations in digital images of an animal subject in order to generate and communicate biological vital signs.

In some implementations, method 2600 includes identifying pixel values of two or more images that are representative of the skin, at block 2502. Some implementations of identifying pixel values that are representative of the skin includes performing an automatic seed point based clustering process on the least two images.

In some implementations, method 2600 includes applying a frequency filter to the identified pixel values that are representative of the skin, at block 2504. In some implementations, the frequency filter in block 2504 is a two-dimensional spatial Fourier Transform, a high pass filter, a low pass filter, a bandpass filter or a weighted bandpass filter.

In some implementations, method 2600 includes applying spatial clustering to the frequency filtered identified pixel values of skin, at block 2506. In some implementations, the spatial clustering includes fuzzy clustering, k-means clustering, expectation-maximization process, Ward's method or seed point based clustering.

In some implementations, method 2600 includes applying a frequency filter to the spatial clustered frequency filtered identified pixel values of skin, at block 2508, yielding a temporal variation. In some implementations, the frequency filter in block 2508 is a one-dimensional spatial Fourier Transform, a high pass filter, a low pass filter, a bandpass filter or a weighted bandpass filter.

In some implementations, method 2600 includes analyzing the temporal variation to generate a pattern of flow of blood, at block 2512. In some implementations, the pattern flow of blood is generated from motion changes in the pixels and the temporal variation of color changes in the skin. In some implementations, method 2600 includes displaying the pattern of flow of blood for review by a healthcare worker, at block 2513.

In some implementations, method 2600 includes analyzing the temporal variation to generate heartrate, at block 2514. In some implementations, the heartrate is generated from the frequency spectrum of the temporal variation in a frequency range for heart beats, such as (0-10 Hertz). In some implementations, method 2600 includes displaying the heartrate for review by a healthcare worker, at block 2515.

In some implementations, method 2600 includes analyzing the temporal variation to determine respiratory rate, at block 2516. In some implementations, the respiratory rate is generated from the motion of the pixels in a frequency range for respiration (0-5 Hertz). In some implementations, method 2600 includes displaying the respiratory rate for review by a healthcare worker, at block 2517.

In some implementations, method 2600 includes analyzing the temporal variation to generate blood pressure, at block 2518. In some implementations, the blood pressure is generated by analyzing the motion of the pixels and the color changes based on the clustering process and potentially temporal data from the infrared sensor. In some implementations, method 2600 includes displaying the blood pressure for review by a healthcare worker, at block 2519.

In some implementations, method 2600 includes analyzing the temporal variation to generate EKG, at block 2520. In some implementations, method 2600 includes displaying the EKG for review by a healthcare worker, at block 2521.

In some implementations, method 2600 includes analyzing the temporal variation to generate pulse oximetry, at block 2522. In some implementations, the pulse oximetry is generated by analyzing the temporal color changes based in conjunction with the k-means clustering process and potentially temporal data from the infrared sensor. In some implementations, method 2600 includes displaying the pulse oximetry for review by a healthcare worker, at block 2523.

FIG. 27 is a flowchart of a method 2700 of variation amplification from which to generate and communicate biological vital signs, according to an implementation. Method 2700 analyzes the temporal and spatial variations in digital images of an animal subject in order to generate and communicate the biological vital signs.

In some implementations, method 2700 includes identifying pixel values of two or more images that are representative of the skin, at block 2502. Some implementations of identifying pixel values that are representative of the skin includes performing an automatic seed point based clustering process on the least two images.

In some implementations, method 2700 includes applying a spatial bandpass filter to the identified pixel values, at block 2702. In some implementations, the spatial filter in block 2702 is a two-dimensional spatial Fourier Transform, a high pass filter, a low pass filter, a bandpass filter or a weighted bandpass filter.

In some implementations, method 2700 includes applying spatial clustering to the spatial bandpass filtered identified pixel values of skin, at block 2704. In some implementations, the spatial clustering includes fuzzy clustering, k-means clustering, expectation-maximization process, Ward's method or seed point based clustering.

In some implementations, method 2700 includes applying a temporal bandpass filter to the spatial clustered spatial bandpass filtered identified pixel values of skin, at block 2706. In some implementations, the temporal bandpass filter in block 2706 is a one-dimensional spatial Fourier Transform, a high pass filter, a low pass filter, a bandpass filter or a weighted bandpass filter.

In some implementations, method 2700 includes determining temporal variation of the temporal bandpass filtered spatial clustered spatial bandpass filtered identified pixel values of skin, at block 2708.

In some implementations, method 2700 includes analyzing the temporal variation to generate and visually display a pattern of flow of blood, at block 2512. In some implementations, the pattern flow of blood is generated from motion changes in the pixels and the temporal variation of color changes in the skin. In some implementations, method 2700 includes displaying the pattern of flow of blood for review by a healthcare worker, at block 2513.

In some implementations, method 2700 includes analyzing the temporal variation to generate heartrate, at block 2514. In some implementations, the heartrate is generated from the frequency spectrum of the temporal variation in a frequency range for heart beats, such as (0-10 Hertz). In some implementations, method 2700 includes displaying the heartrate for review by a healthcare worker, at block 2515.

In some implementations, method 2700 includes analyzing the temporal variation to determine respiratory rate, at block 2516. In some implementations, the respiratory rate is generated from the motion of the pixels in a frequency range for respiration (0-5 Hertz). In some implementations, method 2700 includes displaying the respiratory rate for review by a healthcare worker, at block 2517.

In some implementations, method 2700 includes analyzing the temporal variation to generate blood pressure, at block 2518. In some implementations, the blood pressure is generated by analyzing the motion of the pixels and the color changes based on the clustering process and potentially temporal data from the infrared sensor. In some implementations, method 2700 includes displaying the blood pressure for review by a healthcare worker, at block 2519.

In some implementations, method 2700 includes analyzing the temporal variation to generate EKG, at block 2520. In some implementations, method 2700 includes displaying the EKG for review by a healthcare worker, at block 2521.

In some implementations, method 2700 includes analyzing the temporal variation to generate pulse oximetry, at block 2522. In some implementations, the pulse oximetry is generated by analyzing the temporal color changes based in conjunction with the k-means clustering process and potentially temporal data from the infrared sensor. In some implementations, method 2700 includes displaying the pulse oximetry for review by a healthcare worker, at block 2523.

Figure 28:
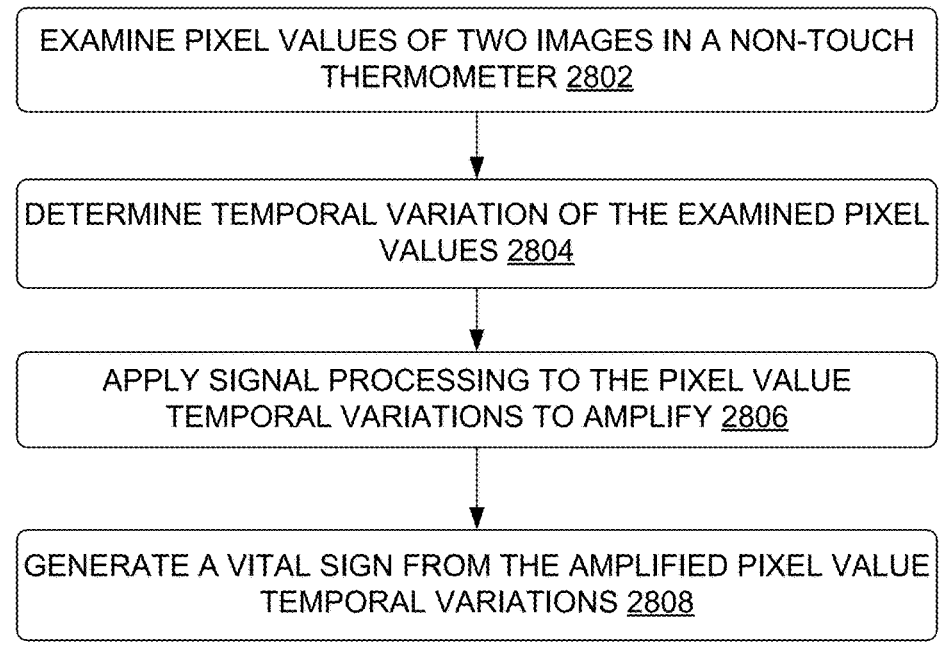
FIG. 28 is a flowchart of a method of variation amplification, according to an implementation.

FIG. 28 is a flowchart of a method 2800 of variation amplification, according to an implementation. Method 2800 displays the temporal variations based on temporal variations in videos that are difficult or impossible to see with the naked eye. Method 2800 applies spatial decomposition to a video, and applies temporal filtering to the frames. The resulting signal is then amplified to reveal hidden information. Method 2800 can visualize flow of blood filling a face in the video and also amplify and reveal small motions, and other vital signs such as blood pressure, respiration, EKG and pulse. Method 2800 can execute in real time to show phenomena occurring at temporal frequencies selected by the operator. A combination of spatial and temporal processing of videos can amplify subtle variations that reveal important aspects of the world. Method 2800 considers a time series of color values at any spatial location (e.g., a pixel) and amplifies variation in a given temporal frequency band of interest. For example, method 2800 selects and then amplifies a band of temporal frequencies including plausible human heart rates. The amplification reveals the variation of redness as blood flows through the face. Lower spatial frequencies are temporally filtered (spatial pooling) to allow a subtle input signal to rise above the solid-state image transducer 328 and quantization noise. The temporal filtering approach not only amplifies color variation, but can also reveal low-amplitude motion.

Method 2800 can enhance the subtle motions around the chest of a breathing baby. Method 2800 mathematical analysis employs a linear approximation related to the brightness constancy assumption used in optical flow formulations. Method 2800 also derives the conditions under which the linear approximation holds. The derivation leads to a multiscale approach to magnify motion without feature tracking or motion estimation. Properties of a voxel of fluid are observed, such as pressure and velocity, which evolve over time. Method 2800 studies and amplifies the variation of pixel values over time, in a spatially-multiscale manner. The spatially-multiscale manner to motion magnification does not explicitly estimate motion, but rather exaggerates motion by amplifying temporal color changes at fixed positions. Method 2800 employs differential approximations that form the basis of optical flow processes. Method 2800 described herein employs localized spatial pooling and bandpass filtering to extract and reveal visually the signal corresponding to the pulse. The domain analysis allows amplification and visualization of the pulse signal at each location on the face. Asymmetry in facial blood flow can be a symptom of arterial problems.

Method 2800 described herein makes imperceptible motions visible using a multiscale approach. Method 2800 amplifies small motions, in one embodiment. Nearly invisible changes in a dynamic environment can be revealed through spatio-temporal processing of standard monocular video sequences. Moreover, for a range of amplification values that is suitable for various applications, explicit motion estimation is not required to amplify motion in natural videos. Method 2800 is well suited to small displacements and lower spatial frequencies. Single framework can amplify both spatial motion and purely temporal changes (e.g., a heart pulse) and can be adjusted to amplify particular temporal frequencies. A spatial decomposition module decomposes the input video into different spatial frequency bands, then applies the same temporal filter to the spatial frequency bands. The outputted filtered spatial bands are then amplified by an amplification factor, added back to the original signal by adders, and collapsed by a reconstruction module to generate the output video. The temporal filter and amplification factors can be tuned to support different applications. For example, the system can reveal unseen motions of a solid-state image transducer 328, caused by the flipping mirror during a photo burst.

Method 2800 combines spatial and temporal processing to emphasize subtle temporal changes in a video. Method 2800 decomposes the video sequence into different spatial frequency bands. These bands might be magnified differently because (a) the bands might exhibit different signal-to-noise ratios or (b) the bands might contain spatial frequencies for which the linear approximation used in motion magnification does not hold. In the latter case, method 2800 reduces the amplification for these bands to suppress artifacts. When the goal of spatial processing is to increase temporal signal-to-noise ratio by pooling multiple pixels, the method spatially low-pass filters the frames of the video and downsamples the video frames for computational efficiency. In the general case, however, method 2800 computes a full Laplacian pyramid.

Method 2800 then performs temporal processing on each spatial band. Method 2800 considers the time series corresponding to the value of a pixel in a frequency band and applies a bandpass filter to extract the frequency bands of interest. As one example, method 2800 may select frequencies within the range of 0.4-4 Hz, corresponding to 24-240 beats per minute, if the operator wants to magnify a pulse. If method 2800 extracts the pulse rate, then method 2800 can employ a narrow frequency band around that value. The temporal processing is uniform for all spatial levels and for all pixels within each level. Method 2800 then multiplies the extracted bandpassed signal by a magnification factor .alpha. The magnification factor .alpha. can be specified by the operator, and can be attenuated automatically. Method 2800 adds the magnified signal to the original signal and collapses the spatial pyramid to obtain the final output. Since natural videos are spatially and temporally smooth, and since the filtering is performed uniformly over the pixels, the method implicitly maintains spatiotemporal coherency of the results. The motion magnification amplifies small motion without tracking motion. Temporal processing produces motion magnification, shown using an analysis that relies on the first-order Taylor series expansions common in optical flow analyses.

Method 2800 begins with a pixel-examination module in the microprocessor 302 of the non-touch biologic detectors 300, 400 or 300 examining pixel values of two or more images 1604 from the solid-state image transducer 328, at block 2802.

Method 2800 thereafter determines the temporal variation of the examined pixel values, at block 2804 by a temporal-variation module in the microprocessor 302.

A signal-processing module in the microprocessor 302 applies signal processing to the pixel value temporal variations, at block 2806. Signal processing amplifies the determined temporal variations, even when the temporal variations are small. Method 2800 amplifies only small temporal variations in the signal-processing module. While method 2800 can be applied to large temporal variations, an advantage in method 2800 is provided for small temporal variations. Therefore method 2800 is most effective when the input images 1604 have small temporal variations between the images 1604. In some implementations, the signal processing at block 2806 is temporal bandpass filtering that analyzes frequencies over time. In some implementations, the signal processing at block 2806 is spatial processing that removes noise.

In some implementations, a vital sign is generated from the amplified temporal variations of the input images 1604 from the signal processor at block 2808. Examples of generating a vital signal from a temporal variation include as in actions 2512, 2514, 2516, 2518, 2520 and 2522 in FIGS. 25, 26 and 27.

Figure 29:
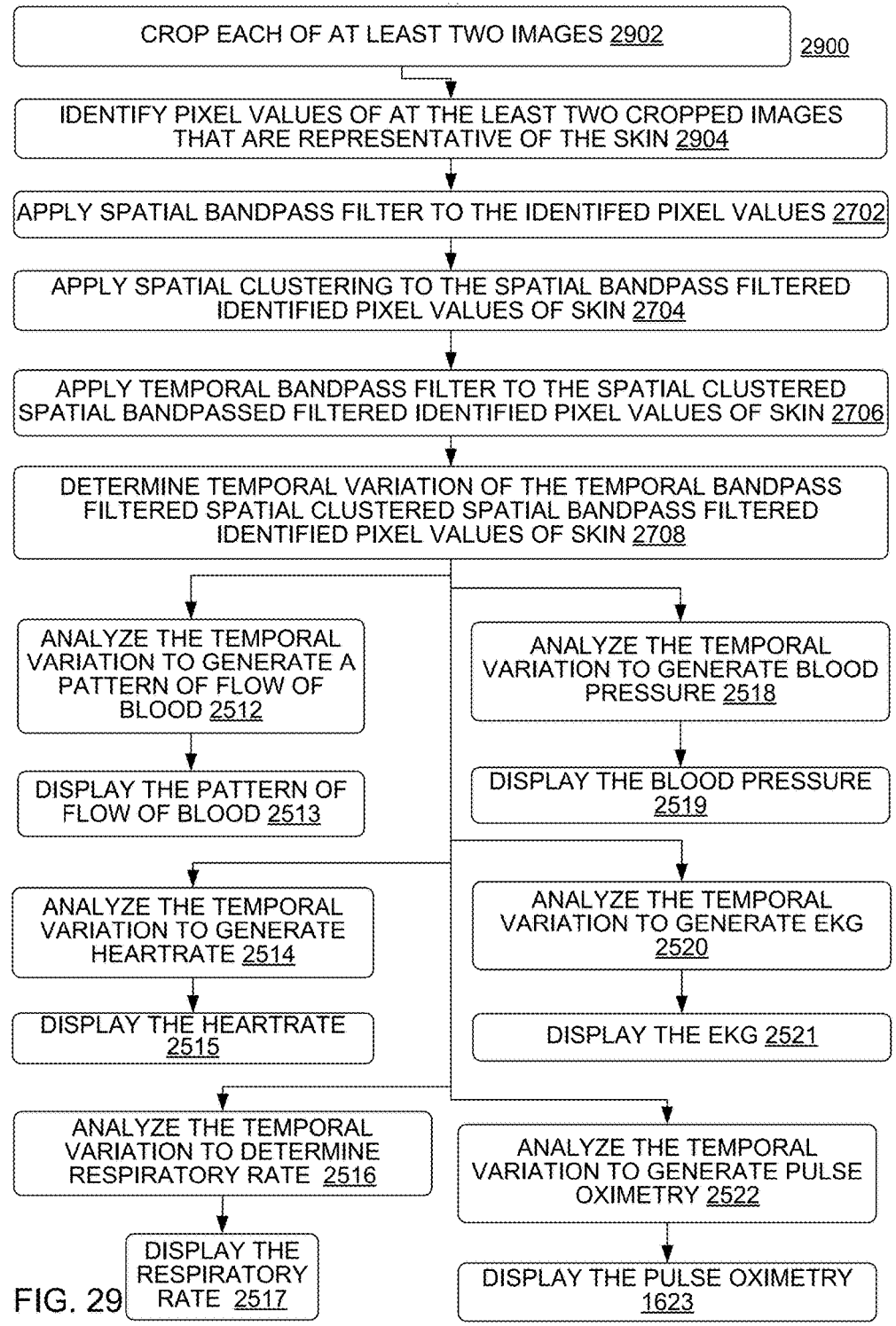
FIG. 29 is a flowchart of a method of variation amplification from which to generate and communicate biological vital signs, according to an implementation.

FIG. 29 is a flowchart of a method 2900 of variation amplification from which to generate and communicate biological vital signs, according to an implementation.

Method 2900 analyzes the temporal and spatial variations in digital images of an animal subject in order to generate and communicate the biological vital signs.

In some implementations, method 2900 includes cropping at least two images to exclude areas that do not include a skin region, at block 2902. For example, the excluded area can be a perimeter area around the center of each image, so that an outside border area of the image is excluded. In some implementations, of cropping out the border, about 72% of the width and about 72% of the height of each image is cropped out, leaving only 7.8% of the original uncropped image, which eliminates about 11/12 of each image and reduces the amount of processing time for the remainder of the actions in this process by about 12-fold. This one action alone at block 2902 in method 2900 can reduce the processing time of plurality of images 330 in comparison to method 2700 from 4 minutes to 30 seconds, which is of significant difference to the health workers who used devices that implement method 2900. In some implementations, the remaining area of the image after cropping in a square area and in other implementation the remaining area after cropping is a circular area. Depending upon the topography and shape of the area in the images that has the most pertinent portion of the imaged subject, different geometries and sizes are most beneficial. The action of cropping the images at block 2902 can be applied at the beginning of methods 2500, 2600, 2700 and 2800 in FIGS. 25, 26, 27 and 28, respectively. In other implementations of apparatus 1600, 1700, 1800, 1900, 2000, 2100, 2200, 2300 and 2400, a cropper module that performs block 2902 is placed at the beginning of the modules to greatly decrease processing time of the apparatus.

In some implementations, method 2900 includes identifying pixel values of the at least two or more cropped images that are representative of the skin, at block 2904. Some implementations of identifying pixel values that are representative of the skin include performing an automatic seed point based clustering process on the least two images.

In some implementations, method 2900 includes applying a spatial bandpass filter to the identified pixel values, at block 2702. In some implementations, the spatial filter in block 2702 is a two-dimensional spatial Fourier Transform, a high pass filter, a low pass filter, a bandpass filter or a weighted bandpass filter.

In some implementations, method 2900 includes applying spatial clustering to the spatial bandpass filtered identified pixel values of skin, at block 2704. In some implementations, the spatial clustering includes fuzzy clustering, k-means clustering, expectation-maximization process, Ward's method or seed point based clustering.

In some implementations, method 2900 includes applying a temporal bandpass filter to the spatial clustered spatial bandpass filtered identified pixel values of skin, at block 2706. In some implementations, the temporal bandpass filter in block 2706 is a one-dimensional spatial Fourier Transform, a high pass filter, a low pass filter, a bandpass filter or a weighted bandpass filter.

In some implementations, method 2900 includes determining temporal variation of the temporal bandpass filtered spatial clustered spatial bandpass filtered identified pixel values of skin, at block 2708.

In some implementations, method 2900 includes analyzing the temporal variation to generate and visually display a pattern of flow of blood, at block 2512. In some implementations, the pattern flow of blood is generated from motion changes in the pixels and the temporal variation of color changes in the skin. In some implementations, method 2900 includes displaying the pattern of flow of blood for review by a healthcare worker, at block 2513.

In some implementations, method 2900 includes analyzing the temporal variation to generate heartrate, at block 2514. In some implementations, the heartrate is generated from the frequency spectrum of the temporal variation in a frequency range for heart beats, such as (0-10 Hertz). In some implementations, method 2900 includes displaying the heartrate for review by a healthcare worker, at block 2515.

In some implementations, method 2900 includes analyzing the temporal variation to determine respiratory rate, at block 2516. In some implementations, the respiratory rate is generated from the motion of the pixels in a frequency range for respiration (0-5 Hertz). In some implementations, method 2900 includes displaying the respiratory rate for review by a healthcare worker, at block 2517.

In some implementations, method 2900 includes analyzing the temporal variation to generate blood pressure, at block 2518. In some implementations, the blood pressure is generated by analyzing the motion of the pixels and the color changes based on the clustering process and potentially temporal data from the infrared sensor. In some implementations, method 2900 includes displaying the blood pressure for review by a healthcare worker, at block 2519.

In some implementations, method 2900 includes analyzing the temporal variation to generate EKG, at block 2520. In some implementations, method 2900 includes displaying the EKG for review by a healthcare worker, at block 2521.

In some implementations, method 2900 includes analyzing the temporal variation to generate pulse oximetry, at block 2522. In some implementations, the pulse oximetry is generated by analyzing the temporal color changes based in conjunction with the k-means clustering process and potentially temporal data from the infrared sensor. In some implementations, method 2900 includes displaying the pulse oximetry for review by a healthcare worker, at block 2523.

Non-Touch Cubic Temperature Estimation Method Implementations

Figure 30:
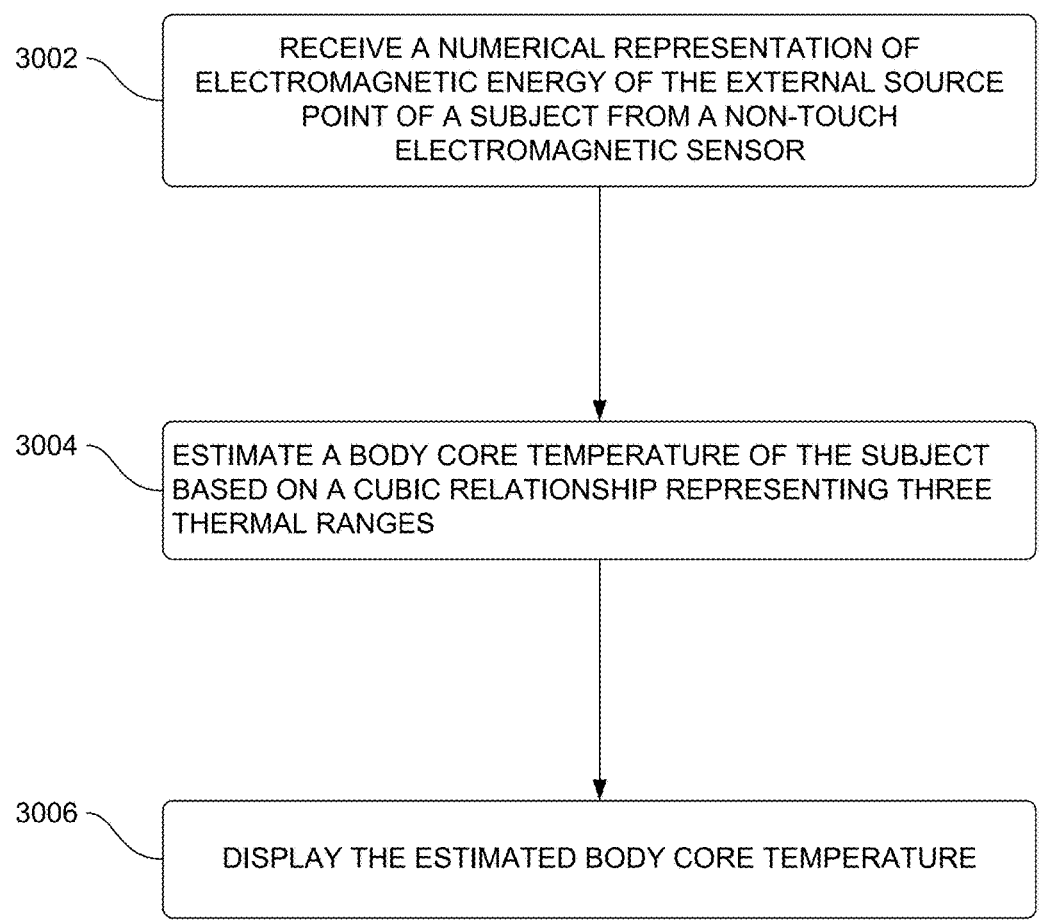
FIG. 30 is a flowchart of a method to estimate a body core temperature from an external source point in reference to a cubic relationship, according to an implementation.

FIG. 30 is a flowchart of a method 3000 to estimate a body core temperature from an external source point in reference to a cubic relationship, according to an implementation.

Method 3000 includes receiving from a non-touch electromagnetic sensor a numerical representation of electromagnetic energy of the external source point of a subject, at block 3002.

Method 3000 also includes estimating the body core temperature of the subject from the numerical representation of the electromagnetic energy of the external source point, a representation of an ambient air temperature reading, a representation of a calibration difference, and a representation of a bias in consideration of the temperature sensing mode, at block 3004. The estimating at block 3004 is based on a cubic relationship representing three thermal ranges between the body core temperature and the numerical representation of the electromagnetic energy of the external source point. The cubic relationship includes a coefficient representative of different relationships between the external source point and the body core temperature in the three thermal ranges.

A cubic relationship for all ranges of ambient temperatures provides best results because a linear or a quadratic relationship provide inaccurate estimates of body temperature, yet a quartic relationship, a quintic relationship, sextic relationship, a septic relationship or an octic relationship provide estimates along a highly irregular curve that is far too wavy or twisting with relatively sharp deviations from one ambient temperature to another ambient temperature.

Method 3000 also includes displaying the body core temperature, at block 3006.

Figure 31:
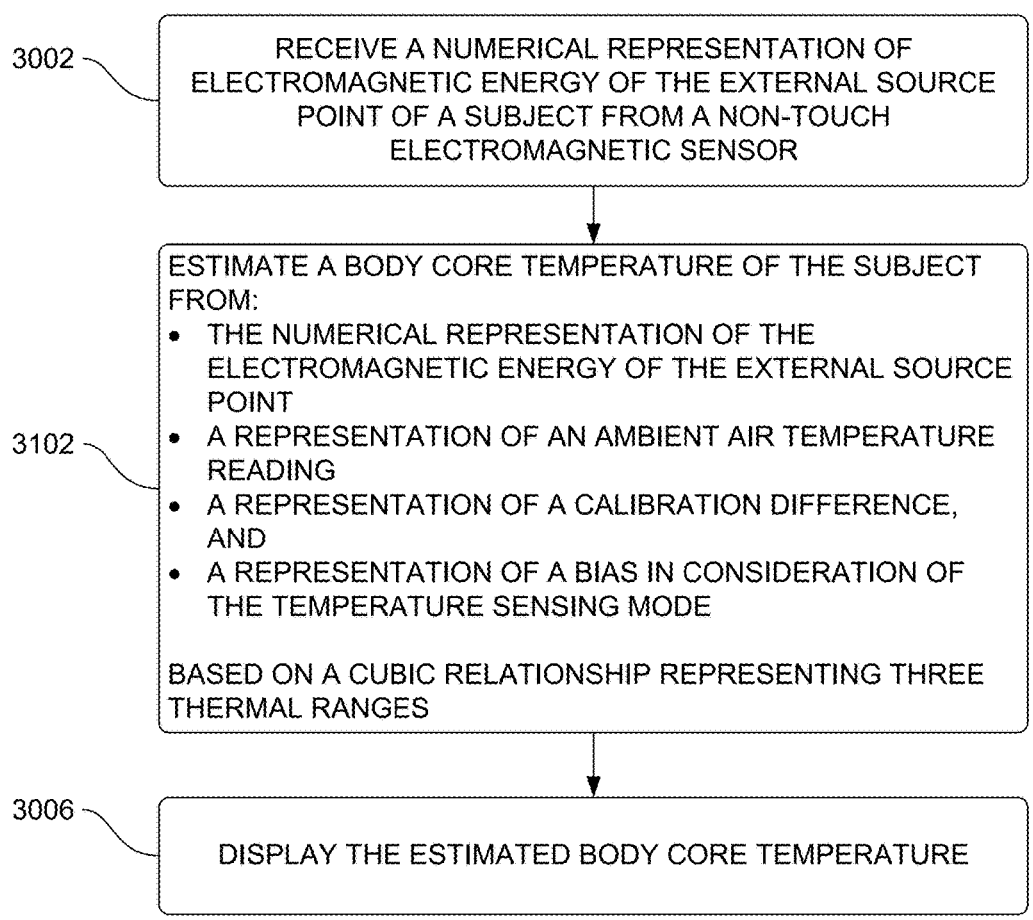
FIG. 31 is a flowchart of a method to estimate a body core temperature from an external source point and other measurements in reference to a cubic relationship, according to an implementation.

FIG. 31 is a flowchart of a method 3100 to estimate a body core temperature from an external source point and other measurements in reference to a cubic relationship, according to an implementation;

Method 3100 includes receiving from a non-touch electromagnetic sensor a numerical representation of electromagnetic energy of the external source point of a subject, at block 3002.

Method 3100 also includes estimating the body core temperature of the subject from the numerical representation of the electromagnetic energy of the external source point, a representation of an ambient air temperature reading, a representation of a calibration difference, and a representation of a bias in consideration of the temperature sensing mode, at block 3102. The estimating at block 3104 is based on a cubic relationship representing three thermal ranges between the body core temperature and the numerical representation of the electromagnetic energy of the external source point. The cubic relationship includes a coefficient representative of different relationships between the external source point and the body core temperature in the three thermal ranges, wherein the cubic relationship is:

$$T_B = AT_{Skin}^3 + BT_{Skin}^2 + CT_{Skin} + D - E(T_{Ambient} - 75),$$
$$T_{Ambient} < T_1 \text{ or } T_{Ambient} > T_2 \text{ and } T_B = AT_{Skin}^3 + BT_{Skin}^2 + CT_{Skin} + D, T_1 < T_{Ambient} < T_2$$

where:
$T_B$ is the body core temperature
$T_{skin}$ is the numerical representation of the electromagnetic energy of the external source point
A is 0.0002299688
B is −0.0464237524
C is 3.05944877
D is 31.36205
E is 0.135
$T_{ambient}$ is the ambient air temperature
$T_1$ and $T_2$ are boundaries between the three thermal ranges
$T_1$ and $T_2$ are selected from a group of pairs of ambient temperatures consisting of 67° F. and 82° F.; 87° F. and 95° F.; and 86° F. and 101° F.

Method 3100 also includes displaying the body core temperature, at block 3006.

In some implementations, methods 2500-3100 are implemented as a sequence of instructions which, when executed by a microprocessor 302 in FIG. 3-12, microprocessor 3504 In FIG. 35, main processor 3202 in FIG. 32 or processing unit 3304 in FIG. 33, cause the processor to perform the respective method. In other implementations, methods 2500-3100 are implemented as a computer-accessible medium having computer executable instructions capable of directing a microprocessor, such as microprocessor 302 in FIG. 3-12, microprocessor 3504 in FIG. 35, main processor 3202 in FIG. 32 or processing unit 3304 in FIG. 33, to perform the respective method. In different implementations, the medium is a magnetic medium, an electronic medium, or an optical medium.

Hardware and Operating Environments

FIG. 32 is a block diagram of a hand-held device 3200, according to an implementation. The hand-held device 3200 may also have the capability to allow voice communication.

Depending on the functionality provided by the hand-held device 3200, the hand-held device 3200 may be referred to as a data messaging device, a two-way pager, a cellular telephone with data messaging capabilities, a wireless Internet appliance, or a data communication device (with or without telephony capabilities).

The hand-held device 3200 includes a number of modules such as a main processor 3202 that controls the overall operation of the hand-held device 3200. Communication functions, including data and voice communications, are performed through a communication subsystem 3204. The communication subsystem 3204 receives messages from and sends messages to wireless networks 3205. In other implementations of the hand-held device 3200, the communication subsystem 3204 can be configured in accordance with the Global System for Mobile Communication (GSM), General Packet Radio Services (GPRS), Enhanced Data GSM Environment (EDGE), Universal Mobile Telecommunications Service (UMTS), data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), and future third-generation (3G) networks like EDGE and UMTS. Some other examples of data-centric networks include Mobitex™ and DataTAC™ network communication systems. Examples of other voice-centric data networks include Personal Communication Systems (PCS) networks like GSM and Time Division Multiple Access (TDMA) systems.

The wireless link connecting the communication subsystem 3204 with the wireless network 3205 represents one or more different Radio Frequency (RF) channels. With newer network protocols, these channels are capable of supporting both circuit switched voice communications and packet switched data communications.

The main processor 3202 also interacts with additional subsystems such as a Random Access Memory (RAM) 3206, a flash memory 3208, a display 3210, an auxiliary input/output (I/O) subsystem 3212, a data port 3214, a keyboard 3216, a speaker 3218, a microphone 3220, short-range communications subsystem 3222 and other device subsystems 3224. In some implementations, the flash memory 3208 includes a hybrid femtocell/Wi-Fi protocol stack 3209. The stack 3209 supports authentication and authorization between the hand-held device 3200 into a shared Wi-Fi network and both a 3G and 4G mobile networks.

Some of the subsystems of the hand-held device 3200 perform communication-related functions, whereas other subsystems may provide "resident" or on-device functions. By way of example, the display 3210 and the keyboard 3216 may be used for both communication-related functions, such as entering a text message for transmission over the wireless network 3205, and device-resident functions such as a calculator or task list.

The hand-held device 3200 can transmit and receive communication signals over the wireless network 3205 after required network registration or activation procedures have been completed. Network access is associated with a subscriber or user of the hand-held device 3200. To identify a subscriber, the hand-held device 3200 requires a SIM/RUIM card 3226 (i.e. Subscriber Identity Module or a Removable User Identity Module) to be inserted into a SIM/RUIM interface 3228 in order to communicate with a network. The SIM card or RUIM 3226 is one type of a conventional "smart card" that can be used to identify a subscriber of the hand-held device 3200 and to personalize the hand-held device 3200, among other things. Without the SIM card 3226, the hand-held device 3200 is not fully operational for communication with the wireless network 3205. By inserting the SIM card/RUIM 3226 into the SIM/RUIM interface 3228, a subscriber can access all subscribed services. Services may include: web browsing and messaging such as e-mail, voice mail, Short Message Service (SMS), and Multimedia Messaging Services (MMS). More advanced services may include: point of sale, field service and sales force automation. The SIM card/RUIM 3226 includes a processor and memory for storing information. Once the SIM card/RUIM 3226 is inserted into the SIM/RUIM interface 3228, the SIM is coupled to the main processor 3202. In order to identify the subscriber, the SIM card/RUIM 3226 can include some user parameters such as an International Mobile Subscriber Identity (IMSI). An advantage of using the SIM card/RUIM 3226 is that a subscriber is not necessarily bound by any single physical mobile device. The SIM card/RUIM 3226 may store additional subscriber information for the hand-held device 3200 as well, including datebook (or calendar) information and recent call information. Alternatively, user identification information can also be programmed into the flash memory 3208.

The hand-held device 3200 is a battery-powered device and includes a battery interface 3232 for receiving one or more rechargeable batteries 3230. In one or more implementations, the battery 3230 can be a smart battery with an embedded microprocessor. The battery interface 3232 is coupled to a regulator 3233, which assists the battery 3230 in providing power V+ to the hand-held device 3200. Although current technology makes use of a battery, future technologies such as micro fuel cells may provide the power to the hand-held device 3200.

The hand-held device 3200 also includes an operating system 3234 and modules 3236 to 3249 which are described in more detail below. The operating system 3234 and the modules 3236 to 3249 that are executed by the main processor 3202 are typically stored in a persistent nonvolatile medium such as the flash memory 3208, which may alternatively be a read-only memory (ROM) or similar storage element (not shown). Those skilled in the art will appreciate that portions of the operating system 3234 and the modules 3236 to 3249, such as specific device applications, or parts thereof, may be temporarily loaded into a volatile store such as the RAM 3206. Other modules can also be included.

The subset of modules 3236 that control basic device operations, including data and voice communication applications, will normally be installed on the hand-held device 3200 during its manufacture. Other modules include a message application 3238 that can be any suitable module that allows a user of the hand-held device 3200 to transmit and receive electronic messages. Various alternatives exist for the message application 3238 as is well known to those skilled in the art. Messages that have been sent or received by the user are typically stored in the flash memory 3208 of the hand-held device 3200 or some other suitable storage element in the hand-held device 3200. In one or more implementations, some of the sent and received messages may be stored remotely from the hand-held device 3200 such as in a data store of an associated host system with which the hand-held device 3200 communicates.

The modules can further include a device state module 3240, a Personal Information Manager (PIM) 3242, and other suitable modules (not shown). The device state module 3240 provides persistence, i.e. the device state module 3240 ensures that important device data is stored in persistent memory, such as the flash memory 3208, so that the data is not lost when the hand-held device 3200 is turned off or loses power.

The PIM 3242 includes functionality for organizing and managing data items of interest to the user, such as, but not limited to, e-mail, contacts, calendar events, voice mails, appointments, and task items. A PIM application has the ability to transmit and receive data items via the wireless network 3205. PIM data items may be seamlessly integrated, synchronized, and updated via the wireless network 3205 with the hand-held device 3200 subscriber's corresponding data items stored and/or associated with a host computer system. This functionality creates a mirrored host computer on the hand-held device 3200 with respect to such items. This can be particularly advantageous when the host computer system is the hand-held device 3200 subscriber's office computer system.

The hand-held device 3200 also includes a connect module 3244, and an IT policy module 3246. The connect module 3244 implements the communication protocols that are required for the hand-held device 3200 to communicate with the wireless infrastructure and any host system, such as an enterprise system, with which the hand-held device 3200 is authorized to interface. Examples of a wireless infrastructure and an enterprise system are given in FIGS. 32 and 33, which are described in more detail below.

The connect module 3244 includes a set of APIs that can be integrated with the hand-held device 3200 to allow the hand-held device 3200 to use any number of services associated with the enterprise system. The connect module 3244 allows the hand-held device 3200 to establish an end-to-end secure, authenticated communication pipe with the host system. A subset of applications for which access is provided by the connect module 3244 can be used to pass IT policy commands from the host system to the hand-held device 3200. This can be done in a wireless or wired manner. These instructions can then be passed to the IT policy module 3246 to modify the configuration of the hand-held device 3200. Alternatively, in some cases, the IT policy update can also be done over a wired connection.

The IT policy module 3246 receives IT policy data that encodes the IT policy. The IT policy module 3246 then ensures that the IT policy data is authenticated by the hand-held device 3200. The IT policy data can then be stored in the flash memory 3206 in its native form. After the IT policy data is stored, a global notification can be sent by the IT policy module 3246 to all of the applications residing on the hand-held device 3200. Applications for which the IT policy may be applicable then respond by reading the IT policy data to look for IT policy rules that are applicable.

The IT policy module 3246 can include a parser 3247, which can be used by the applications to read the IT policy rules. In some cases, another module or application can provide the parser. Grouped IT policy rules, described in more detail below, are retrieved as byte streams, which are then sent (recursively) into the parser to determine the values of each IT policy rule defined within the grouped IT policy rule. In one or more implementations, the IT policy module 3246 can determine which applications are affected by the IT policy data and transmit a notification to only those applications. In either of these cases, for applications that are not being executed by the main processor 3202 at the time of the notification, the applications can call the parser or the IT policy module 3246 when the applications are executed to determine if there are any relevant IT policy rules in the newly received IT policy data.

All applications that support rules in the IT Policy are coded to know the type of data to expect. For example, the value that is set for the "WEP User Name" IT policy rule is known to be a string; therefore the value in the IT policy data that corresponds to this rule is interpreted as a string. As another example, the setting for the "Set Maximum Password Attempts" IT policy rule is known to be an integer, and therefore the value in the IT policy data that corresponds to this rule is interpreted as such.

After the IT policy rules have been applied to the applicable applications or configuration files, the IT policy module 3246 sends an acknowledgement back to the host system to indicate that the IT policy data was received and successfully applied.

The programs 3237 can also include a temporal-variation-amplifier 3248 and a vital sign generator 3249. In some implementations, the temporal-variation-amplifier 3248 includes a skin-pixel-identifier 1602, a frequency-filter 1606, a regional facial clusterial module 1608 and a frequency filter 1610 as in FIGS. 16 and 17. In some implementations, the temporal-variation-amplifier 3248 includes a skin-pixel-identifier 1602, a spatial bandpass-filter 1802, regional facial clusterial module 1608 and a temporal bandpass filter 1804 as in FIG. 18. In some implementations, the temporal-variation-amplifier 3248 includes a pixel-examiner 1902, a temporal variation determiner 1906 and signal processor 1908 as in FIG. 19. In some implementations, the temporal-variation-amplifier 3248 includes a skin-pixel-identification module 2002, a frequency-filter module 2008, spatial-cluster module 2012 and a frequency filter module 2016 as in FIGS. 20 and 21. In some implementations, the temporal-variation-amplifier module 2002, a spatial bandpass filter module 2302, a spatial-cluster module 2012 and a temporal bandpass filter module 2306 as in FIG. 23. In some implementations, the temporal-variation-amplifier 3248 includes a pixel-examination-module 2402, a temporal variation determiner module 2406 and a signal processing module 2410 as in FIG. 24. The solid-state image transducer 328 captures images 330 and the vital sign generator 3249 generates the vital sign(s) 1616 that is displayed by display 3210 or transmitted by communication subsystem 3204 or short-range communications subsystem 3222, enunciated by speaker 3218 or stored by flash memory 3208.

Other types of modules can also be installed on the hand-held device 3200. These modules can be third party modules, which are added after the manufacture of the hand-held device 3200. Examples of third party applications include games, calculators, utilities, etc.

The additional applications can be loaded onto the hand-held device 3200 through at least one of the wireless network 3205, the auxiliary I/O subsystem 3212, the data port 3214, the short-range communications subsystem 3222, or any other suitable device subsystem 3224. This flexibility in application installation increases the functionality of the hand-held device 3200 and may provide enhanced on-device functions, communication-related functions, or both. For example, secure communication applications may enable electronic commerce functions and other such financial transactions to be performed using the hand-held device 3200.

The data port 3214 enables a subscriber to set preferences through an external device or module and extends the capabilities of the hand-held device 3200 by providing for information or module downloads to the hand-held device 3200 other than through a wireless communication network.

The alternate download path may, for example, be used to load an encryption key onto the hand-held device 3200 through a direct and thus reliable and trusted connection to provide secure device communication.

The data port 3214 can be any suitable port that enables data communication between the hand-held device 3200 and another computing device. The data port 3214 can be a serial or a parallel port. In some instances, the data port 3214 can be a USB port that includes data lines for data transfer and a supply line that can provide a charging current to charge the battery 3230 of the hand-held device 3200.

The short-range communications subsystem 3222 provides for communication between the hand-held device 3200 and different systems or devices, without the use of the wireless network 3205. For example, the subsystem 3222 may include an infrared device and associated circuits and modules for short-range communication. Examples of short-range communication standards include standards developed by the Infrared Data Association (IrDA), Bluetooth, and the 802.11 family of standards developed by IEEE.

Bluetooth is a wireless technology standard for exchanging data over short distances (using short-wavelength radio transmissions in the ISM band from 2400-2480 MHz) from fixed and mobile devices, creating personal area networks (PANs) with high levels of security. Created by telecom vendor Ericsson in 1994, Bluetooth was originally conceived as a wireless alternative to RS-232 data cables. Bluetooth can connect several devices, overcoming problems of synchronization. Bluetooth operates in the range of 2400-2483.5 MHz (including guard bands), which is in the globally unlicensed Industrial, Scientific and Medical (ISM) 2.4 GHz short-range radio frequency band. Bluetooth uses a radio technology called frequency-hopping spread spectrum. The transmitted data is divided into packets and each packet is transmitted on one of the 79 designated Bluetooth channels. Each channel has a bandwidth of 1 MHz. The first channel starts at 2402 MHz and continues up to 2480 MHz in 1 MHz steps. The first channel usually performs 1600 hops per second, with Adaptive Frequency-Hopping (AFH) enabled. Originally Gaussian frequency-shift keying (GFSK) modulation was the only modulation scheme available; subsequently, since the introduction of Bluetooth 2.0+EDR, π/4-DQPSK and 8DPSK modulation may also be used between compatible devices. Devices functioning with GFSK are said to be operating in basic rate (BR) mode where an instantaneous data rate of 1 Mbit/s is possible. The term Enhanced Data Rate (EDR) is used to describe π/4-DPSK and 8DPSK schemes, each giving 2 and 3 Mbit/s respectively. The combination of these (BR and EDR) modes in Bluetooth radio technology is classified as a "BR/EDR radio". Bluetooth is a packet-based protocol with a master-slave structure. One master may communicate with up to 7 slaves in a piconet; all devices share the master's clock. Packet exchange is based on the basic clock, defined by the master, which ticks at 312.5 μs intervals. Two clock ticks make up a slot of 625 μs; two slots make up a slot pair of 1250 μs. In the simple case of single-slot packets the master transmits in even slots and receives in odd slots; the slave, conversely, receives in even slots and transmits in odd slots. Packets may be 1, 3 or 5 slots long but in all cases the master transmit will begin in even slots and the slave transmit in odd slots. A master Bluetooth device can communicate with a maximum of seven devices in a piconet (an ad-hoc computer network using Bluetooth technology), though not all devices reach this maximum. The devices can switch roles, by agreement, and the slave can become the master (for example, a headset initiating a connection to a phone will necessarily begin as master, as initiator of the connection; but may subsequently prefer to be slave). The Bluetooth Core Specification provides for the connection of two or more piconets to form a scatternet, in which certain devices simultaneously play the master role in one piconet and the slave role in another. At any given time, data can be transferred between the master and one other device (except for the little-used broadcast mode. The master chooses which slave device to address; typically, the master switches rapidly from one device to another in a round-robin fashion. Since the master chooses which slave to address, whereas a slave is (in theory) supposed to listen in each receive slot, being a master is a lighter burden than being a slave. Being a master of seven slaves is possible; being a slave of more than one master is difficult. Many of the services offered over Bluetooth can expose private data or allow the connecting party to control the Bluetooth device. For security reasons it is necessary to be able to recognize specific devices and thus enable control over which devices are allowed to connect to a given Bluetooth device. At the same time, it is useful for Bluetooth devices to be able to establish a connection without user intervention (for example, as soon as the Bluetooth devices of each other are in range). To resolve this conflict, Bluetooth uses a process called bonding, and a bond is created through a process called pairing. The pairing process is triggered either by a specific request from a user to create a bond (for example, the user explicitly requests to "Add a Bluetooth device"), or the pairing process is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices. Once pairing successfully completes, a bond will have been formed between the two devices, enabling those two devices to connect to each other in the future without requiring the pairing process in order to confirm the identity of the devices. When desired, the bonding relationship can later be removed by the user. Secure Simple Pairing (SSP): This is required by Bluetooth v2.1, although a Bluetooth v2.1 device may only use legacy pairing to interoperate with a v2.0 or earlier device. Secure Simple Pairing uses a form of public key cryptography, and some types can help protect against man in the middle, or MITM attacks. SSP has the following characteristics: Just works: As implied by the name, this method just works. No user interaction is required; however, a device may prompt the user to confirm the pairing process. This method is typically used by headsets with very limited IO capabilities, and is more secure than the fixed PIN mechanism which is typically used for legacy pairing by this set of limited devices. This method provides no man in the middle (MITM) protection. Numeric comparison: If both devices have a display and at least one can accept a binary Yes/No user input, both devices may use Numeric Comparison. This method displays a 6-digit numeric code on each device. The user should compare the numbers to ensure that the numbers are identical. If the comparison succeeds, the user(s) should confirm pairing on the device(s) that can accept an input. This method provides MITM protection, assuming the user confirms on both devices and actually performs the comparison properly. Passkey Entry: This method may be used between a device with a display and a device with numeric keypad entry (such as a keyboard), or two devices with numeric keypad entry. In the first case, the display is used to show a 6-digit numeric code to the user, who then enters the code on the keypad. In the second case, the user of each device enters the same 6-digit number. Both of these cases provide MITM protection. Out of band (OOB): This method uses an external means of communication, such as Near Field Communication (NFC) to exchange some information used in the pairing process. Pairing is completed using the Bluetooth radio, but requires information from the OOB mechanism. This provides only the level of MITM protection that is present in the OOB mechanism. SSP is considered simple for the following reasons: In most cases, SSP does not require a user to generate a passkey. For use-cases not requiring MITM protection, user interaction can be eliminated. For numeric comparison, MITM protection can be achieved with a simple equality comparison by the user. Using OOB with NFC enables pairing when devices simply get close, rather than requiring a lengthy discovery process.

In use, a received signal such as a text message, an e-mail message, or web page download will be processed by the communication subsystem 3204 and input to the main processor 3202. The main processor 3202 will then process the received signal for output to the display 3210 or alternatively to the auxiliary I/O subsystem 3212. A subscriber may also compose data items, such as e-mail messages, for example, using the keyboard 3216 in conjunction with the display 3210 and possibly the auxiliary I/O subsystem 3212. The auxiliary subsystem 3212 may include devices such as: a touch screen, mouse, track ball, infrared fingerprint detector, or a roller wheel with dynamic button pressing capability. The keyboard 3216 is preferably an alphanumeric keyboard and/or telephone-type keypad. However, other types of keyboards may also be used. A composed item may be transmitted over the wireless network 3205 through the communication subsystem 3204.

For voice communications, the overall operation of the hand-held device 3200 is substantially similar, except that the received signals are output to the speaker 3218, and signals for transmission are generated by the microphone 3220. Alternative voice or audio I/O subsystems, such as a voice message recording subsystem, can also be implemented on the hand-held device 3200. Although voice or audio signal output is accomplished primarily through the speaker 3218, the display 3210 can also be used to provide additional information such as the identity of a calling party, duration of a voice call, or other voice call related information.

FIG. 33 is a block diagram of a hardware and operating environment 3300 in which different implementations can be practiced. The description of FIG. 33 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

FIG. 33 illustrates an example of a computer environment 3300 useful in the context of the environment of FIG. 3-18, in accordance with an implementation. The computer environment 3300 includes a computation resource 3302 capable of implementing the processes described herein. It will be appreciated that other devices can alternatively used that include more modules, or fewer modules, than those illustrated in FIG. 33.

The illustrated operating environment 3300 is only one example of a suitable operating environment, and the example described with reference to FIG. 33 is not intended to suggest any limitation as to the scope of use or functionality of the implementations of this disclosure. Other well-known computing systems, environments, and/or configurations can be suitable for implementation and/or application of the subject matter disclosed herein.

The computation resource 3302 includes one or more processors or processing units 3304, a system memory 3306, and a bus 3308 that couples various system modules including the system memory 3306 to processing unit 3304 and other elements in the environment 3300. The bus 3308 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 3306 includes nonvolatile read-only memory (ROM) 3310 and random access memory (RAM) 3312, which can or can not include volatile memory elements. A basic input/output system (BIOS) 3314, containing the elementary routines that help to transfer information between elements within computation resource 3302 and with external items, typically invoked into operating memory during start-up, is stored in ROM 3310.

The computation resource 3302 further can include a non-volatile read/write memory 3316, represented in FIG. 33 as a hard disk drive, coupled to bus 3308 via a data media interface 3317 (e.g., a SCSI, ATA, or other type of interface); a magnetic disk drive (not shown) for reading from, and/or writing to, a removable magnetic disk 3320 and an optical disk drive (not shown) for reading from, and/or writing to, a removable optical disk 3326 such as a CD, DVD, or other optical media.

The non-volatile read/write memory 3316 and associated computer-readable media provide nonvolatile storage of computer-readable instructions, data structures, program modules and other data for the computation resource 3302. Although the exemplary environment 3300 is described herein as employing a non-volatile read/write memory 3316, a removable magnetic disk 3320 and a removable optical disk 3326, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 3316, magnetic disk 3320, optical disk 3326, ROM 3310, or RAM 3312, including an operating system 3330, one or more application programs 3332, program modules 3334 and program data 3336. Examples of computer operating systems conventionally employed include the NUCLEUS® operating system, the LINUX® operating system, and others, for example, providing capability for supporting application programs 3332 using, for example, code modules written in the C++® computer programming language. The application programs 3332 and/or the program modules 3334 can also include a temporal-variation-amplifier (as shown in 3248 in FIG. 32) and a vital sign generator (as shown in 3249 in FIG. 33). In some implementations, the temporal-variation-amplifier 3248 in the application programs 3332 and/or the program modules 3334 includes a skin-pixel-identifier 1602, a frequency-filter 1606, regional facial clusterial module 1608 and a frequency filter 1610 as in FIGS. 16 and 17. In some implementations, the temporal-variation-amplifier 3248 in application programs 3332 and/or the program modules 3334 includes a skin-pixel-identifier 1602, a spatial bandpass-filter 1802, regional facial clusterial module 1608 and a temporal bandpass filter 1804 as in FIG. 18. In some implementations, the temporal-variation-amplifier 3248 in the application programs 3332 and/or the program modules 3334 includes a pixel-examiner 1902, a temporal variation determiner 1906 and signal processor 1908 as in FIG. 19. In some implementations, the temporal-variation-amplifier 3248 in the application programs 3332 and/or the program modules 3334 includes a skin-pixel-identification module 2002, a frequency-filter module 2008, spatial-cluster module 2012 and a frequency filter module 2016 as in FIGS. 20 and 21. In some implementations, the temporal-variation-amplifier 3248 in the application programs 3332 and/or the program modules 3334 includes a skin-pixel-identification module 2002, a spatial bandpass filter module 2302, a spatial-cluster module 2012 and a temporal bandpass filter module 2306 as in FIG. 23. In some implementations, the temporal-variation-amplifier 3248 in the application programs 3332 and/or the program modules 3334 includes a pixel-examination-module 2402, a temporal variation determiner module 2406 and a signal processing module 2410 as in FIG. 24. The solid-state image transducer 328 captures images 330 that are processed by the temporal-variation-amplifier 3248 and the vital sign generator 3249 to generate the vital sign(s) 1616 that is displayed by display 3350 or transmitted by computation resource 3302, enunciated by a speaker or stored in program data 3336.

A user can enter commands and information into computation resource 3302 through input devices such as input media 3338 (e.g., keyboard/keypad, tactile input or pointing device, mouse, foot-operated switching apparatus, joystick, touchscreen or touchpad, microphone, antenna etc.). Such input devices 3338 are coupled to the processing unit 3304 through a conventional input/output interface 3342 that is, in turn, coupled to the system bus. Display 3350 or other type of display device is also coupled to the system bus 3308 via an interface, such as a video adapter 3352.

The computation resource 3302 can include capability for operating in a networked environment using logical connections to one or more remote computers, such as a remote computer 3360. The remote computer 3360 can be a personal computer, a server, a router, a network PC, a peer device or other common network node, and typically includes many or all of the elements described above relative to the computation resource 3302. In a networked environment, program modules depicted relative to the computation resource 3302, or portions thereof, can be stored in a remote memory storage device such as can be associated with the remote computer 3360. By way of example, remote application programs 3362 reside on a memory device of the remote computer 3360. The logical connections represented in FIG. 33 can include interface capabilities, e.g., such as interface capabilities in FIG. 14, a storage area network (SAN, not illustrated in FIG. 33), local area network (LAN) 3372 and/or a wide area network (WAN) 3374, but can also include other networks.

Such networking environments are commonplace in modern computer systems, and in association with intranets and the Internet. In certain implementations, the computation resource 3302 executes an Internet Web browser program (which can optionally be integrated into the operating system 3330), such as the "Internet Explorer®" Web browser manufactured and distributed by the Microsoft Corporation of Redmond, Wash.

When used in a LAN-coupled environment, the computation resource 3302 communicates with or through the local area network 3372 via a network interface or adapter 3376 and typically includes interfaces, such as a modem 3378, or other apparatus, for establishing communications with or through the WAN 3374, such as the Internet. The modem 3378, which can be internal or external, is coupled to the system bus 3308 via a serial port interface.

In a networked environment, program modules depicted relative to the computation resource 3302, or portions thereof, can be stored in remote memory apparatus. It will be appreciated that the network connections shown are exemplary, and other means of establishing a communications link between various computer systems and elements can be used.

A user of a computer can operate in a networked environment using logical connections to one or more remote computers, such as a remote computer 3360, which can be a personal computer, a server, a router, a network PC, a peer device or other common network node. Typically, a remote computer 3360 includes many or all of the elements described above relative to the computer 3300 of FIG. 33.

The computation resource 3302 typically includes at least some form of computer-readable media. Computer-readable media can be any available media that can be accessed by the computation resource 3302. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 3302.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

FIG. 34 is a representation of display 3400 that is presented on the display device of apparatus in FIGS. 3-14 and 35-39, according to an implementation.

Some implementations of display 3400 include a representation of three detection modes 3402, a first detection mode being detection and display of surface temperature, a second detection mode being detection and display of body temperature and a third detection mode being detection and display of room temperature.

Some implementations of display 3400 include a representation of Celsius 3404 that is activated when the apparatus is in Celsius mode.

Some implementations of display 3400 include a representation of a sensed temperature 3406.

Some implementations of display 3400 include a representation of Fahrenheit 3408 that is activated when the apparatus is in Fahrenheit mode.

Some implementations of display 3400 include a representation of a mode 3410 of site temperature sensing, a first site mode being detection of an axillary surface temperature, a second site mode being detection of an oral temperature, a third site mode being detection of a rectal temperature and a fourth site mode being detection of a core temperature.

Some implementations of display 3400 include a representation of a temperature traffic light 3412, in which a green traffic light indicates that the temperature 320 is good; an amber traffic light indicates that the temperature 320 is low; and a red traffic light indicates that the temperature 320 is high.

Some implementations of display 3400 include a representation of a probe mode 3414 that is activated when the sensed temperature 3406 is from a contact sensor.

Some implementations of display 3400 include a representation of the current time/date 3416 of the apparatus.

FIG. 35-39 are schematics of the electronic components of a non-touch thermometer 3500 having a digital IR sensor. FIG. 35 is a portion of the schematic of the non-touch thermometer 3500 having a digital IR sensor, according to an implementation. As discussed above in regards to FIG. 4 and FIG. 3, thermal isolation of the digital IR sensor is an important feature. In a second circuit board 3501, a digital IR sensor 308 is thermally isolated from the heat of the microprocessor 3504 (shown in FIG. 36) through a first digital interface 3502. The digital IR sensor 308 is not mounted on the same circuit board 3505 as the microprocessor 3504 (shown in FIG. 36) which reduces heat transfer from a first circuit board 3505 to the digital IR sensor 308. The non-touch thermometer 3500 also includes a second circuit board 3501, the second circuit board 3501 including a second digital interface 3512, the second digital interface 3512 being operably coupled to the first digital interface 3502 and a digital infrared sensor 308 being operably coupled to the second digital interface 3512, the digital infrared sensor 308 having ports that provide only digital readout. The microprocessor 3504 (shown in FIG. 36) is operable to receive from the ports that provide only digital readout a digital signal that is representative of an infrared signal generated by the digital infrared sensor 308 and the microprocessor 3504 (shown in FIG. 36) is operable to determine a temperature from the digital signal that is representative of the infrared signal. The first circuit board 3505 includes all of the components in FIG. 35, FIG. 36 and FIG. 37 other than the second circuit board 3501, the digital IR sensor 308 and the second digital interface 3512.

Figure 36:
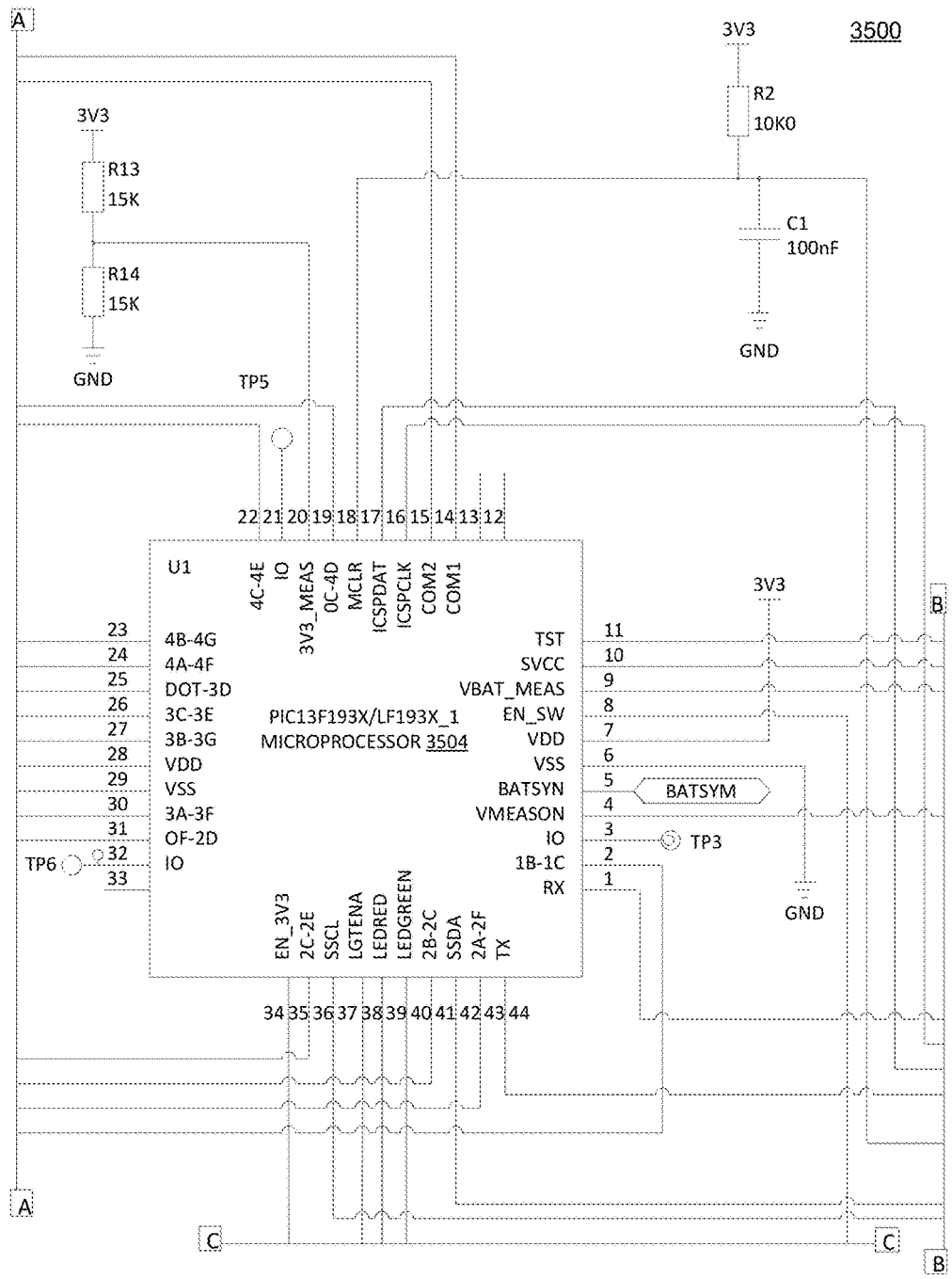
FIG. 36 is a portion of the schematic of the non-touch thermometer having the digital IR sensor, according to an implementation.

FIG. 36 is a portion of the schematic of the non-touch thermometer 3500 having the digital IR sensor, according to an implementation. A non-touch thermometer 3500 includes a first circuit board 3505, the first circuit board 3505 including the microprocessor 3504.

Figure 37:
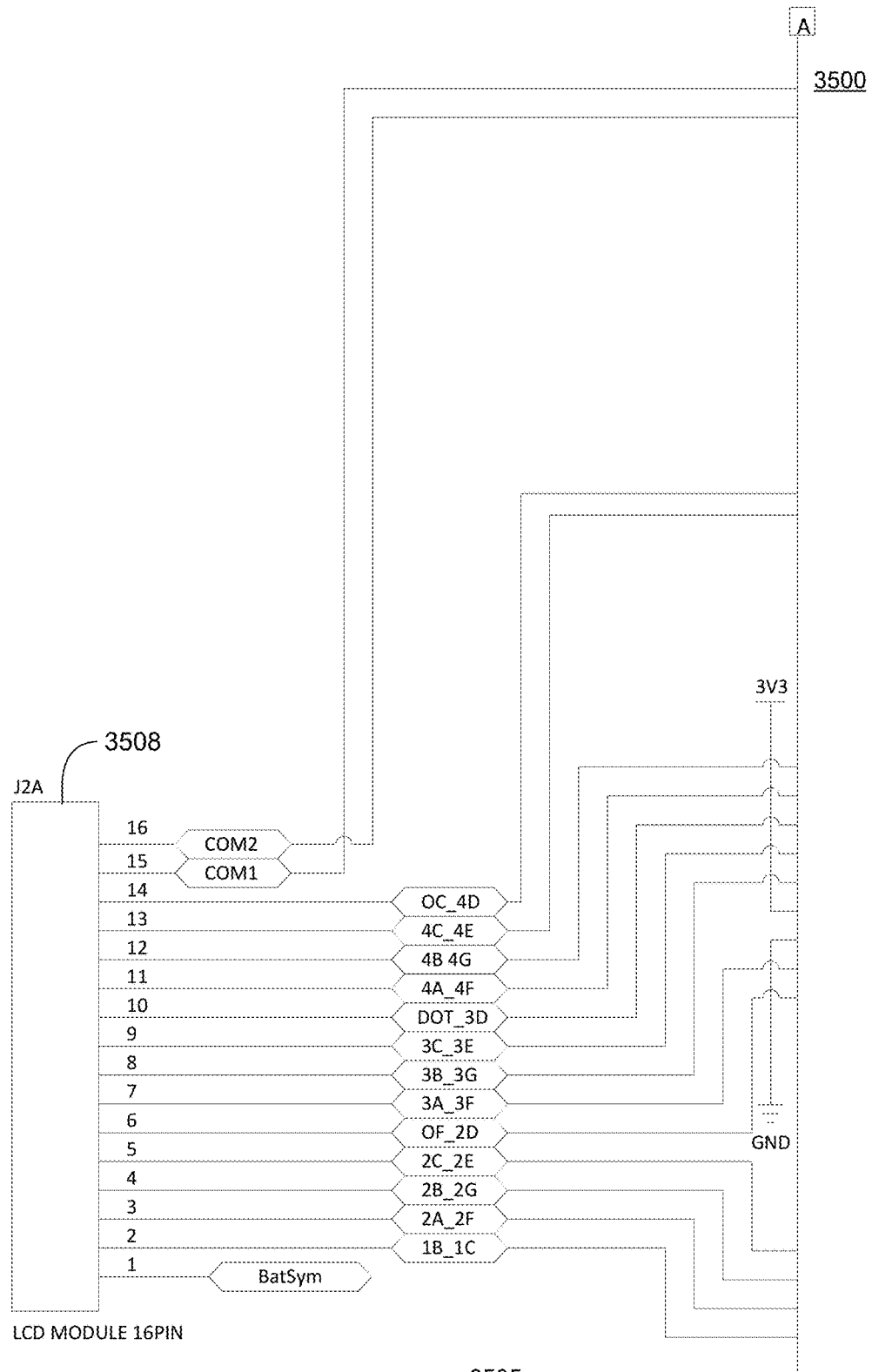
FIG. 37 is a portion of the schematic of the non-touch thermometer having the digital IR sensor, according to an implementation.

FIG. 37 is a portion of the schematic of the non-touch thermometer 3500 having the digital IR sensor, according to an implementation. The first circuit board 3505 includes a display device that is operably coupled to the microprocessor 3504 through a display interface 3508.

Figure 38:
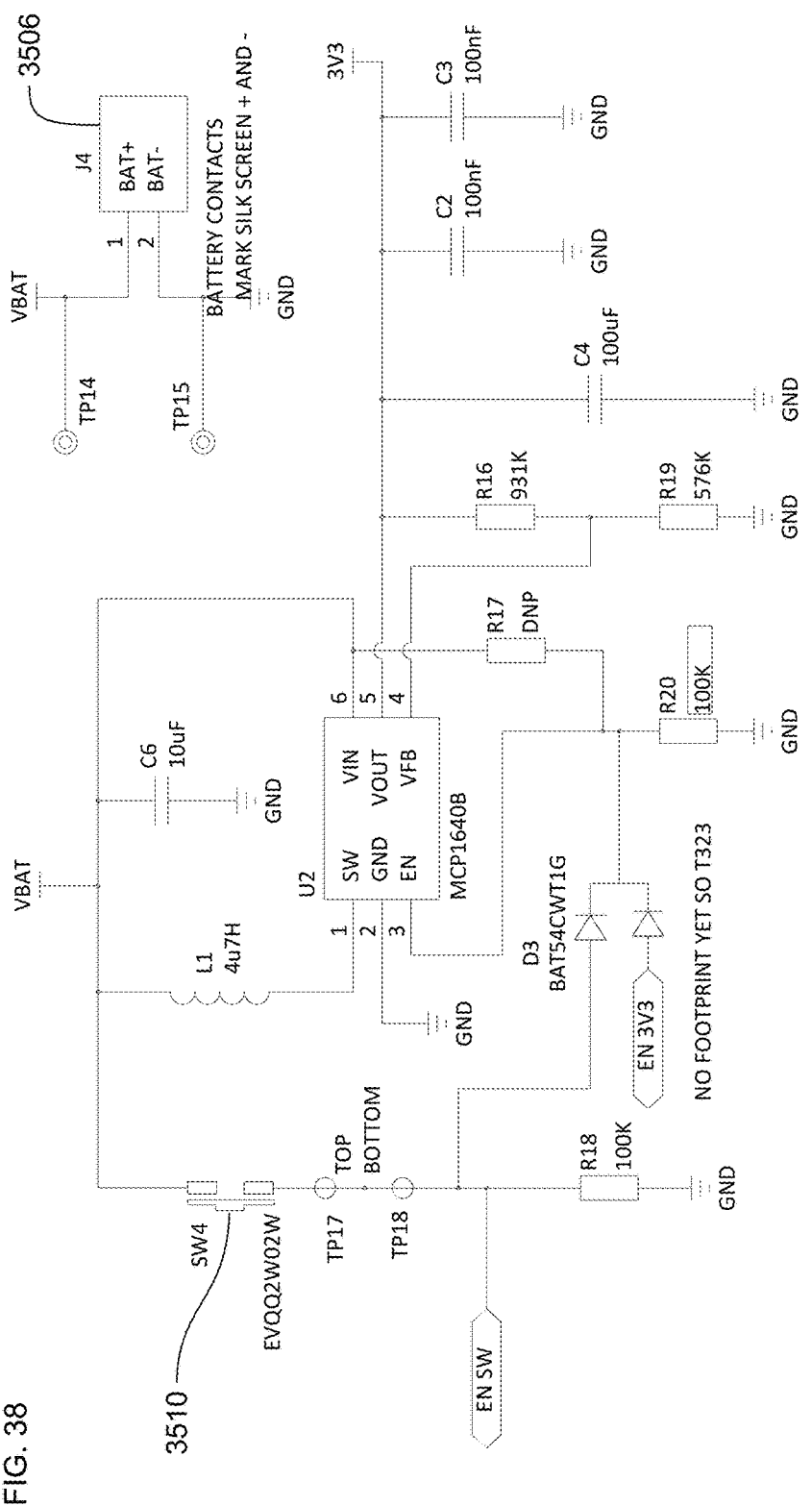
FIG. 38 is a circuit that is a portion of the schematic of the non-touch thermometer having the digital IR sensor, according to an implementation.
Figure 39:
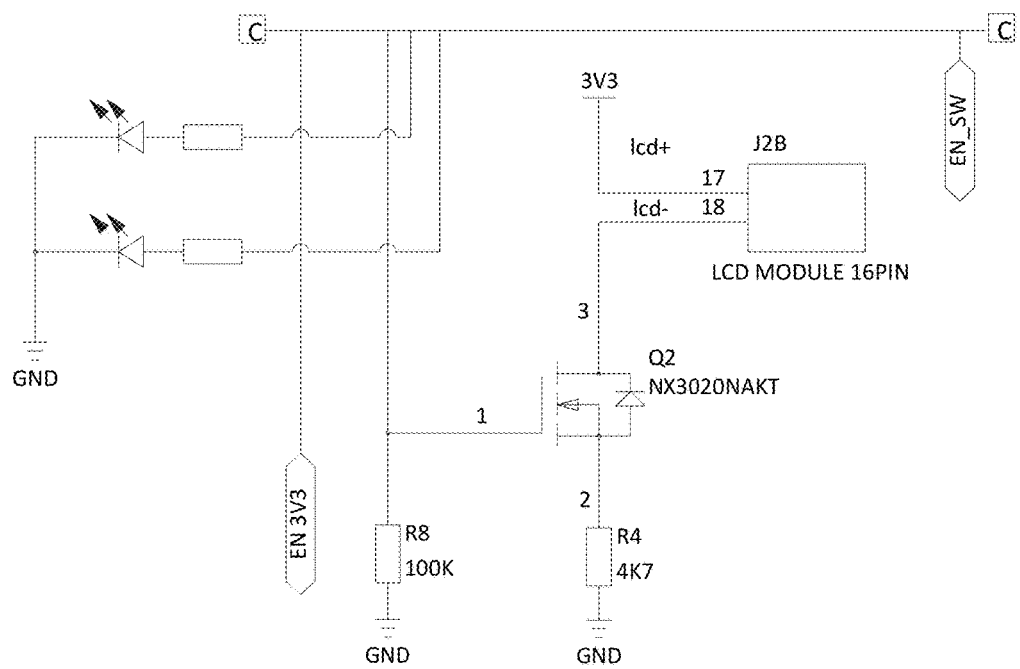
FIG. 39 is a circuit that is a portion of the schematic of the non-touch thermometer having the digital IR sensor, according to an implementation.

FIG. 38 is a portion of the schematic of the non-touch thermometer 3500 having the digital IR sensor, according to an implementation. Circuit 3500 includes a battery 3506 that is operably coupled to the microprocessor 3504, a single button 3510 that is operably coupled to the microprocessor 3504.

FIG. 37 is a portion of the schematic of the non-touch thermometer 3500 having the digital IR sensor, according to an implementation.

The non-touch thermometer further includes a housing, and where the battery 304 is fixedly attached to the housing. The non-touch thermometer where an exterior portion of the housing further includes a magnet.

In some implementations, the microprocessor 302, microprocessor 604, microprocessor 3504 in FIG. 35, main processor 3202 in FIG. 32 or processing unit 3304 in FIG. 33 that do not use the digital infrared sensor 308 can be a digital signal processor (DSP) that is specialized for signal processing such as the Texas Instruments® C6000 series DSPs, the Freescale® MSC81xx family.

In some implementations, the microprocessor 604, microprocessor 3504 in FIG. 35, main processor 3202 in FIG. 32 or processing unit 3304 in FIG. 33 can be a graphics processing unit GPU that use a specialized electronic circuit designed to rapidly manipulate and alter memory to accelerate the creation of images in a frame buffer, such as the Nvidia® GeForce 8 series.

In some implementations, the microprocessor 302, microprocessor 604, microprocessor 3504 in FIG. 35, main processor 3202 in FIG. 32 or processing unit 3304 in FIG. 33 can be field-programmable gate array (FPGA) that is an integrated circuit designed to be configured by a customer or a designer after manufacturing according to a hardware description language (HDL) using programmable logic components called "logic blocks", and a hierarchy of reconfigurable interconnects that allow the blocks to be "wired together" that are changeable logic gates that can be interwired in different configurations that perform analog functions and/or digital functions. Logic blocks can be configured to perform complex combinational functions, or merely simple logic gates such as AND and XOR. In most FPGAs, the logic blocks also include memory elements, which may be simple flip-flops or more complete blocks of memory.

Figure 40:
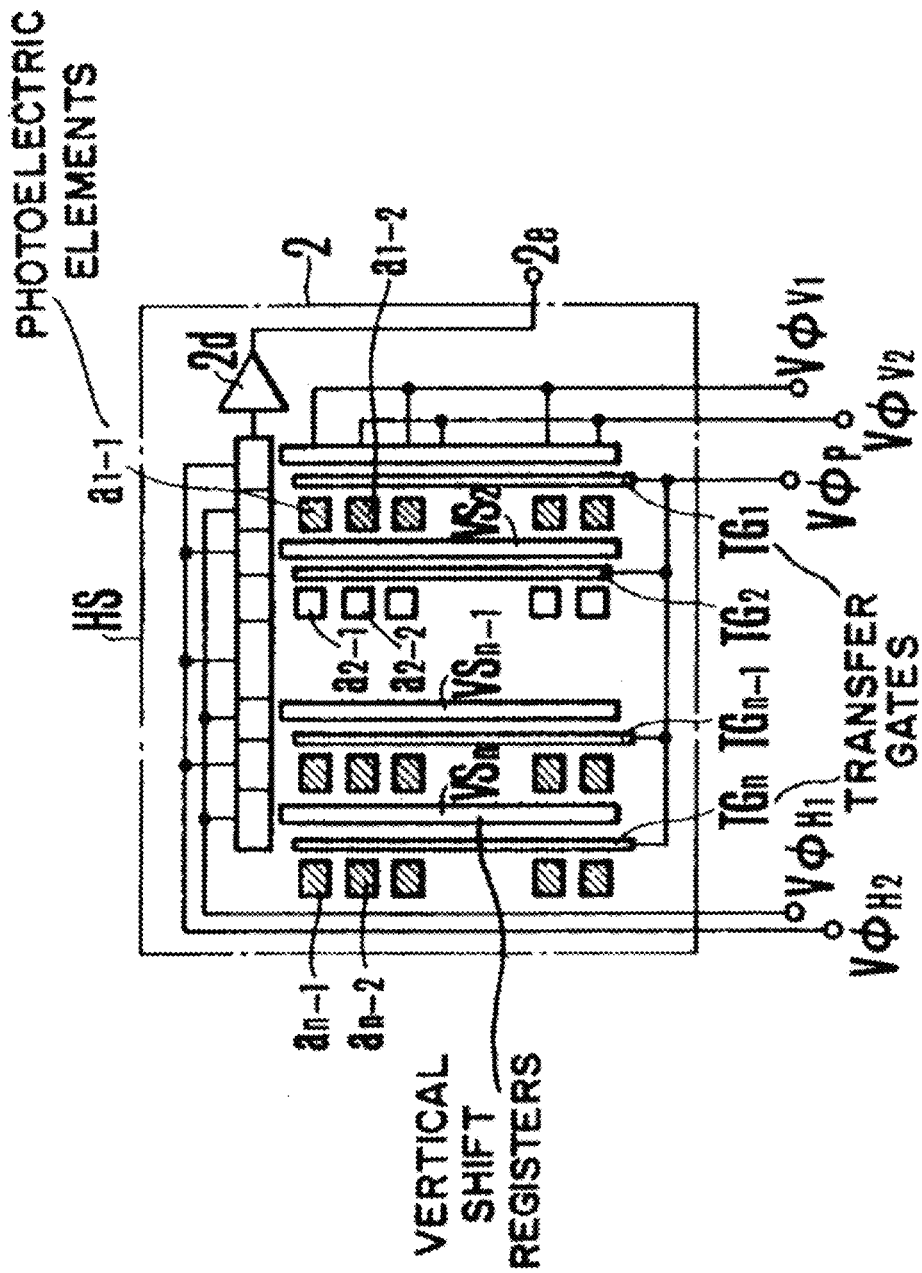
FIG. 40 is a block diagram of a solid-state image transducer, according to an implementation.

FIG. 40 is a block diagram of a solid-state image transducer 4000, according to an implementation. The solid-state image transducer 4000 includes a great number of photoelectric elements, a.sub.1..sub.1, a.sub.2..sub.1, . . . , a.sub.mn, in the minute segment form, transfer gates TG1, TG2, . . . , TGn responsive to a control pulse V.sub.ϕP for transferring the charges stored on the individual photoelectric elements as an image signal to vertical shift registers VS1, VS2, . . . , VSn, and a horizontal shift register HS for transferring the image signal from the vertical shift registers VSs, through a buffer amplifier 2d to an outlet 2e. After the one-frame image signal is stored, the image signal is transferred to vertical shift register by the pulse V.sub.ϕP and the contents of the vertical shift registers VSs are transferred upward line by line in response to a series of control pulses V.sub.ϕV1, V.sub.ϕV2. During the time interval between the successive two vertical transfer control pulses, the horizontal shift register HS responsive to a series of control pulses V.sub.ϕH1, V.sub.ϕH2 transfers the contents of the horizontal shift registers HSs in each line row by row to the right as viewed in FIG. 40. As a result, the one-frame image signal is formed by reading out the outputs of the individual photoelectric elements in such order.

Figure 41:
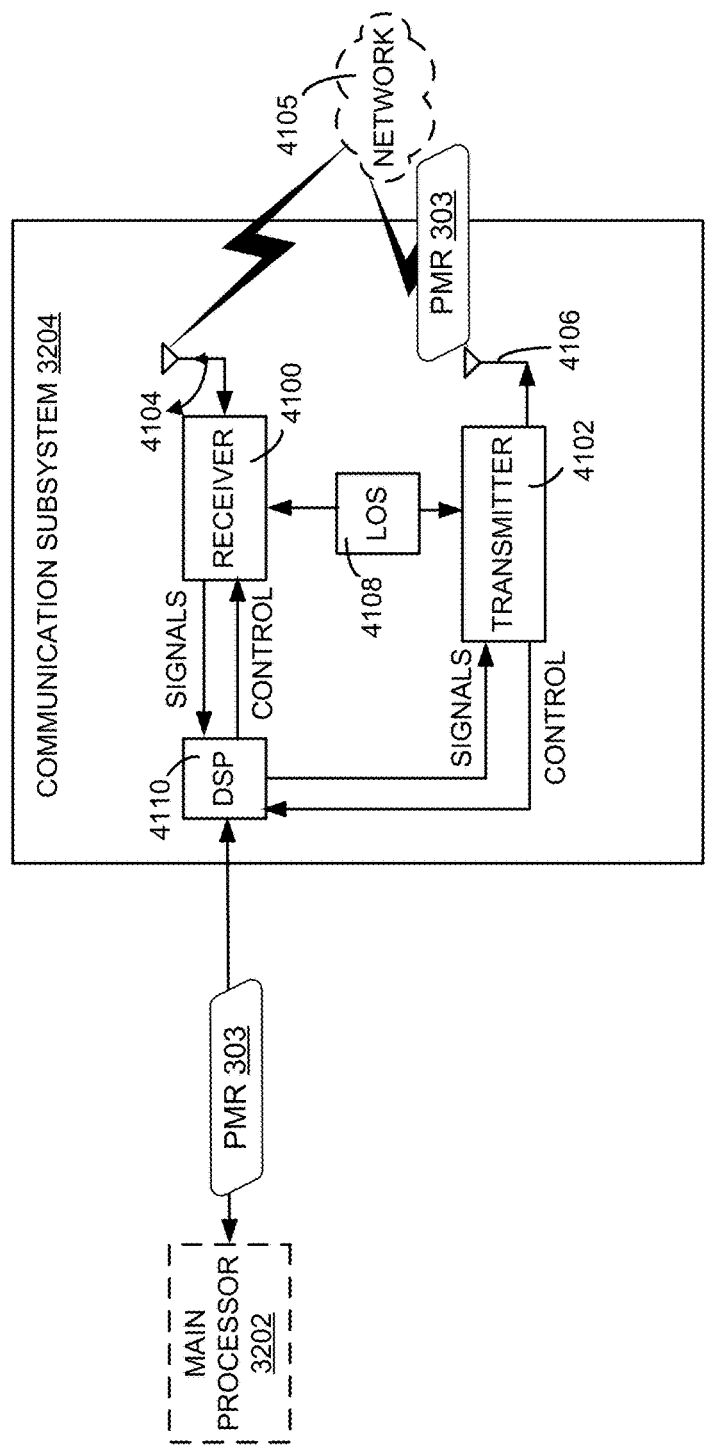
FIG. 41 is a block diagram of the communication subsystem, according to an implementation.

FIG. 41 is a block diagram of the communication subsystem 338, according to an implementation. The communication subsystem 338 includes a receiver 4100, a transmitter 4102, as well as associated components such as one or more embedded or internal antenna elements 4104 and 4106, Local Oscillators (LOs) 4108, and a processing module such as a Digital Signal Processor (DSP) 4110. The particular implementation of the communication subsystem 338 is dependent upon communication protocols of a wireless network 4105 with which the mobile device is intended to operate. Thus, it should be understood that the implementation illustrated in FIG. 41 serves only as one example. Examples of the hand-held medical-data capture-device 104 include mobile device 3200, non-touch biologic detector in FIGS. 3-5, apparatus that estimates a body core temperature 4-10, apparatus of variation amplification FIGS. 16-24 and non-touch thermometer 3500. Examples of the wireless network 4105 include network 3205 in FIG. 32.

Signals received by the antenna 4104 through the wireless network 4105 are input to the receiver 4100, which may perform such common receiver functions as signal amplification, frequency down conversion, filtering, channel selection, and analog-to-digital (A/D) conversion. A/D conversion of a received signal allows more complex communication functions such as demodulation and decoding to be performed in the DSP 4110. In a similar manner, signals to be transmitted are processed, including modulation and encoding, by the DSP 4110. These DSP-processed signals are input to the transmitter 4102 for digital-to-analog (D/A) conversion, frequency up conversion, filtering, amplification and transmission over the wireless network 4105 via the antenna 4106. The DSP 4110 not only processes communication signals, but also provides for receiver and transmitter control. For example, the gains applied to communication signals in the receiver 4100 and the transmitter 4102 may be adaptively controlled through automatic gain control algorithms implemented in the DSP 4110.

The wireless link between the hand-held medical-data capture-device 104 and the wireless network 4105 can contain one or more different channels, typically different RF channels, and associated protocols used between the hand-held medical-data capture-device 104 and the wireless network 4105. An RF channel is a limited resource that must be conserved, typically due to limits in overall bandwidth and limited battery power of the hand-held medical-data capture-device 104.

When the hand-held medical-data capture-device 104 is fully operational, the transmitter 4102 is typically keyed or turned on only when it is transmitting to the wireless network 4105 and is otherwise turned off to conserve resources. Similarly, the receiver 4100 is periodically turned off to conserve power until the receiver 4100 is needed to receive signals or information (if at all) during designated time periods.

The PMR 103 is received by the communication subsystem 338 from the main processor 3202 at the DSP 4110 and then transmitted to the wireless network 4105 through the antenna 4104 of the receiver 4100.

A non-touch biologic detector or thermometer that senses temperature through a digital infrared sensor, and transmits the temperature to an electronic medical record system. A technical effect of the apparatus and methods disclosed herein electronic transmission of a body core temperature that is estimated from signals from the non-touch electromagnetic sensor to a heterogeneous electronic medical record system. Another technical effect of the apparatus and methods disclosed herein is generating a temporal variation of images from which a vital sign can be transmitted to a heterogeneous electronic medical record system. Although specific implementations are illustrated and described herein, it will be appreciated by those of ordinary skill in the art that any arrangement which is generated to achieve the same purpose may be substituted for the specific implementations shown. This application is intended to cover any adaptations or variations.

In particular, one of skill in the art will readily appreciate that the names of the methods and apparatus are not intended to limit implementations. Furthermore, additional methods and apparatus can be added to the modules, functions can be rearranged among the modules, and new modules to correspond to future enhancements and physical devices used in implementations can be introduced without departing from the scope of implementations. One of skill in the art will readily recognize that implementations are applicable to future non-touch temperature sensing devices, different temperature measuring sites on humans or animals and new display devices.

The terminology used in this application meant to include all temperature sensors, processors and operator environments and alternate technologies which provide the same functionality as described herein.

The invention claimed is:

1. A non-touch thermometer to measure a temperature, the non-touch thermometer comprising:
    a microprocessor;
    a wireless communication subsystem that is operably coupled to the microprocessor and that is operable to transmit a representation of the temperature;
    a battery operably coupled to the microprocessor;
    a digital infrared sensor operably coupled to the microprocessor with no analog-to-digital converter operably coupled between the digital infrared sensor and the microprocessor, the digital infrared sensor having only digital readout ports, the digital infrared sensor comprising a low noise amplifier, an analog-to-digital converter, a digital signal processor, and a pulse width modulator (PWM) in a single industry standard package; wherein the digital infrared sensor is configured with no need for recalibration after an initial factory calibration with an emissivity range from 0.1 to 1.0,
    wherein the microprocessor is operable to receive from the digital readout ports a digital signal that is representative of an infrared signal, the infrared signal acquired from a forehead of a user and detected by the digital infrared sensor, and the microprocessor is further operable to determine the temperature from the received digital signal by using the PWM.

2. The non-touch thermometer of claim 1, wherein a display device further comprises:
    a green traffic light operable to indicate that the temperature is good;
    an amber traffic light operable to indicate that the temperature is low; and
    a red traffic light operable to indicate that the temperature is high.

3. The non-touch thermometer of claim 1, the microprocessor further comprising:
    a pixel-examination-module configured to examine pixel values of the at least two images, a temporal-variation module to determine temporal variation of the pixel values between the at least two images being below a particular threshold, a signal processing module configured to amplify the temporal variation resulting in amplified temporal variation, and a visualizer to visualize a pattern of flow of blood in the amplified temporal variation in the at least two images.

4. The non-touch thermometer of claim 1 further comprising:
the digital infrared sensor having no analog sensor readout ports.

5. The non-touch thermometer of claim 1 wherein the wireless communication subsystem transmits through an Internet Protocol tunnel.

6. The non-touch thermometer of claim 1 wherein the non-touch thermometer does not support specific discovery protocols or domain name service.

7. The non-touch thermometer of claim 1 wherein a connection is established and data is pushed from the non-touch thermometer through the wireless communication subsystem, thereafter an external device controls flow of the data between the non-touch thermometer and the external device, wherein the connection further comprises: an authenticated communication channel.

8. The non-touch thermometer of claim 1, the wireless communication subsystem is configured to operate on a specific segment of a network.

9. The non-touch thermometer of claim 1, wherein the wireless communication subsystem further comprises:
a component that is operable to transmit a representation of date and time, operator identification, patient identification and manufacturer, model number and firmware revision of the non-touch thermometer.

10. The non-touch thermometer of claim 1 further comprising:
a camera operably coupled to the microprocessor and providing at least two images to the microprocessor; and
the microprocessor including a cropper that is operable to receive the at least two images and operable to crop the images to exclude a border area of the images, generating at least two cropped images, the microprocessor also including a temporal-variation-amplifier of at least two cropped images that is operable to generate a temporal variation, the microprocessor also including a vital-sign generator that is operably coupled to the temporal-variation-amplifier that is operable to generate at least one vital sign from the temporal variation and the microprocessor also operably coupled to the vital-sign generator that is operable to display the at least one vital sign.

11. The non-touch thermometer of claim 1, wherein the temperature further comprises a body core temperature and wherein determining the body core temperature is based on a cubic relationship representing three thermal ranges between a numerical representation of electromagnetic energy of an external source point and the body core temperature, wherein the cubic relationship includes a coefficient representative of different relationships between the external source point and the body core temperature in the three thermal ranges.

* * * * *